US012736529B2

(12) United States Patent
Bergmann et al.

(10) Patent No.: US 12,736,529 B2
(45) **Date of Patent: *Sep. 15, 2026**

(54) STREPTAVIDIN-COATED SOLID PHASES WITH A MEMBER OF A BINDING PAIR

(71) Applicant: Roche Diagnostics Operations, Inc., Indianapolis, IN (US)

(72) Inventors: Frank Bergmann, Penzberg (DE); Dieter Heindl, Penzberg (DE); Tobias Oelschlaegel, Penzberg (DE); Johannes Stoeckel, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1344 days.

This patent is subject to a terminal disclaimer.

(21) Appl. No.: 17/292,660

(22) PCT Filed: Nov. 14, 2019

(86) PCT No.: PCT/EP2019/081271

§ 371 (c)(1),
(2) Date: May 10, 2021

(87) PCT Pub. No.: WO2020/099533

PCT Pub. Date: May 22, 2020

(65) Prior Publication Data

US 2022/0011301 A1 Jan. 13, 2022

(30) Foreign Application Priority Data

Nov. 16, 2018 (EP) .................................... 18206779

(51) Int. Cl.
*G01N 33/543* (2006.01)

(52) U.S. Cl.
CPC ................ *G01N 33/54306* (2013.01); *G01N 33/54393* (2013.01); *G01N 2333/36* (2013.01)

(58) Field of Classification Search
None
See application file for complete search history.

(56) References Cited

U.S. PATENT DOCUMENTS

| | | | |
|---|---|---|---|
| 4,554,088 A | 11/1985 | Whitehead et al. | |
| 4,628,037 A | 12/1986 | Chagnon et al. | |
| 4,695,393 A | 9/1987 | Whitehead et al. | |
| 4,698,302 A | 10/1987 | Whitehead et al. | |
| 4,752,638 A | 6/1988 | Nowinski et al. | |
| 4,816,567 A | 3/1989 | Cabilly et al. | |
| 4,965,392 A | 10/1990 | Fritzberg et al. | |
| 5,545,806 A | 8/1996 | Longberg et al. | |
| 5,545,807 A | 8/1996 | Surani et al. | |
| 5,569,825 A | 10/1996 | Lonberg et al. | |
| 5,625,125 A | 4/1997 | Bennett et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 8,871,686 B2 | 10/2014 | Ghadessy et al. | |
| 9,017,992 B2 | 4/2015 | Winther et al. | |
| 2003/0138974 A1 | 7/2003 | Lawerence et al. | |
| 2004/0023207 A1* | 2/2004 | Polansky | A61K 48/005 435/456 |
| 2005/0118728 A1 | 6/2005 | Caldwell et al. | |
| 2014/0256588 A1 | 9/2014 | Glezer et al. | |
| 2018/0149656 A1 | 5/2018 | Angione et al. | |
| 2018/0172680 A1 | 6/2018 | Zarnt et al. | |
| 2020/0354677 A1* | 11/2020 | Lee | A61K 40/11 |
| 2021/0155976 A1* | 5/2021 | Bergmann | C12Q 1/6813 |
| 2021/0389313 A1* | 12/2021 | Ward | G01N 33/553 |

FOREIGN PATENT DOCUMENTS

| | | |
|---|---|---|
| CN | 102549427 A | 7/2012 |
| CN | 108333344 A | 7/2018 |
| EP | 0138297 A1 | 6/1984 |
| EP | 0404097 A2 | 12/1990 |
| EP | 0488152 A1 | 11/1991 |
| EP | 0540037 A2 | 5/1993 |
| EP | 0698792 A1 | 4/1994 |
| EP | 0643305 A2 | 9/1994 |

(Continued)

OTHER PUBLICATIONS

Samarasinghe et al., Biotin Interference with routine clinical immunoassays: understand the causes and mitigate the risks, Endocrine Practice, vol. 23, No. 8, Aug. 2017, pp. 989-998. (Year: 2017).*
Kumar et al. Parallel RNA-strand recognition by 2'-amino-beta-L-LNA. Bioorg. Med. Chem. Lett. 19:2396-2399 (2009). (Year: 2009).*
Bruggemann et al., Designer Mice: The Production of Human Antibody Repertoires in Transgenic Animals; Year Immunol., 1993, vol. 7, pp. 33-40.
Diamandis et al., The Biotin-(Strept)Avidin System: Principles and Applications in Biotechnology; Clin. Chem., 1991, vol. 37, vol. 5, pp. 625-636.
Eze et al., Analysis of in Situ LNA and DNA Hybridization Events on Microspheres; American Chemical Society; 2017 vol. 18, pp. 1086-1096.
Fellouse et al., Synthetic antibodies from a four-amino-acid code: A dominant role for tyrosine in antigen recognition; PNAS, 2004, vol. 101, No. 34, pp. 12467-12472.

(Continued)

*Primary Examiner* — Samuel C Woolwine
(74) *Attorney, Agent, or Firm* — Taft Stettinius & Hollister LLP

(57) ABSTRACT

The present disclosure relates to a solid phase coated with (strept)avidin and having attached thereto, by way of biotin: (strept)avidin interaction, a biotinylated first member of a binding pair, wherein the attached first member is capable of binding to a second member of the binding pair, but is not capable of binding to biotin or to (strept)avidin, and wherein no member of the binding pair is capable of hybridizing with a naturally-occurring single-stranded nucleic acid. The solid phase is particularly useful in immunoassays with samples having high content in biotin or (strept)avidin-binding derivatives thereof. The present disclosure further provides uses, kits and methods, particularly for determination of an analyte in a sample.

24 Claims, 8 Drawing Sheets

Specification includes a Sequence Listing.

(56) References Cited

FOREIGN PATENT DOCUMENTS

| | | | |
|---|---|---|---|
| EP | 095517 | A1 | 3/1998 |
| JP | 2003207512 | A | 7/2003 |
| JP | 2016511417 | A | 4/2016 |
| WO | 198910979 | A1 | 11/1989 |
| WO | 199110741 | A1 | 7/1991 |
| WO | 199301161 | A1 | 1/1993 |
| WO | 199524649 | A1 | 9/1995 |
| WO | 199633735 | A1 | 10/1996 |
| WO | 199634096 | A1 | 10/1996 |
| WO | 9824893 | A2 | 6/1998 |
| WO | 199824896 | A1 | 6/1998 |
| WO | 199829736 | A1 | 7/1998 |
| WO | 199839352 | A1 | 9/1998 |
| WO | 199914226 | A1 | 3/1999 |
| WO | 200056746 | A2 | 9/2000 |
| WO | 2013188756 | A1 | 12/2013 |
| WO | 2017-032726 | A1 | 3/2017 |

OTHER PUBLICATIONS

Fishwild et al., High-avidity human IgGk monoclonal antibodies from a novel stain of minilocus transgenic mice; Nature Biotechnology, 1996, vol. 14, 7-pages.
Glasel, A Nuclear Magnetic Resonance Investigation of Biotin. The Biotin Sulfonium Ion; Nuclear Magnetic Resonance Pectra of Biotin, 1966, vol. 5, No. 6, 5-pages.
Grimsey et al., Populatoin pharmacokinetics of exogenous biotin and the relationship between biotin serum levels and in vitro immunoassay interference; International Journal of Pharmacokinetics; 10-pages.
Haemmering, Production of Antibody-Producing Hybridomas in the Rodent Systems; 24-pages.
Harlow et al., Antibodies, A Laboratory Manual. 2014, 8-pages.
Henry et al., Interference by biotin therapy on measurement of TSH and FT4 by enzymeimmunoassay on Boehringer Mannheim ES700 analyser; Ann Clin Ciochem, 1996, vol. 33, pp. 162-163.
Holliger et al., "Diabodies": Small bivalent and bispecific antibody fragments; Prox. Natl. Acad., Sci., 1993, vol. 90, pp. 6444-6448.
Hongo et al., Developmentand Characterization of Murine Monoclonal Antibodies to the Latency-Associated Peptide of Transforming Growth Factor B1; Hybridoma, 1995, vol. 14, No. 3, 8-pages.
Hudson et al., Engineered Antibodies; Nature Medicine, 2003, vol. 9, No. 1, 6-pages.
Huston et al., Protein Engineering of Singl-Chain Fv Analogs and Fusion Proteins; Antibodies and Antigens; 44-pages.
Jakobovits et al., Analysis of homozygous mutant chimeric mice: Deletion of the immunoglobulin heavy-chain joining region blocks B-cell development and antibody production; Proc. Natl., Acad. Sci., 1993, Genetics; vol. 90, pp. 2551-2555.
Jakobovits et al., Germ-line transmission and expression of a human-derived yeast artificial chromosome; Letters to Nature, Cell Genesys, Inc., 1993. 4-pages.
Kohle et al., Continuous cultures of fused cells secreting antibody of predefined specificity; Nature, 1975, vol. 256, 3-pages.
Koshkin et al., LNA (Locked Nucleic Acid): An RNA Mimic Forming Exceedingly Stable LNA:LNA Duplexes; J. Am. Chem. Soc., 1998, vol. 120, pp. 13252-13253.
Koshkin et al., A Simplified and Efficient Route to 2'-0, 4'-C-Methylene-Linked Bicyclic Ribonucleosides (Locked Nucleic Acid); J. Org. Chem., 2001, vol. 66, pp. 8504-8512.
Kwok et al., Biotin interference on TSH and free thyroid hormone measurement; 2012, vol. 22, No. 3, 3-pages.
Lee et al., High-affinity Human Antibodies from Phage-displayed Synthetic Fab Libraries with a Single Framework Scaffold; J. Mol. Biol. 2004, vol. 340, pp. 1073-1093.
Lee et al., Bivalent antibody phage display mimics natural immunoglobulin; Journal of Immunological Methods, 2004, vol. 284, pp. 119-132.
Lett et al., Analyse Conformationnelle DE Derives DU Thiophane, DES Sulfoxydes ET Sulfones Correspondants; Tetrahedron, 1074, vol. 30, pp. 3365-3377.
Lonberg et al., Antigen-specific human antibodies from mice comprising four distinct genetic modifications; Nature, 1994, vol. 368, 4-pages.
Lonberg et al., Human Antibodies from Transgenic Mice; Intern. Rev. Immunol., 1995, vol. 13, pp. 65-93.
Marks et al., By-passing Immunization: Human Antibodies from V-gene Libraries Displayed on Phage; J. Mol Biol., 1991, vol. 221, pp. 581-597.
Marks et al., By-passing Immunization: Building High Affinity Human Antibodies By Chain Shuffling: Research, Biotechnology, 1992, vol. 10, 5-pages.
Marquet, Andree; New Aspects of the Chemistry of Biotin and of some Analogs; Pure & Appl. Chem., 1977, vol. 49, pp. 183-196.
Mastrangeli et al., Cloning of Murine LAG-3 by Magnetic Bead Bound Homologous Probes and PCR (Gene-Capture PCR); Analytical Biochemistry, 1996, vol. 241, pp. 93-102.
Melville et al., The Structure of Biotin: The Formation of Thiophenevaleric Acid From Biotin; 1942, 7-pages.
Mohrle et al., Determination of affinity constants of locked nucleic acid (LNA) and DNA duplex formation using label free sensor technology; The Analyst, 2005, 5-pages.
Morrison et al., Chimeric human antibody molecules: Mouse antigen-binding domains with human constant region domains; Proc. Natl. Acad. Sci., 1984, vol. 81, pp. 6851-6855.
Morrison, Sherie L., Success in specification; News and views; Nature, 1994, vol. 368, 2-pages.
Neuberger, MIchael, Generating high-avidity human Mabs in mice; Nature Biotechnology, vol. 14, 1996, 1-page.
Piran et al., Dissociation rate constant of the biotin-streptavidin complex; Journal of Immunological Methods, 1990, vol. 133, pp. 141-143.
Sedel et al., Hight doses of biotin in chronic progressive multiple sclerosis: A pilot study; Multiple Sclerosis and Related Disorders; 2015, vol. 4, pp. 159-169.
Shetty et al., Can we beat the biotin-avidin pair?: curcurbit[7]uril-based ultrahigh affinity host-guest complexes and their applications; Chem Coc. Rev., 2015, vol. 44, 15-pages.
Sidhu et al., Phage-displayed Antibody Libraries of Synthetic Heavy Chain Complementarity Determining Regions; J. Mol. Biol. 2004, vol. 338, pp. 299-310.
Srisa-Art et al., Monitoring of Real-Time Streptavidin-Biotin Binding Kinetics Using Droplet Microfluidics; Anal. Chem. 2008, vol. 80, pp. 7063-7067.
Tolstrup et al., OligoDesign: optimal design of LNA (locked nucleic acid) oligonucleotide capture probes for gene expression profiling; Nucleic Acids Research, 2003, vol. 31, No. 13, 5-pages.
International Search Report, European Patent Office, International Patent Application No. PCT/EP2019/081271, Feb. 13, 2020, 5 pages.
Written Opinion of the International Searching Authority, European Patent Office, International Patent Application No. PCT/EP2019/081271, Feb. 13, 2020, 9 pages.
International Preliminary Report on Patentability, European Patent Office, International Patent Application No. PCT/ EP2019/081271, May 18, 2021, 10 pages.
Clackson et al., Making antibody fragments using phage display libraries, Nature, vol. 352, 1991, pp. 624-628.
Qu et al., Synthesis and NMR elucidation of four novel 2-(trimethylsilyl)ethyl glycosides, Research On Chemical Intermediates, vol. 40, No. 4, 2014, pp. 1557-1564.
Hassan et al., 6-Methylpurine derived sugar modified nucleosides: Synthesis and evaluation of their substrate activity with purine nucleoside phosphorylases, Bioorganic Chemistry, vol. 65, 2016, pp. 9-16.

* cited by examiner

A

B

A

B

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 1

ctgcctgacg                                                            10


<210> SEQ ID NO 2
<211> LENGTH: 10
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 2

cgtcaggcag                                                            10


<210> SEQ ID NO 3
<211> LENGTH: 12
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
```

-continued stereoisomer, i.e. contining an L-form sugar as described in Example 1.

<400> SEQUENCE: 3
gactgcctga cg 12

<210> SEQ ID NO 4
<211> LENGTH: 12
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 4
cgtcaggcag tc 12

<210> SEQ ID NO 5
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 5 tgctcctg 8

<210> SEQ ID NO 6
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 6 caggagca 8

<210> SEQ ID NO 7
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 7 gcctgacg 8

<210> SEQ ID NO 8
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 8 cgtcaggc 8

<210> SEQ ID NO 9
<211> LENGTH: 9
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 9 tgctcctgt 9

<210> SEQ ID NO 10
<211> LENGTH: 9
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 10 acaggagca 9

<210> SEQ ID NO 11
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 11 gtgcgtct 8

<210> SEQ ID NO 12
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 12 agacgcac 8

<210> SEQ ID NO 13
<211> LENGTH: 8
<212> TYPE: DNA
<213> ORGANISM: Artificial Sequence
<220> FEATURE:
<223> OTHER INFORMATION: Artificially designed oligomer consisting of locked nucleic acid monomers, each monomer being a L-form stereoisomer, i.e. contining an L-form sugar as described in Example 1.

<400> SEQUENCE: 13 gttggtgt 8

```
<210> SEQ ID NO 14
<211> LENGTH: 8
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 14

acaccaac                                                                  8


<210> SEQ ID NO 15
<211> LENGTH: 15
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 15

gttggtgtgt tggtg                                                         15


<210> SEQ ID NO 16
<211> LENGTH: 15
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 16

caccaacaca ccaac                                                         15


<210> SEQ ID NO 17
<211> LENGTH: 9
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 17

gttggtgtg                                                                 9


<210> SEQ ID NO 18
<211> LENGTH: 9
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 18

cacaccaac                                                                 9


<210> SEQ ID NO 19
<211> LENGTH: 9
```

-continued

```
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 19

ggaagagaa                                                             9


<210> SEQ ID NO 20
<211> LENGTH: 9
<212> TYPE: DNA
<213> ORGANISM: Artificial Sequence
<220> FEATURE:
<223> OTHER INFORMATION: Artificially designed oligomer consisting of
      locked nucleic acid monomers, each monomer being a L-form
      stereoisomer, i.e. contining an L-form sugar as described in
      Example 1.

<400> SEQUENCE: 20

ttctcttcc                                                             9
```

STREPTAVIDIN-COATED SOLID PHASES WITH A MEMBER OF A BINDING PAIR

CROSS-REFERENCE TO RELATED APPLICATIONS

This application is a National Phase Application of International Patent Application No. PCT/EP2019/081271 (published as WO 2020/099533), filed Nov. 14, 2019, which claims priority to EP Patent Application No. 18206779.3, filed Nov. 16, 2018, each of which is hereby incorporated by reference in its entirety.

The present disclosure relates to a solid phase coated with (strept)avidin and having attached thereto, by way of <biotin:(strept)avidin> interaction, a biotinylated first member of a binding pair, wherein the attached first member is capable of binding to a second member of the binding pair, but is not capable of binding to biotin or to (strept)avidin, and wherein no member of the binding pair is capable of hybridizing with a naturally-occurring single-stranded nucleic acid. The solid phase is particularly useful in immunoassays with samples having high content in biotin or (strept)avidin-binding derivatives thereof. The present disclosure further provides uses, kits and methods, particularly for determination of an analyte in a sample.

BACKGROUND OF THE INVENTION

The present report relates to technically advantageous alternatives in assays which, in one assay step, require formation of a connected pair of two binders (=binding pair), and where the pair of binders so far used to be the <biotin:(strept)avidin> binding pair. Thus, particular focus is directed to biochemical applications in which the specific interaction of the two members of a binding pair and their eventual binding to each other has a functional role in the respective application.

Very frequently and well known to the skilled person, the <biotin:(strept)avidin> binding pair is used in heterogeneous immunoassays to immobilize a biotinylated analyte-specific capture agent on a solid phase. Another frequently used embodiment of immunoassays includes the step of immobilizing a biotinylated antigen on a solid phase using the <biotin:(strept)avidin> binding pair. The skilled person is aware of a large amount of already established solid phases having surfaces that are coated with (strept)avidin.

When a biotinylated compound (i.e. a biotin conjugate) that is initially provided in solution is to be attached to such an established solid phase that is contacted with the solution, problems can arise in cases when unconjugated (i.e. unbound and unobstructedly diffusing, ="free") biotin molecules are present in the same solution, in the same compartment, and at the same time. Under such circumstances the unconjugated biotin competes with the biotinylated compound for binding to (strept)avidin on the solid phase. Depending on the concentration of free biotin and the concentration of the biotinylated compound, an amount of the conjugate may become out-competed and thereby will not become bound by (strept)avidin. Considering a heterogeneous immunoassay, for example, a practical problem can arise if a substantially heightened amount of biotin in the sample to be assayed competes with the binding of a biotinylated analyte-specific capture antibody to a (strept)avidin-coated microwell plate or a (strept)avidin-coated magnetic particle. Thus, so-called biotin interference may cause less capture antibody to be anchored on the solid phase; less capture antibody can capture fewer amounts of analyte, and an incorrect assay result could be a consequence.

The above described situation is referred to as biotin interference. Biotin interference as a technical challenge in immunoassays has described earlier, e.g. by Kwok J S et al. (Pathology. 44 (2012) 278-280). The authors report biotin interference with regards to an immunoassay to determine TSH (thyroid stimulating hormone) and free thyroid hormone in blood plasma using an automated heterogeneous immunoassay. Among other sources, biotin interference is frequently due to intake of high dosage biotin, e.g. from specific supplements to the normal human diet. Biotin is believed to be a key contributor to keratin, and high dose biotin thus could improve quality and quantity of hair, nails and skin. Biotin is water-soluble and excreted rapidly. However, if high dose biotin supplementation is taken, rather high levels of biotin in the circulation may be present and the biotin in the circulation may also be present in a sample used for in vitro analysis for measurement of an analyte, i.e. in a sample like serum or plasma. Biotin comprised in a sample, if present at high levels might interfere in an assay for measurement of an analyte, which is employing a (strept)avidin-coated solid phase and a biotinylated specific binding agent.

One way to address this technical challenge is the replacement of the <biotin:(strept)avidin> binding pair with a different binding pair. Other binding pairs which could have similar properties as the <biotin:(strept)avidin> binding pair have been proposed, e.g. Cucurbit[n]uril Host-Guest Complexes, see Shetty D. et al. (Chem. Soc. Rev. 44 (2015) 8747-8761), to mention an exemplary and non-limiting embodiment of replacement binding pairs. U.S. Pat. No. 4,752,638 discloses a binding pair consisting of digoxin and a digoxin-specific monoclonal antibody.

But up to this point it appears that the theoretically and/or practically possible alternatives have not been used widely, just the contrary seems to be the case. This could be because no possible alternative linker chemistry has been identified, which is required to connect the members of an alternative binding pair with a target molecule or a solid phase. Such linker chemistry needs to be sufficiently versatile, simple, reproducible and robust.

Considering immunoassays and also other types of assays, a large number and many different kinds of (strept)avidin-coated solid phases have been developed, are known to the skilled person and are available for the practitioner. The biochemistry of (strept)avidin already provides a large number of techniques and applications. Particularly considering different solid phases the prior art still uses long-known processes to coat a multitude of surfaces with (strept)avidin, as disclosed in e.g. WO 1989/010979 A1 and EP 0643305 A2. A large number of different solid phases with streptavidin-coated surfaces have been described and are commercially available, including e.g. microwell plates, glass slides, culture dishes, vials, membranes, sensor chips, beads, magnetic particles and many more. Considering such materials and methods existing with respect to (strept)avidin, replacement of this binding partner with an alternative member of a binding pair requires significant effort, to reach a comparable stage and similar sophistication; in addition, alternative coating technologies need to be developed.

Thus, there is a particular need in the art of biochemistry to provide the means to attach binding partners other than (strept)avidin to solid phases. A particular need exists for solid phases used in detection assays such as immunoassays, specifically with respect to assaying samples which may contain free biotin. A desired assay unaffected by biotin interference would not need to rely on the formation of a connected <biotin:(strept)avidin> binding pair during the course of the assay.

In the field of nucleic acid analysis the technique of sequence capture has been established. In specific embodiments biotinylated single-stranded nucleic acids are attached to magnetic particles coated with (strept)avidin. These particles can be used for 'fishing' desired sequences, e.g. for further amplification or for sequencing. Mastrangeli R et al. (Analytical biochemistry 241 (1996) 93-102) disclose capture of cDNA sequences of interest with a biotinylated probe and streptavidin-coupled magnetic beads, followed by PCR amplification of the captured molecules. However, despite knowledge and availability of sequence capture no progress seems to have been made with regards to alternative coating technologies to attach binding partners other than (strept) avidin to solid phases, specifically for routine use in detection assays such as immunoassays. One reason could be that a number of sample materials are known to contain nucleolytic enzymes which discourage the use of hybridizing nucleic acids as candidate binding pairs to replace biotin:(strept)avidin.

Single-stranded oligonucleotides with complementary sequences, i.e. oligonucleotides capable of forming a duplex by way of hybridization have been proposed earlier as binding pair means to connect macromolecules or to attach molecules to a solid phase. EP 0488152 discloses a heterogeneous immunoassay with a solid phase on which an analyte-specific capture antibody is immobilized by a nucleic acid duplex which connects the antibody and the solid phase. An embodiment is shown where one hybridized oligonucleotide is bound to the antibody and the complementary oligonucleotide is bound to the solid phase, thereby forming a connecting duplex. Similar disclosures are provided in the documents EP 0698792, WO 1995/024649, WO 1998/029736, and EP 0905517. WO 2013/188756 discloses methods of flow cytometry and a composition comprising an antibody conjugated to a first oligonucleotide, an oligosphere conjugated to a second oligonucleotide having a sequence identical to that of the first oligonucleotide, and an oligonucleotide probe with a label and a third sequence that is complementary to the first and the second oligonucleotides. In a specific embodiment the oligosphere is magnetic. The document reports specific uses of oligospheres as references in standardization procedures.

Modified oligonucleotides such as peptide nucleic acid (PNA) and locked nucleic acid (LNA) have been explored for biochemical and physiological applications. LNA possesses a methylene linker between the 2'-oxygen and 4'-carbon atom of the ribose moiety that consequently locks the sugar into a C3-endo conformation, hence the name "locked nucleic acid". This chemical modification confers nuclease resistance as well as higher affinity and greater specificity for oligonucleotide targets in technical applications involving duplex formation by hybridization. WO 1998/39352 discloses locked nucleic acid (LNA) structures. WO 2000/056746 discloses synthesis of LNA monomers including intermediate products for certain stereoisomers of LNA. By way of chemical synthesis, single strands consisting of LNA nucleoside analog monomers only ("all-LNA") can be synthesized.

WO 1999/14226 suggests the use of LNA in the construction of affinity pairs for attachment to molecules of interest and solid supports. However it is also known to the art that hybridization of complementary all-LNA single strands poses technical problems. Thermodynamic analysis of hybridization of oligonucleotide analogues consisting only of LNA is largely empirical, and sequence prediction of hybridizing monomers without a prior denaturation step (e.g. heating prior to hybridization) does not appear to be possible, so far.

For the most part, mixed LNA/DNA oligonucleotides (also referred to as "mixmer single strands" or "mixmers") were analyzed, so far. Fewer reports of the characterization of hybridizing single-stranded oligonucleotides made exclusively from LNA monomers (i.e. "all-LNA" single-stranded oligonucleotides) were published, so far, particularly by Koshkin A. A. et al. (J Am Chem Soc 120 (1998) 13252-13253) and Möhrle B. P. et al. (Analyst 130 (2005) 1634-1638). Eze N. A. et al. (Biomacromolecules 18 (2017) 1086-1096) report association rates from DNA/LNA mixmers and DNA probes to be below $10^5$ $M^{-1}$ $s^{-1}$. According to these authors, the hybridization kinetics in solution does not seem to be affected by substituting one or more DNA monomers with LNA monomers, considering one third of monomers available for substitution.

Predictions concerning thermodynamic behavior of LNA-containing oligonucleotides are aided by dedicated computer programs referred to by Tolstrup N. et al. (Nucleic Acids Research 31 (2003) 3758-3762). However, this report explicitly mentions a higher prediction error for LNA oligonucleotides due to the more complex properties of these oligonucleotides, rather than lack of experimental data.

The important underlying concept of the present report is that the skilled person can continue to use the established (strept)avidin-coated solid phases when one member of an alternative binding pair is attached as a biotin conjugate. That is to say, the present disclosure teaches to attach a selected member of an alternative binding pair onto a streptavidin-coated solid phase of choice, wherein the selected member of the alternative binding pair is in biotinylated form. It is recalled that the selected member itself must neither be biotin nor (strept)avidin. The present report thus discloses "overcoating" of (strept)avidin-coated solid phases with a selected member of an alternative binding pair. Such an overcoated solid phase can be used for non-covalently and specifically attaching a compound to the solid phase, wherein the compound is provided as a conjugate with the other member of the alternative binding pair. Attachment is effected by the two members of the alternative binding pair binding to each other.

Further, it was found and is reported herein, that biotinylation of a selected member of a binding pair other than the <biotin:(strept)avidin> binding pair can be practiced easily, mostly by relying on established biotin-coupling chemistries, while preserving the member's function in forming a connection with its respective cognate binding member.

SUMMARY OF THE INVENTION

The concept of overcoating provides a first aspect of the present disclosure. Accordingly, the first aspect which relates to all other aspects and embodiments as disclosed herein relates to a solid phase coated with (strept)avidin and having attached thereto, by way of <biotin:(strept)avidin> interaction, a biotinylated first member of a binding pair, wherein the attached first member is capable of binding to a second member of the binding pair, the second member being part of a conjugate, but wherein the first member is not capable of binding to biotin or to (strept)avidin, wherein the second member which is capable of becoming and/or being bound by the first member is part of a conjugate. The conjugate comprising any of an analyte, an analyte analogon, and an analyte-specific capturing agent, and wherein no member of the binding pair is capable of hybridizing with a naturally-occurring single-stranded nucleic acid. Thus, the first aspect includes a solid phase coated with (strept)avidin and having attached thereto, by way of <biotin:(strept) avidin> interaction, a biotinylated first member of a binding pair, wherein the attached first member is capable of binding to a second member of the binding pair, but is not capable of binding to biotin or to (strept)avidin, wherein the second member is capable of becoming bound by the first member when the second member is part of a conjugate comprising any of an analyte, an analyte analogon, and an analyte-specific capturing agent, and wherein no member of the binding pair is capable of hybridizing with a naturally-occurring single-stranded nucleic acid.

The solid phase according to this first aspect is obtainable and/or obtained from a method of preparing a solid phase having attached thereto a member of a binding pair, the method being another aspect which relates to all other aspects and embodiments as disclosed herein. Thus, disclosed is a method of preparing a solid phase having attached thereto a member of a binding pair, the method comprising the steps of (a) providing a solid phase coated with (strept)avidin;
(b) selecting a binding pair with a first member and a second member;
(c) providing the first member of the binding pair selected in step (b);
(d) biotinylating the first member of step (c);
(e) attaching the biotinylated first member obtained from step (d) to the solid phase of step (a) by contacting the biotinylated first member with the coated solid phase and incubating, thereby attaching the biotinylated first member to the solid phase by way of biotin-(strept)avidin interaction;

wherein in step (b) the pair is selected such that without biotinylation the first and the second member of the binding pair are not capable of binding to streptavidin, in biotinylated form and attached to the coated solid phase the first member of the binding pair is capable of binding to the second member, and no member of the binding pair is capable of hybridizing with a naturally-occurring single-stranded nucleic acid;

thereby obtaining the solid phase having attached thereto the member of the binding pair. This method of preparing the solid phase by overcoating is another aspect of the present disclosure which relates to all other aspects and embodiments as disclosed herein. Thus, this aspect includes a method of preparing a solid phase having attached thereto a member of a binding pair, the method comprising the steps of (a) providing a solid phase coated with (strept)avidin;
(b) selecting a binding pair with a first member and a second member;
(c) providing the first member of the binding pair selected in step (b);
(d) biotinylating the first member of step (c);
(e) attaching the biotinylated first member obtained from step (d) to the solid phase of step (a) by contacting the biotinylated first member with the coated solid phase and incubating, thereby attaching the biotinylated first member to the solid phase by way of biotin-(strept)avidin interaction;

wherein in step (b) the pair is selected such that without biotinylation the first and the second member of the binding pair are not capable of binding to streptavidin, in biotinylated form and non-covalently attached to the coated solid phase by way of a biotin:(strept)avidin bond the first member of the binding pair is capable of binding to the second member, in conjugated form and covalently attached to an analyte-specific capturing agent the second member of the binding pair is capable of binding to the biotinylated first member attached to the solid phase, and no member of the binding pair is capable of hybridizing with a naturally-occurring single-stranded nucleic acid;

thereby obtaining the solid phase having attached thereto the member of the binding pair.

A further aspect of the present disclosure which relates to all other aspects and embodiments as disclosed herein is the use of a solid phase as disclosed herein or of a solid phase obtained (as a product) from a method of preparing the solid phase as disclosed herein, in an assay to determine an analyte in a sample.

Yet, a further aspect of the present disclosure which relates to all other aspects and embodiments as disclosed herein is a kit for determining an analyte in a sample, the kit comprising (a) in a first container, and either (b) or (c) in a second container, wherein (a) is a solid phase having attached thereto a first member of a binding pair, wherein the solid phase is a solid phase as disclosed herein or a solid phase obtained from the method of preparing the solid phase as disclosed herein,
(b) is a first conjugate, the conjugate comprising a second member of the binding pair coupled to a capturing agent specific for the analyte (i.e. the agent being an analyte-specific capturing agent),
(c) is a second conjugate, the conjugate comprising a second member of the binding pair coupled to the analyte or an analogon of the analyte.

Yet, a further aspect of the present disclosure which relates to all other aspects and embodiments as disclosed herein is a complex comprising (a) and either (b) or (c), wherein (a) is a solid phase having attached thereto a first member of a binding pair, wherein the solid phase is a solid phase as disclosed herein or a solid phase obtained from the method of preparing the solid phase as disclosed herein,
(b) is a first conjugate, the conjugate comprising a second member of the binding pair coupled to a capturing agent specific for the analyte (i.e. the agent being an analyte-specific capturing agent),
(c) is a second conjugate, the conjugate comprising a second member of the binding pair coupled to the analyte or an analogon of the analyte, wherein in the complex (a) is bound to (b) or (c), respectively, wherein in the complex a first member of the binding pair is bound to a second member of the binding pair.

Yet, a further aspect of the present disclosure which relates to all other aspects and embodiments as disclosed herein is a method to form a complex as disclosed herein, the method comprising the step of contacting (a) with either (b) or (c), wherein (a) is a solid phase having attached thereto a first member of a binding pair, wherein the solid phase is a solid phase as disclosed herein or a solid phase obtained from the method of preparing the solid phase as disclosed herein, (b) is a first conjugate, the conjugate comprising a second member of the binding pair coupled to a capturing agent specific for the analyte (i.e. the agent being an analyte-specific capturing agent),
(c) is a second conjugate, the conjugate comprising a second member of the binding pair coupled to the analyte or an analogon of the analyte, followed by the step of incubating (a) and either (b) or (c), respectively, thereby forming the complex, wherein in the complex (a) is bound to (b) or (c), respectively, wherein in the complex a first member of the binding pair is bound to a second member of the binding pair.

Yet, a further aspect of the present disclosure which relates to all other aspects and embodiments as disclosed herein is a method to determine an analyte in a sample, the method comprising the steps of (a) providing the sample with the analyte;
(b) providing a solid phase having attached thereto a first member of a binding pair, wherein the solid phase is a solid phase as disclosed herein or a solid phase obtained from the method of preparing the solid phase as disclosed herein;
(c) providing a conjugate, the conjugate comprising a second member of the binding pair coupled to a capturing agent specific for the analyte (i.e. the agent being an analyte-specific capturing agent);
(d) contacting, mixing and incubating the sample of (a) with conjugate of (c), thereby forming a complex, the complex comprising the analyte being captured by the analyte-specific capturing agent comprised in the conjugate;
(e) immobilizing complex formed in step (d) by contacting and incubating complex with the solid phase of step (b), wherein the first member of the binding pair binds to the second member;
(f) optionally washing immobilized complex obtained from step (e);
(g) determining analyte comprised in immobilized complex obtained from step (e) or (f);

thereby determining the analyte in the sample.

Yet, a further aspect of the present disclosure which relates to all other aspects and embodiments as disclosed herein is a method to determine an analyte in a sample, the method comprising the steps of (a) providing the sample with the analyte;
(b) providing a solid phase having attached thereto a first member of a binding pair, wherein the solid phase is a solid phase as disclosed herein or a solid phase obtained from the method of preparing the solid phase as disclosed herein;
(c) providing a conjugate, the conjugate comprising a second member of the binding pair coupled to the analyte or an analogon of the analyte;
(d) providing a labeled analyte-specific detecting agent, wherein the analyte or analyte analogon comprised in the conjugate of step (c) and the analyte in the sample are capable of being bound by the detecting agent;
(e) contacting, mixing and incubating the sample of step (a) with conjugate of step (c) and detecting agent of step (d), thereby forming a first complex comprising the analyte and the detecting agent and a second complex comprising the conjugate and the detecting agent;
(f) immobilizing second complex formed in step (e) by contacting and incubating complex with the solid phase of step (b), wherein the first member of the binding pair binds to the second member;
(g) optionally washing the immobilized complex obtained from step (f);
(h) determining label comprised in the immobilized complex obtained from step (f) or (g);

thereby determining the analyte in the sample.

DETAILED DESCRIPTION OF THE INVENTION

The terminology used herein is for the purpose of describing particular embodiments only and is not intended to be limiting of the invention.

The articles "a" and "an" are used herein to refer to one or to more than one (i.e., to at least one) of the grammatical object of the article. By way of example, "an item" means one item (one single item) or more than one item (a plurality of the item).

It is further understood that the root terms "include" and/or "have", when used in this specification, specify the presence of stated features, items, integers, steps, operations, elements, and/or components, but do not preclude the presence or addition of at least one other feature, integer, step, operation, element, component, and/or groups thereof. In an analogous way, "with" also specify the presence of stated features, etc.

As used herein, the terms "comprises," "comprising,", "contains", "containing", "includes," "including," "has," "having" or any other variation thereof, are intended to cover a non-exclusive inclusion, i.e. indicate an open list of features. For example, a process, method, article, or apparatus that comprises a list of features is not necessarily limited only to those features but may include other features not expressly listed or inherent to such process, method, article, or apparatus. In contrast, "consists of", "consisting of" or any other variation thereof specify a closed list of features. Notably, the closed list of given features is understood as representing a specific embodiment of an open list of these features.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially", "relatively", "generally", "typically", "about", and "approximately" are relative modifiers intended to indicate permissible variation from the characteristic so modified. They are not intended to be limited to the absolute value or characteristic which it modifies but rather approaching or approximating such a physical or functional characteristic. If not stated otherwise, it is understood that the term "about" in combination with a numerical value n ("about n") indicates a value x in the interval given by the numerical value±5% of the value, i.e. $n-0.05*n \leq x \leq n+0.05*n$. In case the term "about" in combination with a numerical value n describes a preferred embodiment of the invention, the value of n is most preferred, if not indicated otherwise.

In this detailed description, references to "one embodiment", "an embodiment", or "in embodiments" mean that the feature being referred to is included in at least one embodiment of the technology with regards to all its aspects according to present disclosure. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the technology in all its aspects according to present disclosure can include any variety of combinations and/or integrations of the embodiments described herein.

In all aspects and embodiments mentioned herein, the term "(strept)avidin" and avidin-type protein can be used interchangeably. An avidin-type protein is generally understood as a protein with at least one binding pocket capable of binding specifically to the heterocyclic structure of biotin which is represented by the ureido ring that is fused with the tetrahydrothiophene ring. By virtue of this property, an avidin-type protein is capable of binding to a biotinylated target molecule, wherein biotin is covalently bound to the molecule via the carbon atom of the carboxyl function of the Valeric acid side chain of biotin. Several embodiments of avidin-type proteins are known to the art. More specifically, an avidin-type protein can be selected from the group including avidin, neutravidin, streptavidin, bradavidin, traptavidin, a biotin-binding variant thereof, a mixture thereof, a monomer, dimer, trimer, tetramer or multimer thereof, a conjugated form thereof and an antibody binding to a conventionally biotinylated molecule of interest. It is known that in their naturally occurring forms a number of avidin-type proteins (especially those which are not antibodies), specifically avidin and streptavidin, are homotetramers; i.e. they consist of four identical subunits. In an embodiment of a variant of a monomeric avidin-type protein, the naturally occurring form may be a di- tri-, or tetra-oligomer with each monomer having a biotin binding pocket. In an embodiment the avidin-type protein is selected from a monomer, a homodimer, a homotrimer, and a homotetramer. Also, an avidin-type protein can be an antibody with an antigen binding pocket capable of binding specifically to the heterocyclic structure of biotin that is represented by the ureido ring that is fused with the tetrahydrothiophene ring.

The interaction between streptavidin and biotin constitutes an example of exceptionally strong protein:ligand binding. Streptavidin binding kinetics have been characterized in much detail, e.g. as reported by Srisa-Art M. et al. (Anal. Chem. 80 (2008) 7063-7067) and references cited therein. Accordingly, the association rate of streptavidin and biotin is about $10^7$ $M^{-1}$ $s^{-1}$ with an exemplary range of about $2\times10^6$ $M^{-1}$ $s^{-1}$ to about $5\times10^7$ $M^{-1}$ $s^{-1}$ which depends on the particular technical approach towards individual measurement. The dissociation rate constant of $2.4\times10^{-6}$ $s^{-1}$ was reported for underivatized streptavidin, which was 30-fold higher than the value of $7.5\times10^{-8}$ $s^{-1}$ observed with avidin, see Piran U & Riordan W J J (Immunol 1 Methods 133 (1990) 141-143).

When referring to "(strept)avidin" or an avidin-type protein in the present disclosure, it is understood that these terms equally incorporate any variant thereof with the proviso that the variant is capable of binding biotin non-covalently with at least one binding pocket capable of binding specifically to the heterocyclic structure of biotin that is represented by the ureido ring that is fused with the tetrahydrothiophene ring. In this respect, a variant is a "functionally equivalent polypeptide" in that the amino acids forming the at least one binding pocket bear similar electrostatic and stereochemical attributes of the amino acid sequence of the original avidin-type protein under consideration, wherein the variant comprises one or more conservative amino acid substitutions, analog amino acids substitutions and/or deletions and/or additions of amino acids that do not significantly affect or alter the function of the amino acids of the binding pocket. "Functionally equivalent" also includes a homologous amino acid sequence with regards to the respective referenced amino acid sequence.

For the purpose of the present disclosure it is understood that the term "biotin" denotes the naturally occurring compound, i.e. D(+)-biotin. Biotin (D(+)-biotin; $C_{10}H_{16}N_2O_3S$; MW=244.31 g/mol; IUPAC name: 5-[(3aS,4S,6aR)-2-oxo-1,3,3a,4,6,6a-hexahydrothieno[3,4-d]imidazol-4-yl]pentanoic acid), CAS Registry Number 58-85-5 comprises a ureido ring fused with a tetrahydrothiophene ring, and a Valeric acid substituent which is covalently attached to one of the carbon atoms of the tetrahydrothiophene ring. The basic structure of biotin is known since long and was reported e.g. by Melville D. B. et al. (J. Biol. Chem. 146 (1942) 487-492). Biotin has three contiguous chiral carbon atoms and therefore, four diastereomeric racemic forms are possible. Of the diastereomeric racemic forms, only D(+)-biotin occurs in nature whereas other isomers are of synthetic origin. The biologically active form is the (3aS,4S,6aR) configuration.

According to Marquet A. (Pure & Appl. Chem. 49 (1977) 183-196), in the crystal structure of D(+)-biotin the ureido ring is planar while the thiophane ring has an envelope conformation. The Valeric acid side chain is not fully extended but twisted, and there is interaction between the $C_6$ atom of the side chain and the $N'_3$ atom of the ureido ring; reportedly this interaction has an impact on the reactivity of biotin. The envelope conformation of the thiophane ring was also reported in solution, as shown by NMR studies reported by Glasel J. A. (Biochemistry 5 (1966) 1851-1855) and by Lett R. & Marquet A./Tetrahedron 30 (1974) 3365-3377).

The term "biotin moiety" is used to refer to the biotin-related part or biotin-derived part of a molecule as e.g. obtained from any kind of biotinylation or chemical coupling. The attachment of biotin to an appropriate chemical group on a molecule of interest via the carbon atom of the carboxyl function of the Valeric acid side chain is referred to as "biotinylation" or "conventional biotinylation". Accordingly, the biotin moiety of a "biotinylated" molecule of interest has an outward-facing ring structure (i.e. the ureido ring that is fused with a tetrahydrothiophene ring), whereas the linear portion of the biotin moiety is inward-facing, towards the surface of the biotinylated molecule. The outward-facing ring structure can be bound by an avidin-type protein. After biotinylation the biotin moiety preserves the capability to interact specifically with (strept)avidin; biotinylation does not affect the part of the biotin molecule that is responsible for specific interaction with the binding pocket of avidin-type proteins, i.e. biotinylation does not affect the heterocyclic structure represented by the ureido ring that is fused with the tetrahydrothiophene ring.

Of note, biotin derivatives such as, but not limited to, biotinol or biocytin also have the capability of binding to (strept)avidin, in a similar way as biotin. This is because in such molecules the tetrahydrothiophene ring is either completely preserved (as is the case for biotinol and biocytin, or the heterocyclic structure is sufficiently preserved to still allow for substantial interaction with a (strept)avidin binding pocket.

The term "biotinylation" in the context of the present disclosure encompasses different kinds of linker chemistries capable of coupling biotin to a molecule of choice, provided that the ureido ring that is fused with a tetrahydrothiophene ring is presented outwardly from the biotinylated molecule, such that the biotin moiety can be bound by (strept)avidin. The skilled person is well aware of different kinds of linker compounds capable of bridging from the carbon atom of the Valeric acid moiety of biotin to a functional group comprised in the molecule of choice.

Throughout this document between a first and a second member of a binding pair the punctuation mark (":") is used to denote the specific connection, or the capability to form such a specific connection, of a first member and a second member of a binding pair, thus being represented by "member1:member2" or "<member1:member2>". Typically, the first and the second member belong to different species, i.e. first member and the second member are not identical compounds. Accordingly, depending on context, "member1:member2" can mean that member 1 and member 2 can form a binding pair, and that member1 is capable of specifically recognizing and bind to member 2; or, depending on context, "member1:member2" can mean that member1 and member2 are a connected pair. It is also understood that unless specifically described differently, a member includes not only the member as an isolated compound but also the member being attached to another entity, e.g. forming a moiety of the other entity. By way of example, the "(strept)avidin:biotin" (="biotin:(strept)avidin") binding pair is perfectly known to the person skilled in the art. A biotin or a biotin moiety on the one hand and (strept)avidin on the other hand represent the two members of this binding pair. As described elsewhere, this binding pair is outstanding in having one of the highest binding affinities known for non-covalent interactions. The "biotin" in the term "biotin:(strept)avidin" includes free biotin, biotin derivatized at the carbon atom of the carboxyl function of the Valeric acid side chain of biotin, and the biotin moiety of a biotinylated compound. The "(strept)avidin" in the term "biotin:(strept)avidin" includes isolated (strept)avidin and (strept)avidin that is covalently or non-covalently attached to another entity, e.g. to a solid phase.

The term "analyte-specific binding" as used in the exemplary context of an antibody refers to the immunospecific interaction of the antibody with its target epitope on the analyte, i.e. the binding of the antibody to the epitope on the analyte. The concept of analyte-specific binding of an antibody via its epitope on an analyte is fully clear to the person skilled in the art. The terms "specific capturing agent" and "specific detecting agent" are both embodiments under the broader term "specific binding agent". This indicates that a subject agent is able to either specifically bind to or to be specifically bound by an analyte of interest. Many different assay set-ups for immunoassays are known in the art. Dependent on the specific assay set-up, various specific binding agents can be used. The term "analyte-specific binding agent" encompasses the terms "analyte-specific capturing agent" and "analyte-specific detecting agent"; it refers to a molecule specifically binding to the analyte of interest. An analyte-specific binding agent in the sense of the present disclosure typically comprises binding or capture molecules capable of binding to an analyte (other terms: analyte of interest, target molecule). In one embodiment the analyte-specific binding agent has at least an affinity of $10^7$ l/mol for its corresponding target molecule, i.e. the analyte. The analyte-specific binding agent in other embodiments has an affinity of $10^8$ l/mol or even of $10^9$ l/mol for its target molecule. As the skilled artisan will appreciate the term specific is used to indicate that other biomolecules present in the sample do not significantly bind to the binding agent specific for the analyte. In some embodiments, the level of binding to a biomolecule other than the target molecule results in a binding affinity which is only 10%, more preferably only 5% of the affinity of the target molecule or less. In one embodiment no binding affinity to other molecules than to the analyte is measurable. In one embodiment the analyte-specific binding agent will fulfill both the above minimum criteria for affinity as well as for specificity.

The term "antibody" encompasses the various forms of antibody structures including, but not being limited to, whole antibodies and antibody fragments. In an embodiment the antibody can be of different origin, e.g. from goat, sheep, mouse, rabbit, or rat; the antibody can be a chimeric antibody, or a further genetically engineered antibody as long as the characteristic properties according to the embodiment in the present disclosure are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to IGF-1, namely being able to assemble together with a $V_H$ domain to a functional antigen binding site and thereby providing the properties of an antibody conforming with the technology according to present disclosure. "Antibody fragments" comprise a portion of an intact antibody, preferably comprising the antigen-binding region thereof. Examples of antibody fragments include Fab, Fab', $F(ab')_2$, and Fv fragments; single-chain antibody molecules; scFv, sc(Fv)2; diabodies; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species (sc(Fv)2). It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The present disclosure includes monovalent Fab fragments and single chain Fv that are derived from monoclonal antibodies capable of specifically binding free biotin as disclosed in here. Compared with naturally occurring antibody forms the monovalent species can diffuse faster in aqueous solution, owing to their smaller molecular weight. Another aspect is that under suitable conditions particularly scFv antibodies can be recombinantly produced in prokaryotic expression systems.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404097; WO 1993/01161; Hudson et al., *Nat. Med.* 9:129-134 (2003); and Holliger et al., *PNAS USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained from a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of the technology according to present disclosure. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein., Nature, 256: 495-97 (1975); Hongo et al., Hybridoma, 14 (3): 253-260 (1995), Harlow et al., Antibodies: A Laboratory Manual, (Cold Spring Harbor Laboratory Press, $2^{nd}$ ed. 1988); Haemmerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., PNAS USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., PNAS USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

The term "peptide" means any compound formed by the linkage of two or more amino acids by amide (peptide) bonds, usually a polymer of $\alpha$-amino acids in which the $\alpha$-amino group of each amino acid residue (except the $NH_2$-terminal) is linked to the $\alpha$-carboxyl group of the next residue in a linear chain. The terms peptide, polypeptide and poly(amino acid) are used synonymously herein to refer to this class of compounds without restriction as to size. The largest members of this class are referred to as proteins.

The terms "immunogen" (="antigen") and "immunogenic" refer to substances capable of producing or generating an immune response in an organism. In contrast, "haptens" are small molecules (e.g. pesticides, fungicides, drugs, hormones, toxins, synthetic peptides, etc.) which do not directly induce an immune response such as formation of antibodies. Techniques have been established to raise antibodies against haptens by conjugating them with immunogenic carriers, such as antigenic macromolecules. For the purpose of the present disclosure, a hapten is understood as being a low molecular weight molecule, specifically having a molecular weight of 10,000 Da or less, which does not elicit immune response until and unless conjugated with an immunogenic carrier, such as protein. Once an immune response is elicited and an antibody is formed, the antibody can bind to the hapten. Antibodies thus generated are useful in many fields, specifically in the development of immunodiagnostic kits or biosensors. Thus, the term "hapten" denotes a small molecule of 10,000 Da or less that can elicit an immune response only when attached to an immunogenic carrier such as a polypeptide of at least 30 amino acids. In this sense, and in an embodiment, a hapten is an incomplete antigen that cannot, by itself, promote antibody formation but that can do so when conjugated to a protein of at least 30 amino acids. Exemplary haptens are aniline, o-, m-, and p-aminobenzoic acid, quinone, histamine-succinyl-glycine (HSG), hydralazine, halothane, Indium-DTPA, fluorescein, digoxigenin, theophylline, bromodeoxyuridine, steroid compounds and dinitrophenol. In a specific embodiment, the hapten is not biotin and does not contain a biotin moiety. In one specific embodiment the hapten is digoxigenin or theophylline or fluorescein or bromodeoxyuridine.

The term "analyte" refers to the substance, or group of substances, whose presence or amount thereof in a sample is to be determined including, but not limited to, any drug or drug derivative, hormone, peptide or protein antigen, DNA or RNA oligonucleotide, hapten, or hapten-carrier complex.

An "analyte analogon" (="analogon of the analyte") is any substance, or group of substances, which behaves in a similar manner to the analyte, or in a manner conducive to achieving a desired specific binding and/or assay result with respect to binding affinity and/or specificity of the analyte-specific binding agent (e.g. antibody) for the analyte including, but not limited to, derivatives, metabolites, and isomers thereof.

The term "sample" denotes an aqueous mixture such as a body fluid from a host, for example, urine, whole blood, plasma, serum, saliva, semen, stool, sputum, cerebral spinal fluid, tears, mucus or the like, but in particular is urine, plasma or serum. The sample can be pretreated if desired and can be prepared in any convenient medium that does not interfere with an assay which makes use of an analyte-specific binding agent. An aqueous medium is preferred. In the sense of this disclosure, a sample is generally understood as being physically separated from the source individual.

A "mixture" is a substance made by combining two or more different materials with no chemical reaction occurring. Mixtures are the product of a mechanical blending or "mixing" of chemical substances like elements and compounds. Unless specified differerently, forming a mixture does not imply covalent chemical bonding or other chemical change of the materials being mixed, so that each ingredient retains its own chemical properties and makeup. While there are no chemical changes in a mixture, physical properties of a mixture, such as its melting point, may differ from those of its components.

A "conjugate" refers to a compound formed by covalently joining of two or more chemical compounds. This process is also referred to as "conjugation". Typically, but not necessarily, the two or more chemical compounds are joined by an at least bifunctional linker, wherein a first covalent bond is formed between a first reactive group of the linker and the first chemical compound, and a second covalent bond is formed between the second reactive group of the linker and the second chemical compound. The term "covalent bond" means a chemical bond between two species, and may involve single bonds or multiple bonds. In contrast, the term "non-covalent bond" means chemical or physical interactions that do not form chemical bonds. Non-covalent bonding thus includes hydrophobic/hydrophilic interactions, Hydrogen-bonding, van der Waals interactions, and ionic and metallic interactions. For example, adsorption of a substance to a surface is non-covalent, whereas coupling of a substance to a surface, such as through e.g. carbodiimide, N-hydroxy succinimide (NHS) or so-called "click" chemistry coupling, is covalent.

The term "binding partner" or "binding pair" is a reference to complementary molecules, a first member and a second member, the pair of which can also be denoted as member1:member2, [first member]:[second member], member1:[second member], or [first member]:member2, wherein the different members specifically interact with each other via a non-covalent attachment determined by their structure. Exemplary binding partners include a pair of hybridizing oligo- or polynucleotides or analogs thereof capable of forming with each other a duplex, biotin:(strept)avidin, antibody:hapten, antibody:antigen, enzyme:substrate, [mannose, maltose, amylose]:[respective sugar-binding protein], [oligo- or polysaccharide]:lectin, cytokine:[respective receptor] or ligand:[respective ligand-binding domain], [$Zn^{2+}$ $Ni^{2+}$, $Co^{2+}$, or $Cu^{2+}$ metal-chelate complex]:[histidine-tag], [indium chelate complex]:[CHA255 antibody], [cucurbit[n]uril host residue]:[guest residue], [first protein dimerization domain]:[second protein dimerization domain].

A "label" is defined as a moiety that generates a detectable signal either directly or indirectly, for example, on addition of a reactant thereto or therewith, such as, an enzyme label which generates a detectable signal with the addition of a suitable co-reactant/substrate, which when acted with or by the enzyme, yields the detectable signal. The label can be detectable per se, such as visually with the unaided eye or using a visualizing device, such as a microscope, a spectrophotometer, a colorimeter and so on. Hence, such a label can include, for example, an enzyme, a ferritin, a fluorescent or colored microparticle/bead or nanoparticle/bead, a colloid metal, including gold and silver colloidal particles, a quantum dot, a magnetic particle, an up-converting phosphorescent particle, an electrochemiluminescent molecule, compounds containing various metals, including, but not limited to, transition metals, such as Sc, Y, Ti, Zr, Hf, V, Nb, Ta, Cr, Mo, W, Mn, Tc, Re, Fe, Ru, Co, Rh, Ir, Ni, Pd, Pt, Cu, Ag, Au, Zn, Cd, Hg and Os; Lanthanide series elements, such as Ce, Pr, Nd, Pm, Sm, Eu, Gd, Tb, Dy, Ho, Er, Tm, Yb and Lu; Actinide series elements, such as, Th, Pa, U, Np, Pu, Am, Cm, Bk, Cf, Es, Fm, Md, No and Lr; and so on.

As used herein, the terms "solid phase" and "solid phase support" are used interchangeably, and refer to any solid or semi-solid material to which a member of a binding pair can be attached, e.g., a material to which the member of a binding pair can be attached noncovalently, either directly or indirectly, or a material in which they can be incorporated (e.g., physical entrapment, adsorption, etc.), or a material which can be functionalized to include (e.g., to associate with) the member of the binding pair. In addition to member of the binding pair, a solid phase support can contain a variety of materials including, e.g., a natural or synthetic polymer, resin, metal, or silicate. Importantly in the sense of the present disclosure, the outward-facing surface of the solid phase is coated with (strept)avidin, thereby allowing attachment of a biotinylated member of a binding pair by way of <biotin:(strept)avidin> interaction.

Suitable solid phase supports are known in the art and illustratively include agaroses (commercially available as Sepharose), celluloses (e.g., a carboxymethyl cellulose), dextrans, (such as Sephadex), polyacrylamides, polystyrenes, polyethylene glycols, silicates, divinylbenzenes, methacrylates, polymethacrylates, glass, ceramics, papers, metals, metalloids, polyacryloylmorpholides, polyamides, poly(tetrafluoroethylenes), polyethylenes, polypropylenes, poly(4-methylbutenes), poly(ethylene terephthalates), rayons, nylons, poly(vinyl butyrates), polyvinylidene difluorides (PVDF), silicones, polyformaldehydes, cellulose acetates, nitrocelluloses, other types of resins, or combinations of two or more of any of the foregoing. All that is required is that the material or combination of materials in the solid phase support not substantially interfere, e.g., in some cases only minimally interfere, with the binding between the members of a binding pair.

A solid phase support can have a variety of physical formats, which can include for example, a membrane; a chip; a slide (e.g., a glass slide or coverslip); a column; a hollow, solid, semi-solid, pore or cavity containing particle such as a bead; a gel; a fiber including a fiber optic material; a matrix; and a sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, multiwell or microwell plate, and the like. A particle to which a member of a binding pair is attached can have a variety of sizes, including particles that remain suspended in a solution of desired viscosity, as well as particles that readily precipitate in a solution of desired viscosity. Particles can be selected for ease of separation from sample constituents, for example, by including purification tags for separation with a suitable tag-binding material, magnetic, paramagnetic or superparamagnetic properties for separation or retention methods which are using a magnetic field, and the like.

In a specific embodiment, a solid phase particle described herein has a spherical shape. However, a particle can be, e.g., oblong or tube-like. In some embodiments, e.g., a crystalline form particle, the particle can have polyhedral shape (irregular or regular), such as a cube shape. In some embodiments, a particle can be amorphous.

In some embodiments, a particle mixture can be substantially spherical, substantially oblong, substantially tube-like, substantially polyhedral, or substantially amorphous. In this regard, by "substantially" is meant that the particle mixture is more than 30 (e.g., 35, 40, 45, 50, 55, 60, 65, 70, 75, 80, 85, 90, 95, 96, 97, 98, or 99 or more) % of a given shape.

In some embodiments, the diameter (or longest straight dimension) of the particle can be between about 1 nm to about 1000 μm or larger. In an embodiment, a particle can be at least about 1 nm to about 500 μm. In some embodiments, a particle can be from about 50 nm to about 200 μm in diameter (or at its longest straight dimension).

The solid phase can be coated with (strept)avidin in a number of ways known to those having ordinary skill in the art. For example, (strept)avidin can be covalently or noncovalently bound to a solid-phase support, either directly or indirectly, such as through a linker, binding agent, or member of a binding pair. For example, (strept)avidin can be directly covalently bound to a solid phase support, e.g., through a chemical bond between a functional group on the (strept)avidin and a functional group on the solid phase surface. Alternatively, (strept)avidin can be indirectly covalently bound to a solid-phase surface, e.g., (strept)avidin can be covalently bound to a linker, binding agent or "undercoating" compound, which itself is covalently bound to the solid phase surface. In the latter case, in an embodiment the solid phase surface is covalently or non covalently coated with an undercoating compound such as, but not limited to, serum albumin, and in a subsequent step (strept)avidin is "overcoated" by binding covalently or non covalently the (strept)avidin to the undercoating compound.

In a frequently used embodiment, (strept)avidin can be noncovalently bound to a solid phase, such as through adsorption to or coating on the solid phase surface, or through covalent or noncovalent association with a linker, binding agent, or member of a binding pair, which itself is noncovalently bound or associated with the solid phase. Illustrative examples of linkers, binding agents, or members of binding pairs useful for association of (strept)avidin to a support include proteins, organic polymers (PEG and derivatives thereof), and small molecules. Particular preferred examples include HSA (human serum albumin), BSA (bovine serum albumin), and biotin.

For example, in one preferred embodiment, (strept)avidin can be covalently conjugated to a binding agent such as HSA or BSA, and then the resulting covalent conjugate can be used to noncovalently coat the surface of a solid phase. In another embodiment, (strept)avidin can be noncovalently attached to (e.g., coated on) a solid phase surface. In other embodiments, a conjugate of (strept)avidin with one member of a binding pair can bind noncovalently to the other member of the binding pair, which has been covalently linked to the solid phase.

In some embodiments, (strept)avidin is directly noncovalently bound to a solid phase surface, e.g., noncovalent adsorption of the (strept)avidin on the solid phase support. In other embodiments, (strept)avidin is indirectly noncovalently bound to a solid phase surface. In an embodiment, (strept)avidin is covalently bound to a linker, binding agent, or member of a binding pair, which noncovalently associates with the solid phase surface. In all cases, binding of (strept) avidin with a solid phase should not substantially affect the specificity of a biotinylated member with regard to the desired <biotin:(strept)avidin> interaction for attaching the member, as compared to the specificity for the (strept)avidin when it is not associated with a solid phase.

A variety of chemical reactions useful for covalently binding (strept)avidin to a solid phase surface are well known to those skilled in the art. Illustrative examples of functional groups useful for covalent attachment to such a support include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity.

Linkers or binding agents can also be useful to covalently link (strept)avidin to a solid phase surface. For example, a covalent conjugate of an analyte with a binding agent such as HSA or BSA can be covalently linked to the solid phase surface.

In some embodiments, the surface of the solid-phase can be modified to facilitate the stable attachment of (strept) avidin, linkers or binding agents. Generally a skilled artisan can use routine methods to modify a solid-phase support in accordance with the desired application.

Interaction between (strept)avidin and biotin has found wide application in immunoassays. EP 0540037 exemplifies an early demonstration of the <biotin:(strept)avidin> binding pair in a heterogeneous immunoassay. Reported is a solid phase that is coated with streptavidin and used to immobilize a biotinylated analyte-specific capture antibody. Currently many commercial automated immunoassays incorporate biotinylated antibodies and streptavidin-coated magnetic beads as a means of immobilizing antigen:antibody complexes to a solid phase (Diamandis E. P. & Christopoulos T. K. Clin Chem 37 (1991) 625-636). Such assay design, however, can be vulnerable to interference from high biotin concentrations within the sample. In such an event excess free biotin competes with biotinylated antibody, thereby causing falsely low results in sandwich immunoassays and falsely high results in competitive immunoassays (Henry J. G. et al. Ann Clin Biochem 33 (1996) 162-163).

Grimsey P. et al. (Int. J. Pharmacokinet. 2 (2017) 247-256) reported an evaluation of the effective half-life of biotin and biotin metabolites in serum, and a pharmacokinetic (PK) model was reported to simulate the time taken for the serum biotin concentration to fall below a series of thresholds. Nevertheless, there is a technical need to provide an alternative to the <biotin:(strept)avidin> binding pair in diagnostic immunoassays, specifically in view of cases where biotin is applied in megadoses, or considering patients with high biotin serum concentrations as a result of disease. Patients of the latter group are vulnerable to interference; high biotin levels in blood (and plasma) are due to rare inborn errors of metabolism for which high-dose biotin therapy is an established treatment, such as biotinidase deficiency, holocarboxylase synthetase deficiency and biotin-thiamine-responsive basal ganglia disease. Also, high-dose biotin therapy has been adopted as part of a treatment for progressive multiple sclerosis (Sedel F. et al. Mult Scler Relat Disord 4 (2015) 159-169).

Therefore, with the increased use of high dose biotin an increasing need exists to counteract potential interference by abnormally high biotin levels in a sample. Particular focus is directed to the determination (qualitative or quantitative detection) of an analyte from a sample in immunoassays which are based on formation of the <biotin:(strept)avidin> binding pair. The present disclosure aims at providing technically feasible, robust and economically viable assays to determine an analyte in a sample, wherein the herewith provided assays are insensitive towards interference by dissolved biotin that may be present in samples to be analyzed. Thus, reported and provided are specifically immunoassays which are insensitive to biotin interference during the course of the immunoassay workflow.

A key focus of the present disclosure is the means by which the detection complex becomes immobilized (anchored) on the solid phase, e.g., but not limited to, during the course of a heterogeneous assay to determine an analyte in a sample. In particular, the present disclosure focuses on the use of a binding pair other than <biotin:(strept)avidin> which facilitates immobilization of an analyte-specific capturing agent, an analyte or a detection complex in the presence of high amounts of biotin.

Attaching the member of the alternative binding pair to the (strept)avidin-coated solid phase under controlled conditions (i.e. in the controlled absence of interfering concentrations of free biotin) provides an advantageous material for used in analyte-detection assays such as heterogeneous immunoassays. The basic underlying concept of the present report is that the skilled person can continue using the established (strept)avidin-coated solid phases—even those of already existing detection assays—when an alternative binding member desired for coating is attached as a biotin conjugate. That is to say, the present disclosure proposes to attach a selected member of an alternative binding pair onto a (strept)avidin-coated solid phase of choice, wherein the selected member of the alternative binding pair is in biotinylated form. It is recalled that the selected member itself is neither biotin nor (strept)avidin. Hence, according to the concept of this disclosure the <biotin:(strept)avidin> is formed in the preparation process of the solid phase, e.g. but not limited to the preparation during manufacture of the solid phase. Importantly, the preparation process occurs prior to the solid phase being used in an analyte-detection assay, i.e. prior to getting in contact with a sample that potentially contains an interference-causing concentration of biotin.

The present report thus discloses "overcoating" of known and established (strept)avidin-coated solid phases with a selected member of an alternative binding pair. The concept of overcoating provides an aspect of the present disclosure. Accordingly, a first aspect relates to a solid phase coated with (strept)avidin and having attached thereto, by way of <biotin:(strept)avidin> interaction, a biotinylated first member of a binding pair, wherein the attached first member is capable of binding to a second member of the binding pair, but is not capable of binding to biotin or to (strept)avidin, and wherein no member of the binding pair is capable of hybridizing with a naturally-occurring single-stranded nucleic acid. This aspect includes a solid phase coated with (strept)avidin and having attached thereto, by way of <biotin:(strept)avidin> interaction, a biotinylated first member of a binding pair, wherein the attached first member is capable of binding to a second member of the binding pair, but is not capable of binding to biotin or to (strept)avidin, wherein the second member is capable of becoming bound by the first member when the second member is part of a conjugate comprising any of an analyte, an analyte analogon, and an analyte-specific capturing agent, and wherein no member of the binding pair is capable of hybridizing with a naturally-occurring single-stranded nucleic acid.

Importantly, it is understood throughout this disclosure and for all aspects and embodiments reported herein that the binding pair—i.e. the binding pair to replace <biotin:(strept)avidin>—excludes any of <analyte:analyte-specific capturing agent> and <analyte analogon:analyte-specific capturing agent>.

Thus, the surface of the solid phase is initially coated with (strept)avidin, directly or indirectly as can be chosen by the skilled person. In a subsequent coating step, the biotin moiety of the biotinylated first member of the binding pair anchors the first member on the surface of the (strept)avidin-coated solid phase, thereby facilitating presentation of the first member into the medium that is surrounding the solid phase, e.g. an aqueous solution which is a particular embodiment of such a medium.

It is of technical importance that the binding pair does not comprise naturally-occurring nucleic acids such as DNA or RNA, e.g. as already disclosed in methods of sequence capture, e.g. as described by Mastrangeli R. et al. (Analytical Biochemistry 241 (1996) 93-102). That is to say, members of hybridizing pairs of nucleic acids which are capable of hybridizing with DNA and RNA are excluded. Also, any structural analog capable of hybridizing with DNA or RNA is excluded. A first important reason for excluding such binding partners is the occurrence of single-stranded nucleic acids in samples such as whole-blood, and blood-derived samples like plasma and serum. Such nucleic acids comprised in samples pose a significant source of interference with hybridizing members of a pair of complementary DNA or RNA molecules, or functional analogues thereof. In order to avoid DNA or RNA molecules competing with the specific interaction between a first binding member to a second binding member it must therefore be excluded that any of the members of the binding pair is capable of forming a duplex with naturally occurring single-stranded nucleic acids.

A further reason against selecting a binding pair specifically made from DNA or RNA is that these binding partners are nuclease sensitive. Therefore, they must generally be deemed instable in the presence of most samples of biological origin, and are therefore excluded as binding pairs according to the concept presented here. Thus, with regards to the first aspect and all other aspects reported herein, the pair of binding members is selected such that no member of the binding pair is capable of hybridizing with a naturally-occurring single-stranded nucleic acid (i.e. DNA or RNA).

Replacement of the <biotin:(strept)avidin> binding pair requires the alternative binding pair to have specific desired technical features. Thus, the interaction of the two binding partners has to be specific. Furthermore, the kinetics of connection forming, that is to say the speed with which the two separate partners of the binding pair interact and eventually associate, i.e. attach to each other, is desired to be high. In addition, the connection of the two binding partners is desired to be stable once formed, even though the connection is effected by non-covalent binding. Moreover, the binding partners must be amenable to chemical conjugation with other molecules such as (but not limited to) analytes and analogs thereof, as well as analyte-specific receptors, for their application in immunoassays.

Relating to all aspects as disclosed in here, in an embodiment the first member is capable of binding to a second member of the binding pair. In this embodiment capability of binding to the other member is independent from the respective member being free in solution or attached to a solid phase, being conjugated or not conjugated to a macromolecule (such as, but not limited to, an analyte-specific capturing agent, e.g. an antibody), being biotinylated or not biotinylated, being attached to (strept)avidin or not attached to (strept)avidin (provided the respective member is biotinylated). These features importantly also apply to all embodiments that include the presence of a liquid aqueous solution which is in contact with the members of the binding pair.

It is also important to appreciate that in immunoassays analyte-specific capturing agents (=receptors or receptor molecules) and typically also the analytes to be detected (or analogs thereof) retain their conformation and function only under certain conditions which may differ depending on the particular receptor or analyte that is under specific consideration; thus, a receptor molecule or an analyte may tolerate only limited deviation from these conditions. Such conditions may comprise (but are not limited to) a buffered aqueous solution with a pH in the range from about 6.5 to about 8.5, one or more dissolved salts, one or more helper substances, a total amount of solutes in the range from about 250 to about 500 mosm/kg, at a pre-selected temperature in the range of 1° C. to 40° C., to name but a few. Thus, in a specific embodiment the first member is capable of binding to a second member of the binding pair in the presence of a liquid aqueous solution with a pH in the range from about pH 3 to about pH 11, more specifically in the range from about pH 5 to about pH 9, more specifically in the range from about pH 6.5 to about pH 8.5, even more specifically at about pH 7. In another specific embodiment the first member is capable of binding to a second member of the binding pair in the presence of a liquid aqueous solution with a total amount of solutes in the range from about 1 to about 1000 mosm/kg, more specifically in the range from about 250 to about 500 mosm/kg. In another specific embodiment the first member is capable of binding to a second member of the binding pair in the presence of a liquid aqueous solution, the solution having a temperature in the range from −10° C. to 50° C., more specifically in the range from 0° C. to about 40° C.

A binding pair other than <biotin:(strept)avidin> is desired for attachment of a target to a solid phase. Similar to biotin:(strept)avidin, the alternative binding pair will consist of a first and a second binding partner, wherein at least one binding partner can be biotinylated for becoming attached to a (strept)avidin-coated surface of a solid phase, and another binding partner which needs to be capable of being coupled to another molecule, e.g. to an analyte-specific capturing agent.

The two members of the desired binding pair require to be capable of forming a specific connection with each other, i.e. specifically bind to each other under conditions which are also compatible with receptor:analyte capturing and/or binding. The specific connection of the two members of a binding pair is non-covalent, i.e. binding is based on non-covalent interaction such as van der Waals, hydrophobic and electrostatic interactions, hydrogen bonds, ion-induced dipole and dipole-induced dipole interactions, and also complexes such as exemplified as <protein:ligand>, <metal ion:chelate> and others. The above desired features particularly imply that the separate binding partners do not require any denaturing pre-treatment in order to gain the ability to bind the corresponding binding partner. Rather, the binding partners need to be functional binding partners under binder: analyte binding conditions. Specifically, for purposes of diagnostic immunoassays, the members of a binding pair are desired to be capable of forming a connection with each other without pre-treatment in a sample of whole blood, serum or plasma, i.e. in an aqueous solution derived from whole blood, serum or plasma. Further, the association rate of the envisaged binding partners is desired to be $10^5$ $M^{-1}$ $s^{-1}$ or higher, in order to allow for connection of the binding partners in a short period of time, under ambient conditions, using reasonable amounts of binding partners on the separate elements that need to be connected with the respective binding pair of connected first and second members.

In addition, the separate members of an alternative binding pair are required to be amenable to conjugation, specifically conjugation with biomolecules and conjugation with solid phase surfaces, without losing their ability to specifically connect with each other. With regards to conjugates in immunoassays each separate binding partner of the alternative binding pair must be functional under the assay conditions. The same reasoning applies to all other desired materials for conjugation with a binding partner, such as, but not limited to, an analyte, any helper material, a solid phase, and other substances or compounds that may be present during the course of an assay to detect an analyte in a sample.

In an embodiment related to all aspects and embodiments disclosed herein, the binding pair is selected from the group consisting of

- a first and a second oligonucleotide spiegelmer, each consisting of L-ribose- or L-2'-deoxyribose-containing nucleoside monomers, the first oligonucleotide spiegelmer being capable of hybridizing with the second oligonucleotide spiegelmer;
- a first and a second oligomer consisting of beta-L-LNA nucleoside monomers, the first oligomer being capable of hybridizing with the second oligomer;
- an antigen and an antigen-specific antibody;
- a hapten and a hapten-specific antibody;
- a ligand and a specific ligand-binding domain;
- an oligo- or polysaccharide and a lectin, the lectin being capable of specifically binding to the oligo- or polysaccharide;
- a histidine-tag and a metal-chelate complex comprising a metal ion selected from $Zn^{2+}$, $Ni^{2+}$, $Co^{2+}$, and $Cu^{2+}$, the metal-chelate complex being capable of binding to the histidine-tag;
- an indium chelate complex and the CHA255 antibody;
- a cucurbit[n]uril host residue and a guest residue capable of binding the host residue; and a first and a second protein dimerization domain, optionally in the presence of a dimerization inducing or enhancing agent.

A spiegelmer is known to the skilled person as a mirror-image stereoisomer of a given chemical compound that comprises a stereocenter. In an exemplary embodiment, spiegelmers are synthetic oligonucleotides built from non-natural L-nucleotides. In a specific embodiment the binding pair selected as a replacement for <biotin:(strept)avidin> is a first and a second oligonucleotide spiegelmer, each consisting of L-ribose- or L-2'-deoxyribose-containing nucleoside monomers, the first oligonucleotide spiegelmer being capable of hybridizing with the second oligonucleotide spiegelmer. Importantly, such spiegelmers have the property of not being capable of hybridizing with a naturally-occurring single-stranded nucleic acid (DNA or RNA). In addition, oligonucleotide spiegelmers as mentioned are no substrates for naturally-occurring nucleases because the enzyme pockets of such enzymes are incompatible with oligonucleotide analogs consisting of L-ribose- or L-2'-deoxyribose-monomers.

In a further specific embodiment the binding pair selected as a replacement for <biotin:(strept)avidin> is a first and a second oligomer consisting of beta-L-LNA nucleoside monomers, the first oligomer being capable of hybridizing with the second oligomer. WO 1999/14226 suggests the use of LNA in the construction of affinity pairs for attachment to molecules of interest and solid supports. However it is also known to the art that hybridization of complementary all-LNA single strands poses technical problems. Thermodynamic analysis of all-LNA hybridization is largely empirical and sequence prediction of hybridizing monomers without a prior denaturation step (e.g. heating prior to hybridization) does not appear to be possible, so far. Predictions concerning thermodynamic behavior of LNA-containing oligonucleotides for hybridization with naturally-occurring nucleic acids are aided by dedicated computer programs referred to by Tolstrup N. et al. (Nucleic Acids Research 31 (2003) 3758-3762). However, this cited disclosure explicitly mentions a higher prediction error for LNA oligonucleotides due to the more complex properties of these oligonucleotides, rather than lack of experimental data.

Indeed, when providing certain complementary single-stranded oligonucleotides consisting entirely of LNA monomers (="all-LNA"), particularly a first pair consisting of Seq ID NO:1 and Seq ID NO:2, and a second pair consisting of Seq ID NO:3 and Seq ID NO:4, it was found that these form duplices only slowly or insufficiently when mixed with each other in aqueous solution, and in the absence of a denaturation step.

(Seq ID NO: 1)
5' ctgcctgacg 3'

(Seq ID NO: 2)
5' cgtcaggcag 3', (Seq ID NO: 3)
5' gactgcctgacg 3'

(Seq ID NO: 4)
5' cgtcaggcagtc 3'

However, only after heating the mixture of the pair of single-stranded all-LNA oligonucleotides, the complementary single-stranded molecules were found to be capable of rapidly (not slowly) forming duplex molecules. One possible explanation of this—rather expected—finding is that the isolated single-stranded molecules form inter- or intramolecular secondary structures which need to be broken up, in order to render the oligonucleotides capable of forming Watson-Crick-paired duplex molecules. The effectiveness of a denaturation step prior to the hybridization step is compatible with this conclusion. And this finding in general corroborates previous conclusions concerning difficulties to predict hybridization properties (specifically the hybridization kinetics) of all-LNA molecules.

Unexpectedly, pairs of complementary beta-L-LNA oligonucleotides have been identified which are capable of specifically forming a duplex with Watson-Crick base pairing. Even more surprising was the finding that such beta-L-LNAs hybridize with each other without prior denaturation. Exemplary and non-limiting binding pairs consisting of beta-L-LNA monomers which have been found suitable are (Seq ID NO: 5)
5' tgctcctg 3'

(Seq ID NO: 6)
5' caggagca 3', (Seq ID NO: 7)
5' gcctgacg 3'

(Seq ID NO: 8)
5' cgtcaggc 3', (Seq ID NO: 9)
5' tgctcctgt 3'

(Seq ID NO: 10)
5' acaggagca 3', (Seq ID NO: 11)
5' gtgcgtct 3'

(Seq ID NO: 12)
5' agacgcac 3', (Seq ID NO: 13)
5' gttggtgt 3'

(Seq ID NO: 14)
5' acaccaac 3'

(Seq ID NO: 15)
5' gttggtgtgttggtg 3'

(Seq ID NO: 16)
5' caccaacacaccaac 3'

(Seq ID NO: 17)
5' gttggtgtg 3'

(Seq ID NO: 18)
5' cacaccaac 3'

(Seq ID NO: 19)
5' ggaagagaa 3'

(Seq ID NO: 20)
5' ttctatcc 3'.

In an embodiment the present report therefore provides any of the above binding pairs which are capable of forming a non-covalent connection with each other by hybridization in the absence of denaturing conditions, specifically in the absence of denaturing conditions prior to hybridization. Specifically, any of the above binding pairs are provided for use in an analyte detection assay, more specifically in an immunoassay for detecting an analyte in a sample. Remarkably and apparently in contrast to accepted theory, such oligomers retain their duplex-forming ability stably under ambient conditions and in physiological buffers, either in unmodified form or biotinylated, and also as conjugates. Of particular note, duplex formation of these sequence pairs is fast, i.e. comparable to that of (strept)avidin and biotin, and quantitative.

In yet a further specific embodiment the binding pair selected as a replacement for <biotin:(strept)avidin> is an antigen and an antigen-specific antibody. The skilled person is well aware of a large number of such binding pairs. Importantly, when the antigen is a protein the antigenic determinant which is targeted by the specificity of the antibody can be isolated in case it is a linear epitope. The linear epitope isolated as a peptide representing a sub-sequence thus can serve as a member of this binding pair. In addition, binding pairs are specifically preferred wherein the antibody has undergone affinity maturation to enhance its binding properties versus the antigen.

In yet a further specific embodiment the binding pair selected as a replacement for <biotin:(strept)avidin> is a hapten and a hapten-specific antibody. Binding pairs are specifically preferred wherein the antibody has undergone affinity maturation to enhance its binding properties versus the hapten.

In yet a further embodiment the binding pair selected as a replacement for <biotin:(strept)avidin> is a ligand and a specific ligand-binding domain. In yet a further embodiment the binding pair selected as a replacement for <biotin:(strept)avidin> is an oligo- or polysaccharide and a lectin, the lectin being capable of specifically binding to the oligo- or polysaccharide. In yet a further embodiment the binding pair selected as a replacement for <biotin:(strept)avidin> is a histidine-tag and a metal-chelate complex comprising a metal ion selected from $Zn^{2+}$, $Ni^{2+}$, $Co^{2+}$, and $Cu^{2+}$, the metal-chelate complex being capable of binding to the histidine-tag. In yet a further embodiment the binding pair selected as a replacement for <biotin:(strept)avidin> is an indium chelate complex and the CHA255 antibody. In yet a further embodiment the binding pair selected as a replacement for <biotin:(strept)avidin> is a cucurbit[n]uril host residue and a guest residue capable of binding the host residue. In yet a further embodiment the binding pair selected as a replacement for <biotin:(strept)avidin> is a first and a second protein dimerization domain, optionally in the presence of a dimerization inducing or enhancing agent.

In yet a further embodiment related to all aspects and embodiments disclosed herein, the solid phase is selected from the group consisting of a microparticle, a microwell plate, a test tube, a cuvette, a membrane, a quartz crystal, a film, a filter paper, a disc and a chip. In a more specific embodiment, the solid phase is a microparticle with a diameter from 0.05 μm to 200 μm. In yet a further embodiment related to all aspects and embodiments disclosed herein, the solid phase is a microparticle, more specifically a monodisperse paramagnetic or superparamagnetic bead. See, for example, U.S. Pat. Nos. 4,628,037; 4,965,392; 4,695,393; 4,698,302; and 4,554,088. In another specific embodiment the bead is a polystyrene-based particles with iron embedded. In another specific embodiment the bead is a Dynabead®. In a more specific embodiment, the diameter of the bead is about 3 μm.

In yet a further embodiment related to all aspects and embodiments disclosed herein, the solid phase is in contact with an aqueous liquid phase (=liquid aqueous solution). Thus, in a specific embodiment the solid phase as disclosed herein is in contact with a liquid aqueous solution, the solution having a pH in the range from about pH 3 to about pH 11, more specifically in the range from about pH 5 to about pH 9, more specifically in the range from about pH 6.5 to about pH 8.5, even more specifically at about pH 7. In another specific embodiment the solid phase as disclosed herein is in contact with a liquid aqueous solution, the solution containing a total amount of solutes in the range from about 0.1 to about 1,500 mosm/kg, more specifically in the range from about 250 to about 500 mosm/kg. In another specific embodiment the solid phase as disclosed herein is in contact with a liquid aqueous solution, the solution having a temperature in the range from −10° C. to 50° C., more specifically in the range from 0° C. to about 40° C.

In yet a further embodiment related to all aspects and embodiments disclosed herein, the aqueous liquid phase contains a conjugate, the conjugate comprising a second member of the binding pair. In a specific embodiment the conjugate is dissolved in the aqueous liquid phase. In another specific embodiment the conjugate is attached to the solid phase by means of the binding pair. In yet another specific embodiment the dissolved conjugate and the attached conjugate are present simultaneously and are both in contact with the aqueous liquid phase.

Concerning the provision of a solid phase as presented herein, and also relating to all other aspects and embodiments disclosed herein, the present report includes a method of preparing a solid phase having attached thereto a member of a binding pair, the method comprising the steps of (a) providing a solid phase coated with (strept)avidin;
(b) selecting a binding pair with a first member and a second member;
(c) providing the first member of the binding pair selected in step (b);
(d) biotinylating the first member of step (c);
(e) attaching the biotinylated first member obtained from step (d) to the solid phase of step (a) by contacting the biotinylated first member with the coated solid phase and incubating, thereby attaching the biotinylated first member to the solid phase by way of biotin-(strept)avidin interaction;

wherein in step (b) the pair is selected such that without biotinylation the first and the second member of the binding pair are not capable of binding to streptavidin, in biotinylated form and attached to the coated solid phase the first member of the binding pair is capable of binding to the second member, and no member of the binding pair is capable of hybridizing with a naturally-occurring single-stranded nucleic acid;

thereby obtaining the solid phase having attached thereto the member of the binding pair. Included herein is a method of preparing a solid phase having attached thereto a member of a binding pair, the method comprising the steps of (a) providing a solid phase coated with (strept)avidin;
(b) selecting a binding pair with a first member and a second member;
(c) providing the first member of the binding pair selected in step (b);
(d) biotinylating the first member of step (c);
(e) attaching the biotinylated first member obtained from step (d) to the solid phase of step (a) by contacting the biotinylated first member with the coated solid phase and incubating, thereby attaching the biotinylated first member to the solid phase by way of biotin-(strept)avidin interaction;

wherein in step (b) the pair is selected such that without biotinylation the first and the second member of the binding pair are not capable of binding to streptavidin, in biotinylated form and non-covalently attached to the coated solid phase by way of a biotin:(strept)avidin bond the first member of the binding pair is capable of binding to the second member, in conjugated form and covalently attached to an analyte-specific capturing agent the second member of the binding pair is capable of binding to the biotinylated first member attached to the solid phase, and no member of the binding pair is capable of hybridizing with a naturally-occurring single-stranded nucleic acid;

thereby obtaining the solid phase having attached thereto the member of the binding pair.

Mutatis mutandis, the embodiments of the solid phase presented above apply to this related aspect of the method of preparing the solid phase.

A further aspect of the present disclosure which relates to all other aspects and embodiments as disclosed herein is the use of a solid phase as disclosed herein or of a solid phase obtained from the method of preparing the solid phase as disclosed herein in an assay to determine an analyte in a sample.

Yet, a further aspect of the present disclosure which relates to all other aspects and embodiments as disclosed herein is a method to determine an analyte in a sample, the method comprising the steps of (a) providing the sample with the analyte;

(b) providing a solid phase having attached thereto a first member of a binding pair, wherein the solid phase is a solid phase as disclosed herein or a solid phase obtained from the method of preparing the solid phase as disclosed herein;

(c) providing a conjugate, the conjugate comprising a second member of the binding pair coupled to a capturing agent specific for the analyte (i.e. the agent being an analyte-specific capturing agent);

(d) contacting, mixing and incubating the sample of (a) with conjugate of (c), thereby forming a complex, the complex comprising the analyte being captured by the analyte-specific capturing agent comprised in the conjugate;

(e) immobilizing complex formed in step (d) by contacting and incubating complex with the solid phase of step (b), wherein the first member of the binding pair binds to the second member;

(f) optionally washing immobilized complex obtained from step (e);

(g) determining analyte comprised in immobilized complex;

thereby determining the analyte in the sample.

In an embodiment, analyte in the sample is bound to the capturing agent specific for the analyte. Further, in an embodiment of step (d) a further agent-specific binding agent is attached to the analyte. For this purpose, the analyte requires to comprise two separate recognition sites, one for the analyte-specific capturing agent and one for the analyte-specific further binding agent. Thus, a sandwich complex is formed in which the analyte is sandwiched between the capturing agent and the further binding agent. In an embodiment the analyte-specific further binding agent comprises a label. A labeled further binding agent is also referred to as a "detection agent". The amount of labelled binding agent on the recognition site can be measured by determining label. It will be directly proportional to the concentration of the analyte because the labelled binding agent will not bind if the analyte is not present in the sample. This type of detection assay (certain embodiments being referred to as immunoassay) is termed sandwich assay as the analyte is "sandwiched" between two agents.

Yet, a further aspect of the present disclosure which relates to all other aspects and embodiments as disclosed herein is a method to determine an analyte in a sample, the method comprising the steps of (a) providing the sample with the analyte;

(b) providing a solid phase having attached thereto a first member of a binding pair, wherein the solid phase is a solid phase as disclosed herein or a solid phase obtained from the method of preparing the solid phase as disclosed herein;

(c) providing a conjugate, the conjugate comprising a second member of the binding pair coupled to the analyte or an analogon of the analyte;

(d) providing a labeled analyte-specific detecting agent, wherein the analyte or analyte analogon comprised in the conjugate of step (c) and the analyte in the sample are capable of being bound by the detecting agent;

(e) contacting, mixing and incubating the sample of step (a) with conjugate of step (c) and detecting agent of step (d), thereby forming a first complex comprising the analyte and the detecting agent and a second complex comprising the conjugate and the detecting agent;

(f) immobilizing second complex formed in step (e) by contacting and incubating complex with the solid phase of step (b), wherein the first member of the binding pair binds to the second member;

(g) optionally washing the immobilized complex obtained from step;

(h) determining label comprised in the immobilized complex obtained from step (f) or step (g);

thereby determining the analyte in the sample.

For the purpose of the present disclosure, and in line with the definition presented earlier, and concerning all aspects and embodiments reported herein, it is recalled that the skilled person understands a conjugate as comprising a plurality of molecules which are joined together by means of one or more covalent bonds thereby forming a conjugate of the molecules.

An assay to determine an analyte in a sample can be embodied as a homogeneous assay or as a heterogeneous assay. The term "heterogeneous"—as opposed to "homogeneous"—denotes two essential and separate steps in the assay procedure. In the first step an analyte detection complex containing label is formed and immobilized on a solid phase, however with unbound label still surrounding the immobilized complexes. Prior to determination of a label-dependent signal unbound label is washed away from immobilized detection complex, the wash representing the second step. Notably, a homogeneous assay does not require a washing step, and an analyte-dependent detectable signal is generated by way of a single-step process.

Yet, a further aspect of the present disclosure which relates to all other aspects and embodiments as disclosed herein is a kit for determining an analyte in a sample, the kit comprising (a) in a first container, and either (b) or (c) in a second container, wherein (a) is a solid phase having attached thereto a first member of a binding pair, wherein the solid phase is a solid phase as disclosed herein or a solid phase obtained from the method of preparing the solid phase as disclosed herein, (b) is a first conjugate, the conjugate comprising a second member of the binding pair coupled to a capturing agent specific for the analyte (i.e. the agent being an analyte-specific capturing agent), (c) is a second conjugate, the conjugate comprising a second member of the binding pair coupled to the analyte or an analogon of the analyte.

In an embodiment the kit comprises the solid phase and the first conjugate, and the kit further comprises a labeled analyte-specific detecting agent, wherein the detecting agent and the first conjugate are in different containers, and wherein the analyte-specific capturing agent of the first conjugate and the labeled analyte-specific detecting agent are capable of forming a sandwich complex with the analyte. In an embodiment the kit comprises the solid phase and the second conjugate, and the kit further comprises a labeled analyte-specific detecting agent, wherein the detecting agent and the second conjugate are in different containers, and wherein the analyte or analyte analogon comprised in the conjugate and the analyte in the sample are capable of being bound by the detecting agent.

Yet, a further aspect of the present disclosure which relates to all other aspects and embodiments as disclosed herein is a complex comprising (a) and either (b) or (c), wherein (a) is a solid phase having attached thereto a first member of a binding pair, wherein the solid phase is a solid phase as disclosed herein or a solid phase obtained from the method of preparing the solid phase as disclosed herein, (b) is a first conjugate, the conjugate comprising a second member of the binding pair coupled to a capturing agent specific for the analyte (i.e. the agent being an analyte-specific capturing agent), (c) is a second conjugate, the conjugate comprising a second member of the binding pair coupled to the analyte or an analogon of the analyte, wherein in the complex (a) is bound to (b) or (c), respectively, and wherein in the complex a first member of the binding pair is bound to a second member of the binding pair. Thus, in the complex the binding pair is formed by a first member being attached to a second member.

A large number of technical uses are possible on the basis of a complex as disclosed here. Among others, they include the following. In an embodiment the binding pair bridges the (strept)avidin on the surface of the solid phase on the one hand and the first conjugate on the other hand, thereby immobilizing the first conjugate with the analyte-specific capturing agent on the solid phase. This complex can be extended by attaching the analyte to immobilized capturing agent, thereby immobilizing analyte on the solid phase. As known to the skilled person, such a complex can be useful in assays determining immobilized analyte thereby qualitatively or quantitatively detecting the analyte.

In another embodiment the binding pair bridges the (strept)avidin on the surface of the solid phase on the one hand, and the second conjugate on the other hand, thereby immobilizing the analyte or an analogon of the analyte on the solid phase. As known to the skilled person, such a complex can be useful in quantitatively detecting analyte in a sample using a competitive assay setup as described elsewhere herein. Moreover, the complex can be extended further by attaching analyte-specific capturing agent (such as, but not limited to, an antibody) to immobilized analyte or analogon thereof, thereby immobilizing analyte-specific binding agent on the solid phase. As known to the skilled person, such a complex can be useful in assays determining immobilized capturing agent thereby qualitatively or quantitatively detecting the capturing agent.

Yet, a further aspect of the present disclosure which relates to all other aspects and embodiments as disclosed herein is a method to form a complex as disclosed herein, the method comprising the step of contacting (a) with either (b) or (c), wherein (a) is a solid phase having attached thereto a first member of a binding pair, wherein the solid phase is a solid phase as disclosed herein or a solid phase obtained from the method of preparing the solid phase as disclosed herein, (b) is a first conjugate, the conjugate comprising a second member of the binding pair coupled to a capturing agent specific for the analyte (i.e. the agent being an analyte-specific capturing agent), (c) is a second conjugate, the conjugate comprising a second member of the binding pair coupled to the analyte or an analogon of the analyte, followed by the step of incubating (a) and either (b) or (c), respectively, thereby forming the complex, wherein in the complex (a) is bound to (b) or (c), respectively, and wherein a first member of the binding pair is bound to a second member of the binding pair. Another embodiment is a complex that is obtainable as a product of a method of forming a complex as disclosed herein.

In a more formalized way, the present disclosure comprises the following items, each representing an embodiment of the present disclosure:

1. A solid phase coated with (strept)avidin and having attached thereto, by way of <biotin:(strept)avidin> interaction, a biotinylated first member of a binding pair, wherein the attached first member is capable of binding to a second member of the binding pair, but is not capable of binding to biotin or to (strept)avidin, and wherein no member of the binding pair is capable of hybridizing with a naturally-occurring single-stranded nucleic acid.
2. The solid phase of item 1, obtainable by a method of item 10.
3. The solid phase of item 1 or item 2, wherein the binding pair is selected from the group consisting of
   - a first and a second oligonucleotide spiegelmer, each consisting of L-ribose- or L-2'-deoxyribose-containing nucleoside monomers, the first oligonucleotide spiegelmer being capable of hybridizing with the second oligonucleotide spiegelmer;
   - a first and a second oligomer consisting of beta-L-LNA nucleoside monomers, the first oligomer being capable of hybridizing with the second oligomer;
   - an antigen and an antigen-specific antibody;
   - a hapten and a hapten-specific antibody;
   - a ligand and a specific ligand-binding domain;
   - an oligo- or polysaccharide and a lectin, the lectin being capable of specifically binding to the oligo- or polysaccharide;
   - a histidine-tag and a metal-chelate complex comprising a metal ion selected from $Zn^{2+}$, $Ni^{2+}$, $Co^{2+}$, and $Cu^{2+}$, the metal-chelate complex being capable of binding to the histidine-tag;
   - an indium chelate complex and the CHA255 antibody;
   - a cucurbit[n]uril host residue and a guest residue capable of binding the host residue; and
   - a first and a second protein dimerization domain, optionally in the presence of a dimerization inducing or enhancing agent.
4. The solid phase of any of the items 1 to 3, wherein the solid phase is selected from the group consisting of a microparticle, a microwell plate, a test tube, a cuvette, a membrane, a quartz crystal, a film, a filter paper, a disc and a chip.
5. The solid phase of item 4, wherein the solid phase is a microparticle with a diameter from 0.05 μm to 200 μm.

6. The solid phase of item 5, wherein the microparticle is a monodisperse paramagnetic bead.
7. The solid phase of item 6, wherein the diameter of the bead is about 3 μm.
8. The solid phase of any of the items 1 to 7, wherein the solid phase is in contact with an aqueous liquid phase.
9. The solid phase of item 8, wherein in the liquid phase contains a conjugate, the conjugate comprising a second member of the binding pair.
10. A method of preparing a solid phase having attached thereto a member of a binding pair, the method comprising the steps of
   (a) providing a solid phase coated with (strept)avidin;
   (b) selecting a binding pair with a first member and a second member;
   (c) providing the first member of the binding pair selected in step (b);
   (d) biotinylating the first member of step (c);
   (e) attaching the biotinylated first member obtained from step (d) to the solid phase of step (a) by contacting the biotinylated first member with the coated solid phase and incubating, thereby attaching the biotinylated first member to the solid phase by way of biotin-(strept)avidin interaction;

wherein in step (b) the pair is selected such that without biotinylation the first and the second member of the binding pair are not capable of binding to streptavidin, in biotinylated form and attached to the coated solid phase the first member of the binding pair is capable of binding to the second member, and no member of the binding pair is capable of hybridizing with a naturally-occurring single-stranded nucleic acid;

thereby obtaining the solid phase having attached thereto the member of the binding pair.
11. Use of a solid phase of any of the items 1 to 9 or of a solid phase obtained from the method of item 10 in an assay to determine an analyte in a sample.
12. A kit for determining an analyte in a sample, the kit comprising (a) in a first container, and either (b) or (c) in a second container, wherein
   (a) is a solid phase having attached thereto a first member of a binding pair, wherein the solid phase is a solid phase of any of the items 1 to 9 or a solid phase obtained from the method of item 10,
   (b) is a first conjugate, the conjugate comprising a second member of the binding pair coupled to an analyte-specific capturing agent,
   (c) is a second conjugate, the conjugate comprising a second member of the binding pair coupled to the analyte or an analogon of the analyte.
13. The kit of item 12, the kit comprising (a) and (b), the kit further comprising a labeled analyte-specific detecting agent, wherein the detecting agent and (b) are in different containers, and wherein the analyte-specific capturing agent of (b) and the labeled analyte-specific detecting agent are capable of forming a sandwich complex with the analyte.
14. The kit of item 12, the kit comprising (a) and (c), the kit further comprising a labeled analyte-specific detecting agent, wherein the detecting agent and (c) are in different containers, and wherein the analyte or analyte analogon comprised in the conjugate and the analyte in the sample are capable of being bound by the detecting agent.
15. A complex comprising (a) and either (b) or (c), wherein
   (a) is a solid phase having attached thereto a first member of a binding pair, wherein the solid phase is a solid phase of any of the items 1 to 9 or a solid phase obtained from the method of item 10,
   (b) is a first conjugate, the conjugate comprising a second member of the binding pair coupled to an analyte-specific capturing agent,
   (c) is a second conjugate, the conjugate comprising a second member of the binding pair coupled to the analyte or an analogon of the analyte, wherein in the complex (a) is bound to (b) or (c), respectively, and wherein in the complex a first member of the binding pair is bound to a second member of the binding pair.
16. A complex of item 15, obtainable by a method of item 17.
17. Method to form a complex, the method comprising the step of contacting (a) with either (b) or (c), wherein
   (a) is a solid phase having attached thereto a first member of a binding pair, wherein the solid phase is a solid phase of any of the items 1 to 9 or a solid phase obtained from the method of item 10,
   (b) is a first conjugate, the conjugate comprising a second member of the binding pair coupled to an analyte-specific capturing agent,
   (c) is a second conjugate, the conjugate comprising a second member of the binding pair coupled to the analyte or an analogon of the analyte, followed by the step of incubating (a) and either (b) or (c), respectively, thereby forming the complex, wherein in the complex (a) is bound to (b) or (c), respectively, and wherein a first member of the binding pair is bound to a second member of the binding pair.
18. A method to determine an analyte in a sample, the method comprising the steps of
   (a) providing the sample with the analyte;
   (b) providing a solid phase having attached thereto a first member of a binding pair, wherein the solid phase is a solid phase of any of the items 1 to 9 or a solid phase obtained from the method of item 10;
   (c) providing a conjugate, the conjugate comprising a second member of the binding pair coupled to an analyte-specific capturing agent;
   (d) contacting, mixing and incubating the sample of (a) with conjugate of (c), thereby forming a complex, the complex comprising the analyte being captured by the analyte-specific capturing agent comprised in the conjugate;
   (e) immobilizing complex formed in step (d) by contacting and incubating complex with the solid phase of step (b), wherein the first member of the binding pair binds to the second member;
   (f) optionally washing immobilized complex obtained from step (e);
   (g) determining analyte comprised in immobilized complex;

thereby determining the analyte in the sample.
19. The method of item 18, wherein steps (d) and (e) are performed subsequently or simultaneously.
20. The method of any of the item 18 and 19, wherein step (c) additionally comprises providing a labeled analyte-specific detecting agent, the analyte is capable of being bound simultaneously by the capturing agent comprised in the conjugate and by the detecting agent, thereby being capable of forming a sandwich complex;

step (d) comprises contacting, mixing and incubating the sample of (a) with the conjugate of (c) and additionally labeled analyte-specific detecting agent, thereby forming a complex, the complex comprising analyte being sandwiched between the capturing agent and the detecting agent, and step (g) is performed by determining label comprised in immobilized complex.

21. The method of item 20, wherein prior to step (g) unbound labeled analyte-specific detecting agent is removed from immobilized complex.

22. A method to determine an analyte in a sample, the method comprising the steps of
(a) providing the sample with the analyte;
(b) providing a solid phase having attached thereto a first member of a binding pair, wherein the solid phase is a solid phase of any of the items 1 to 9 or a solid phase obtained from the method of item 10;
(c) providing a conjugate, the conjugate comprising a second member of the binding pair coupled to the analyte or an analogon of the analyte;
(d) providing a labeled analyte-specific detecting agent, wherein the analyte or analyte analogon comprised in the conjugate of step (c) and the analyte in the sample are capable of being bound by the detecting agent;
(e) contacting, mixing and incubating the sample of step (a) with conjugate of step (c) and detecting agent of step (d), thereby forming a first complex comprising the analyte and the detecting agent and a second complex comprising the conjugate and the detecting agent;
(f) immobilizing second complex formed in step (e) by contacting and incubating complex with the solid phase of step (b), wherein the first member of the binding pair binds to the second member;
(g) optionally washing the immobilized complex obtained from step;
(h) determining label comprised in the immobilized complex obtained from step (f) or step (g);

thereby determining the analyte in the sample.

23. The method of item 22, wherein steps (e) and (f) are performed subsequently or simultaneously.

24. The method of any of the items 22 and 23, wherein prior to step (h) unbound labeled analyte-specific detecting agent is removed from immobilized complex.

25. The method of any of the items 22 to 24, wherein a predetermined amount of each of (c) and/or (d) is provided.

26. A method of any of the items 17 to 25, wherein one or more steps are performed in the presence of an aqueous solution comprising a compound selected from the group consisting of a salt, a buffer salt, an ionic detergent, a non-ionic detergent, a surfactant, an anti-oxidant and a preservative agent.

27. A method of any of the items 17 to 26, wherein the aqueous solution contains an aggregate amount of dissolved substances from 0.1 mmol/L to 1,000 mmol/L.

28. A method of item 27, wherein the aqueous solution contains an aggregate amount of dissolved substances from 1 mmol/L to 500 mmol/L.

29. A method of item 28, wherein the aqueous solution contains an aggregate amount of dissolved substances from 10 mmol/L to 500 mmol/L.

30. A method of any of the items 17 to 29, wherein the method is performed at a temperature from 0° C. to 40° C.

31. A method of any of the items 17 to 30, wherein the method is performed with one or more steps being automated.

32. A method of any of the items 18 to 31, wherein determining the analyte in the sample results in a computer-readable datum.

33. A method of item 32, wherein the computer-readable datum is stored in an electronic register.

The following examples and figures are provided to aid the understanding of the present invention, the true scope of which is set forth in the appended claims. It is understood that modifications can be made in the procedures set forth without departing from the spirit of the invention.

EXAMPLE 1

Figure 1:
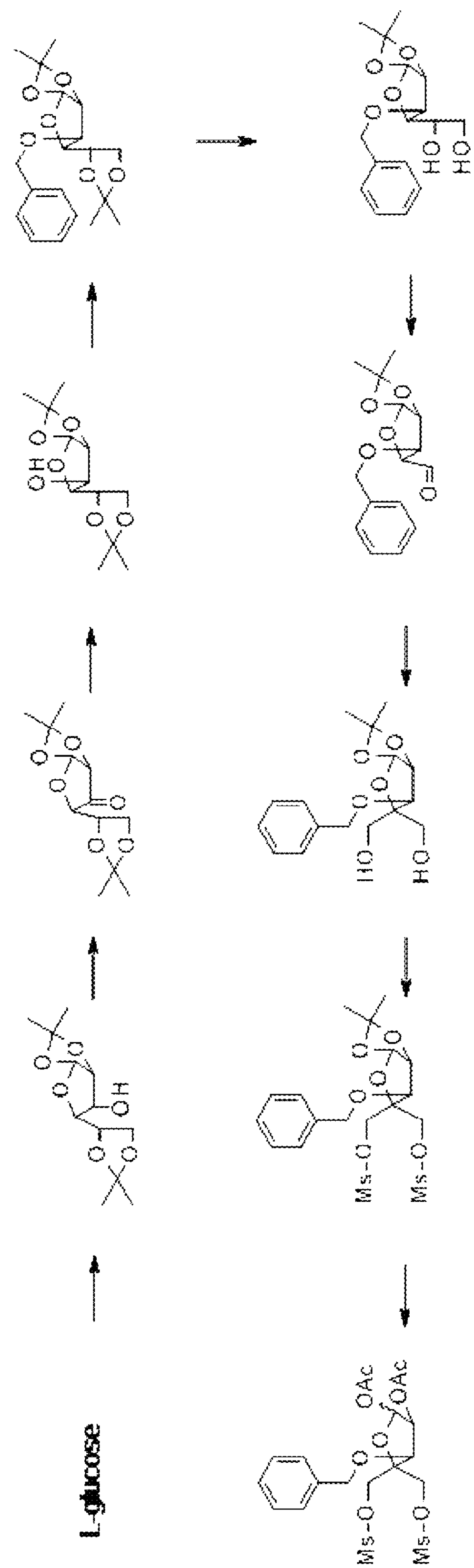
FIG. 1 Synthesis scheme illustrating Example 1.

Synthesis of Sugar Intermediate 1,2-O-Diacetyl-3-O-benzyl-5-O-mesyl-4-C-(mesyloxymethyl)-L-ribose This example illustrates the multi-step synthesis via several intermediate products as indicated in the following. FIG. 1 illustrates the synthesis scheme.

(i)

1,2:5,6-Di-O-isopropylidene-α-L-glucofuranose 1,2:5,6-Di-O-isopropylidene-α-L-glucofuranose was synthesized according to Qu et al., Research on Chemical Intermediates 2014, 40 (4), 1557-1564.

To a stirred suspension of anhydrous L-glucose (50 g, 0.28 mol; available from Carbosynth) in anhydrous acetone (500 mL) pulverized anhydrous zinc chloride (40 g) was added followed by 1.5 mL of 85% phosphoric acid. This mixture was stirred for 30 h at room temperature, and the unreacted sugar was collected by filtration and washed with a small volume of acetone. Filtrate and washings were cooled and made slightly alkaline with 2.5 M sodium hydroxide. Insoluble inorganic material was removed by filtration and washed with acetone. The almost colorless filtrate and washings were concentrated under reduced pressure and the residue was diluted with water, extracted with dichloromethane, dried over magnesium sulfate, and concentrated under reduced pressure. Crystallization of the residue from hexane gave 1,2:5,6-di-O-isopropylidene-α-L-glucofuranose as colorless needles (51 g, 70%).

$R_f$ (ethyl acetate/hexane 1:1)=0.5.

$^1H$ NMR ($CDCl_3$): δ 5.94 (d, 1H), 4.53 (d, 1H), 4.39-4.29 (m, 2H), 4.16 (dd, 1H), 4.06 (dd, 1H), 3.98 (dd, 1H), 2.65 (d, 1H), 1.49 (s, 3H), 1.44 (s, 3H), 1.36 (s, 3H), 1.31 (s, 3H).

(ii)

1,2:5,6-Di-O-isopropylidene-α-L-ribo-hexofuranose-3-ulose

1,2:5,6-Di-O-isopropylidene-α-L-allofuranose 1,2:5,6-Di-O-isopropylidene-α-L-allofuranose was synthesized according to Hassan et al., Bioorganic Chemistry 2016, 65, 9-16.

To a 2 L, 3-necked flask equipped with a mechanical stirrer and a condenser connected at the top to a mineral oil bubbler, a solution of 1,2:5,6-di-O-isopropylidene-α-L-glucofuranose (100 g, 0.38 mol) in ethanol free chloroform (500 mL), potassium carbonate (16.2 g, 0.12 mol), potassium periodate (148.5 g, 0.65 mmol), benzyltriethylammonium chloride (0.9 g, 3.83 mmol) and activated ruthenium (IV) oxide hydrate (1.75 g) were added. The mixture was stirred for 1 h at 0° C., thereafter at room temperature overnight. The mixture was filtered over a Celite pad and the organic phase was separated and washed with water. The aqueous phase was washed with chloroform and the combined organic phases were dried over magnesium sulfate, evaporated and dried under reduced pressure to give 1,2:5,6-di-0-isopropylidene-α-L-ribo-hexofuranose-3-ulose ($R_f$ (ethyl acetate/hexane 3:1)=0.85). The residue was used in the next reaction step without further purification.

1,2:5,6-Di-O-isopropylidene-α-L-ribo-hexofuranose-3-ulose was dissolved in ethanol/water 7:3 (600 mL) and treated with sodium borohydrate (8.73 g) portion wise at 0° C. The mixture turned colorless and was stirred for 3 h at 0° C. and thereafter for 1 h at room temperature. The solvent was concentrated to about 400 mL and another 400 mL of water was added to the mixture. Thereafter the mixture was concentrated to a volume of ca. 400 mL and extracted with dichloromethane. The organic phase was dried over magnesium sulfate and evaporated under reduced pressure to give 1,2:5,6-di-O-isopropylidine-α-L-allofuranose (60 g, 61%) as a white solid.

$^1$H NMR (DMSO-d6): δ 5.66 (d, 1H), 5.05 (d, 1H), 4.45 (t, 1H), 4.23 (dt, 1H), 3.93 (dd, 1H), 3.83 (m, 2H), 3.74 (dd, 1H), 1.45 (s, 3H), 1.32 (s, 3H), 1.28 (s, 3H), 1.27 (s, 3H).

(iii)

3-O-Benzyl-1,2:5,6-di-O-isopropylidene-α-L-allofuranose

3-O-Benzyl-1,2-O-isopropylidene-α-L-allofuranose

3-O-Benzyl-1,2-O-isopropylidene-α-L-allofuranose was synthesized according to Hassan et al., Bioorganic Chemistry 2016, 65, 9-16.

To 1,2:5,6-di-O-isopropylidine-α-L-allofuranose (60 g, 0.235 mol) in DMF (150 mL) benzyl bromide (29.2 mL, 0.245 mol) was added dropwise at 0° C. The reaction mixture was stirred overnight at room temperature. Water (100 mL) was added to the mixture and the product was allowed to crystalize overnight in a refrigerator. The crystals were filtered off, washed with water, dried under reduced pressure to give 3-O-benzyl-1,2:5,6-di-O-isopropylidene-α-L-allofuranose. The residue was dissolved in 70% acetic acid (390 mL) and stirred for 7 h at 36° C. The mixture was evaporated under reduced pressure to yield 3-O-benzyl-1,2-O-isopropylidene-α-L-allofuranose (62.8 g, 86%) as a clear viscous oil.

$R_f$ (ethyl acetate/hexane 1:1)=ca. 0.9.

$^1$H NMR (CDCl3) δ 7.39-7.30 (m, 5H), 5.76 (d, 1H), 4.77 (d, 1H), 4.63-4.54 (m, 2H), 4.13-4.06 (dd, 1H), 4.01-3.91 (m, 2H), 3.68 (d, 2H), 2.88 (br s, 1H), 2.71 (br s, 1H), 1.54 (s, 3H), 1.33 (s, 3H).

(iv)

3-O-Benzyl-1,2-O-isopropylidene-α-L-ribo-pentodialdofuranose

3-O-Benzyl-4-C-hydroxymethyl-1,2-O-isopropylidene-α-L-ribose

A 2 L Erlenmeyer flask equipped with a magnetic stir bar was charged with silica gel (80.6 g, EM Science, catalog no. 9385-9) and dichloromethane (800 mL). An aqueous solution of sodium periodate (80 mL, 52 mmol, 0.65 M) was added dropwise over 5 min, and a white precipitate formed. A solution of 3-O-benzyl-1,2-O-isopropylidene-α-L-allofuranose (10.0 g, 32.3 mmol, 0.5 M) in dichloromethane (65 mL) was added in one portion to the Erlenmeyer flask. The mixture was stirred at room temperature for 1.5 h. Thereafter the reaction was diluted with water (275 mL), and the suspension was transferred to a 2 L separatory funnel. The aqueous and organic layers were separated, and the aqueous layer was extracted with dichloromethane. The combined organic layers were dried over anhydrous magnesium sulfate, filtered, and concentrated under reduced pressure to yield a colorless oil that was dried under high vacuum for 12 h to afford 3-O-benzyl-1,2-O-isopropylidene-α-L-ribo-pentodialdofuranose (5.3 g, 59%).

Aqueous 37% formaldehyde (10.6 mL) and then 1 M sodium hydroxide (53 mL) were added at 0° C. to a stirred solution of crude 3-O-benzyl-1,2-O-isopropylidene-α-L-ribo-pentodialdofuranose (5.3 g, 19 mmol) in water (50 mL). The reaction mixture was then kept at room temperature for 4 days and concentrated under reduced pressure. The residue was extracted with dichloromethane, dried over magnesium sulfate and evaporated to dryness. The residue was purified by column chromatography (silica gel; toluene/diethylether) to give 3-O-benzyl-4-C-hydroxymethyl-1,2-O-isopropylidene-α-L-ribose (4.3 g; 72%).

$R_f$ (ethyl acetate)=0.42.

$^1$H NMR ($CDCl_3$): δ 7.41-7.28 (m, 5H), 5.76 (d, 1H), 4.80 (d, 1H), 4.62 (dd, 1H), 4.52 (d, 1H), 4.21 (d, 1H), 3.90 (dd, 2H), 3.78 (dd, 1H), 3.55 (dd, 1H), 2.37 (t, 1H), 1.89 (dd, 1H), 1.63 (s, 3H), 1.33 (s, 3H).

(v)

3-O-Benzyl-1,2-O-isopropylidene-5-O-mesyl-4-C-(mesyloxymethyl)-α-L-ribose

A solution of 3-O-benzyl-4-C-hydroxymethyl-1,2-O-isopropylidene-α-L-ribose (10 g, 32 mmol) in anhydrous pyridine (30 mL) was cooled in an ice bath, and mesyl chloride (7.5 mL, 96.5 mmol) was added. The mixture was stirred for 1 h at room temperature, diluted with diethyl ether (200 mL), and washed with water. The organic layer was dried over sodium sulfate, concentrated under reduced pressure, coevaporated with toluene (2×100 mL), and dried in vacuo to yield 3-O-benzyl-1,2-O-isopropylidene-5-O-mesyl-4-C-(mesyloxymethyl)-α-L-ribose as a white solid (15.0 g, 95%).

$R_f$ (hexane/ethyl acetate 15:85)=ca. 0.5.

$^1$H NMR ($CDCl_3$): δ 7.42-7.29 (m, 5H), 5.79 (d, 1H), 4.89 (d, 1H), 4.78 (d, 1H), 4.65 (dd, 1H), 4.58 (d, 1H), 4.42 (d, 1H), 4.33 (d, 1H), 4.19 (d, 1H), 4.14 (d, 1H), 3.08 (s, 3H), 2.98 (s, 3H), 1.69 (s, 3H), 1.34 (s, 3H).

(vi)

1,2-O-Diacetyl-3-O-benzyl-5-O-mesyl-4-C-(mesyloxymethyl)-L-ribose

Acetic anhydride (22.6 mL, 240 mmol) and concentrated sulfuric acid (23 μL) were added to a solution of 3-O-benzyl-1,2-O-isopropylidene-5-O-mesyl-4-C-(mesyloxymethyl)-α-L-ribose (15.0 g, 30.2 mmol) in acetic acid (230 mL), and the mixture was stirred overnight at room temperature. More concentrated sulfuric acid (4 μL) was added, and the reaction was continued for 24 h. Thereafter, water (150 mL) was added, and the mixture was stirred for 3 h and washed twice with dichloromethane. The organic layers was washed with saturated sodium hydrogen carbonate (4×200 mL), dried over sodium sulfate, and concentrated under reduced pressure to give 1,2-O-diacetyl-3-O-benzyl-5-O-mesyl-4-C-(mesyloxymethyl)-L-ribose as a colorless oil (14.5 g, 97%; two anomers of ratio ca. 1:5).

$^1$H NMR ($CDCl_3$): δ 7.42-7.24 (m, 5H), 6.17 (s, 1H), 5.37 (d, 1H), 4.62 (d, 1H), 4.52 (d, 1H), 4.50 (d, 1H), 4.42 (d, 1H), 4.38 (d, 1H), 4.30 (d, 1H), 4.19 (d, 1H), 3.02 (s, 3H), 3.01 (s, 3H), 2.14 (s, 3H), 2.10 (s, 3H).

EXAMPLE 2

β-L-LNA-T Phosphoramidite Compounds

Figure 2:
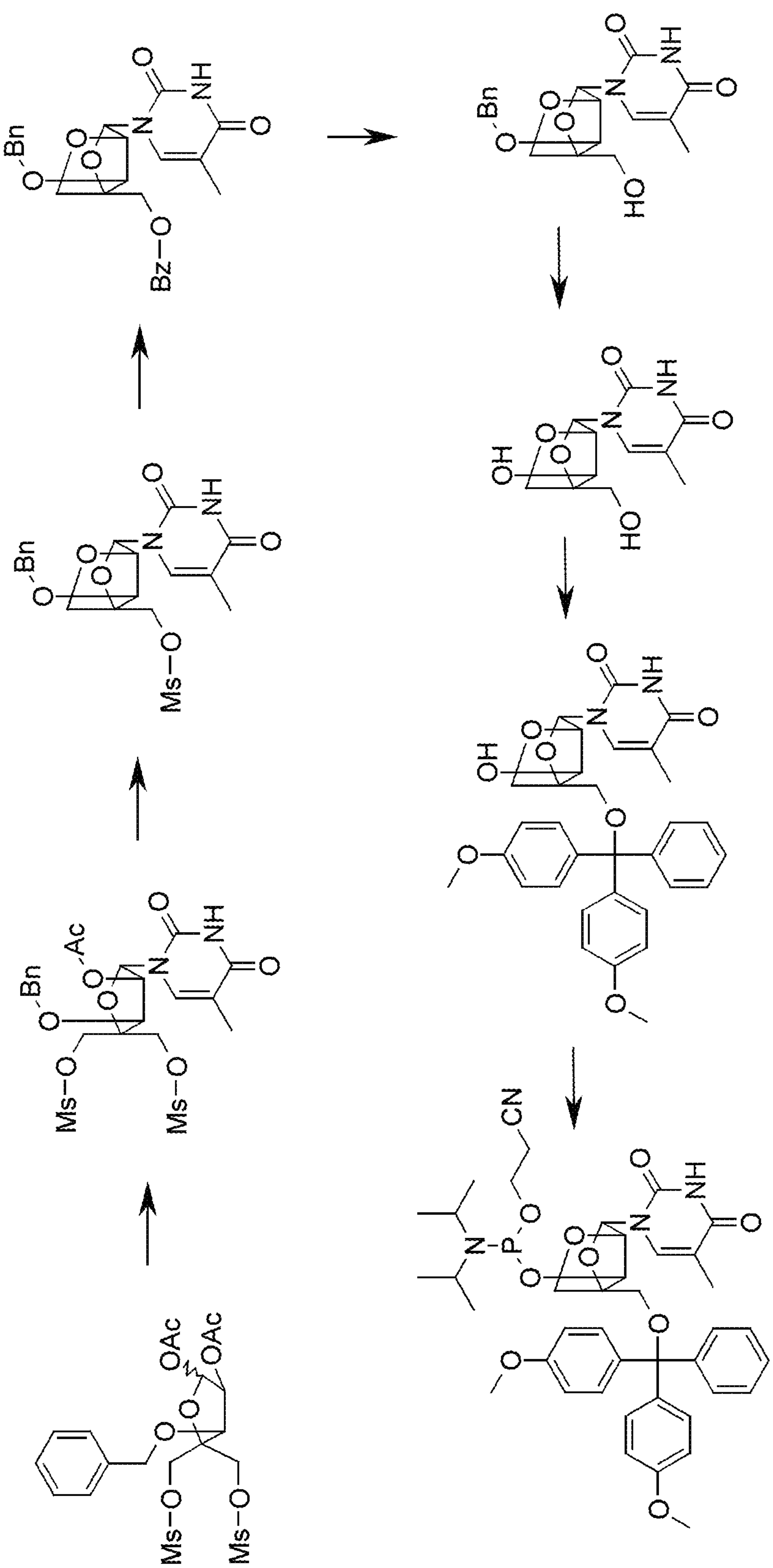
FIG. 2 Synthesis scheme illustrating Example 2.

This example illustrates the multi-step synthesis via several intermediate products as indicated in the following. FIG. 2 illustrates the synthesis scheme. Synthesis was basically performed analogously to Koshkin et al., Journal of Organic Chemistry 2001, 66 (25), 8504-8512.

(i)

1-(2-O-Acetyl-3-O-benzyl-5-O-mesyl-4-C-(mesyloxymethyl)-β-L-ribofuranosyl)thymine N,O-Bis(trimethylsilyl)acetamide (33.7 mL, 136 mmol) was added to a mixture of 1,2-O-diacetyl-3-O-benzyl-5-O-mesyl-4-C-(mesyloxymethyl)-L-ribose (25 g, 49 mmol) and thymine (7.7 g, 61 mmol) in anhydrous acetonitril (120 mL). The reaction mixture was refluxed for 1 h, thereafter trimethylsilyl triflate (11.5 mL, 64 mmol) was added, and refluxing was continued further for 5 h. The solution was kept at room temperature overnight, thereafter diluted with dichloromethane (100 mL), and washed with saturated sodium hydrogen carbonate solution. The organic layer was dried over sodium sulfate and concentrated under reduced pressure. Then the residue was purified by silica gel column chromatography (ethyl acetate) to result 1-(2-O-acetyl-3-O-benzyl-5-O-mesyl-4-C-(mesyloxymethyl)-β-L-ribofuranosyl)thymine (24.0 g, 85%) as a white solid.

$^1$H NMR ($CDCl_3$): δ 9.33 (s, 1H), 7.40-7.28 (m, 5H), 7.08 (d, 1H), 5.71 (d, 1H), 5.58 (dd, 1H), 4.70 (d, 1H), 4.60 (d, 1H), 4.55 (d, 1H), 4.53 (d, 1H), 4.38 (d, 1H), 4.34 (d, 1H), 4.32 (d, 1H), 3.02 (s, 3H), 3.00 (s, 3H), 2.11 (s, 3H), 1.92 (d, 3H).

MS (ESI): 576.6 Da confirmed.

(ii)

3'-O-Benzyl-5'-O-mesyl-β-L-LNA-T

To a solution of 1-(2-O-acetyl-3-O-benzyl-5-O-mesyl-4-C-(mesyloxymethyl)-β-L-ribofuranosyl)thymine (22 g, 38.2 mmol) in 1,4-dioxane/water 1:1 (100 mL) was added 2 M sodium hydroxide (100 mL). The mixture was stirred for 1 h at room temperature, diluted with saturated sodium hydrogen carbonate solution (100 mL), and extracted with dichloromethane. The aqueous phase was acidified by 10% hydrochloric acid and thereafter extracted with dichloromethane. The organic layer was dried over sodium sulfate, concentrated under reduced pressure, and the residue was purified by silica gel column chromatography (1-3% methanol in dichloromethane) to yield 3'-O-benzyl-5'-O-mesyl-3-L-LNA-T (16.1 g, 96%) as a white solid.

$^1$H NMR ($CDCl_3$): δ 9.24 (s, 1H), 7.41-7.22 (m, 6H), 5.68 (s, 1H), 4.66 (d, 1H), 4.61 (s, 1H), 4.59 (d, 1H), 4.56 (d, 1H), 4.52 (d, 1H), 4.08 (d, 1H), 3.93 (s, 1H), 3.87 (d, 1H), 3.08 (s, 3H), 1.93 (s, 3H).

MS (ESI): 438.5 Da confirmed.

(iii)

5'-O-Benzoyl-3'-O-benzyl-β-L-LNA-T

Sodium benzoate (9.9 g, 68.7 mmol) was added to a solution of 3'-O-benzyl-5'-O-mesyl-β-L-LNA-T (15.0 g, 34.2 mmol) in anhydrous N,N-dimethylformamide (400 mL). The mixture was stirred for 5 h at 100° C., cooled to room temperature and filtrated. N,N-dimethylformamide was evaporated under reduced pressure, and the residue was suspended in ethyl acetate (150 mL), washed with saturated sodium chloride solution, dried over sodium sulfate, and concentrated to dryness. Crystallization from ethanol yielded 5'-O-benzoyl-3'-O-benzyl-β-L-LNA-T (14.9 g, 94%) as a white solid.

$R_f$(ethyl acetate)=0.78.

$^1$H NMR ($CDCl_3$): δ 8.78 (s, 1H), 7.94 (m, 2H), 7.61 (m, 1H), 7.45 (m, 2H), 7.30-7.20 (m, 6H), 5.63 (s, 1H), 4.83 (d, 1H), 4.73 (d, 1H), 4.66 (s, 1H), 4.56 (d, 1H), 4.52 (d, 1H), 4.18 (d, 1H), 3.97 (d, 1H), 3.91 (s, 1H), 1.58 (s, 3H).

MS (ESI): 464.5 Da confirmed.

(iv)

3'-O-Benzyl-β-L-LNA-T

Water (25 mL) and 2 M sodium hydroxide (100 mL) were added to a solution of 5'-O-benzoyl-3'-O-benzyl-β-L-LNA-T (14 g, 31.8 mmol) in 1,4-dioxane (100 mL). The reaction mixture was refluxed for 24 h, cooled to room temperature, and neutralized with acetic acid (12.5 mL). Saturated sodium hydrogen carbonate solution (100 mL) was added, and the mixture was washed with dichloromethane. Organic layer was dried over sodium sulfate, and concentrated under reduced pressure. Purification by silica gel column chromatography (1-3% methanol in dichloromethane) yielded 3'-O-benzyl-β-L-LNA-T (10.3 g, 90%) as a white solid.

$R_f$ (ethyl acetate)=0.51.

$^1$H NMR ($CDCl_3$): δ 9.28 (s, 1H), 7.45 (d, 1H), 7.38-7.22 (m, 5H), 5.66 (s, 1H), 4.67 (d, 1H), 4.56 (d, 1H), 4.54 (s, 1H), 4.05 (d, 1H), 4.01 (d, 1H), 3.96 (s, 1H), 3.95 (d, 1H), 3.83 (d, 1H), 1.88 (d, 3H).

MS (ESI): 360.4 Da confirmed.

(v)

β-L-LNA-T Nucleoside

A mixture of 3'-O-benzyl-β-L-LNA-T (10 g, 27.5 mmol), 20% palladium hydroxide on carbon (5 g), and ammonium formiate (5.3 g, 84.6 mmol) was suspended in methanol (70 mL). After refluxing the mixture for 10 min, the catalyst was filtered off and washed with methanol. The combined filtrates were concentrated to a white solid. Crystallization from 15% methanol in dichloromethane afforded β-L-LNA-T (6.5 g, 87%) as a white solid.

$R_f$(ethyl acetate)=0.11.

$^1$H NMR (DMSO-d6): δ 11.32 (br s, 1H), 7.60 (d, 1H), 5.68 (d, 1H), 5.38 (s, 1H), 5.20 (t, 1H), 4.09 (s, 1H), 3.89 (d, 1H), 3.80 (d, 1H), 3.74 (d, 2H), 3.61 (d, 1H), 1.75 (d, 3H).

MS (ESI): 270.2 Da confirmed.

(vi)

5'-O-(4,4'-Dimethoxytrityl)-β-L-LNA-T

β-L-LNA-T nucleoside (5 g, 18.5 mmol) was coevaporated with anhydrous pyridine (50 mL) and redissolved in anhydrous pyridine (150 mL). 4,4'-dimethoxytrityl chloride (7.5 g, 22.1 mmol) and 4-(dimethylamino)pyridine (225 mg, 1.8 mmol) were added. The solution was stirred overnight at room temperature. After addition of methanol the reaction mixture was concentrated under reduced pressure. Thereafter the residue was dissolved in ethyl acetate (150 mL) and extracted with saturated sodium hydrogen carbonate solution. The organic layer was washed with brine (150 mL), dried over sodium sulfate and concentrated under reduced pressure to dryness. Purification by silica gel column chromatography (starting from 40% hexane in ethyl acetate) afforded 5'-O-(4,4'-dimethoxytrityl)-β-L-LNA-T (9.3 g, 88%) as an off-white solid.

$R_f$(ethyl acetate)=0.60.

$^1$H NMR ($CDCl_3$): δ 9.88 (s br, 1H), 7.64 (d, 1H), 7.47-7.14 (m, 9H), 6.85 (dd, 4H), 5.56 (s, 1H), 4.53 (s, 1H), 4.31 (m, 1H), 4.00-3.75 (m, 9H), 3.50 (m, 2H), 1.65 (d, 3H).

MS (ESI): 572.6 Da confirmed.

(vii)

5'-O-(4,4'-Dimethoxytrityl)-β-L-LNA-T, 3'-[(2-cyanoethyl)-(N,N-diisopropyl)]phosphoramidite 5'-O-dimethoxytrityl-β-L-LNA-T (8 g, 14 mmol) was dissolved in anhydrous dichloromethane (125 mL). Thereafter N,N-diisopropylethylamine (6.1 mL, 35 mmol) and 2-cyanoethyl N,N-diisopropylchlorophosphoramidite (5.29 g, 22.4 mmol) were added. The solution was stirred for 3 h at room temperature, and then washed with saturated sodium hydrogen carbonate solution. The organic layer was dried over sodium sulfate and concentrated to dryness under reduced pressure. The residue was purified by silica gel column chromatography (40% hexane in ethyl acetate) to yield 5'-O-(4,4'-dimethoxytrityl)-β-L-LNA-T, 3'-[(2-cyanoethyl)-(N,N-diisopropyl)]phosphoramidite (8.8 g, 81%) as a white solid.

$^{31}$P NMR ($CDCl_3$): δ 149.32, 149.18.

MS (ESI): 772.8 Da confirmed.

EXAMPLE 3

β-L-LNA-C Phosphoramidite Compounds

Figure 3:
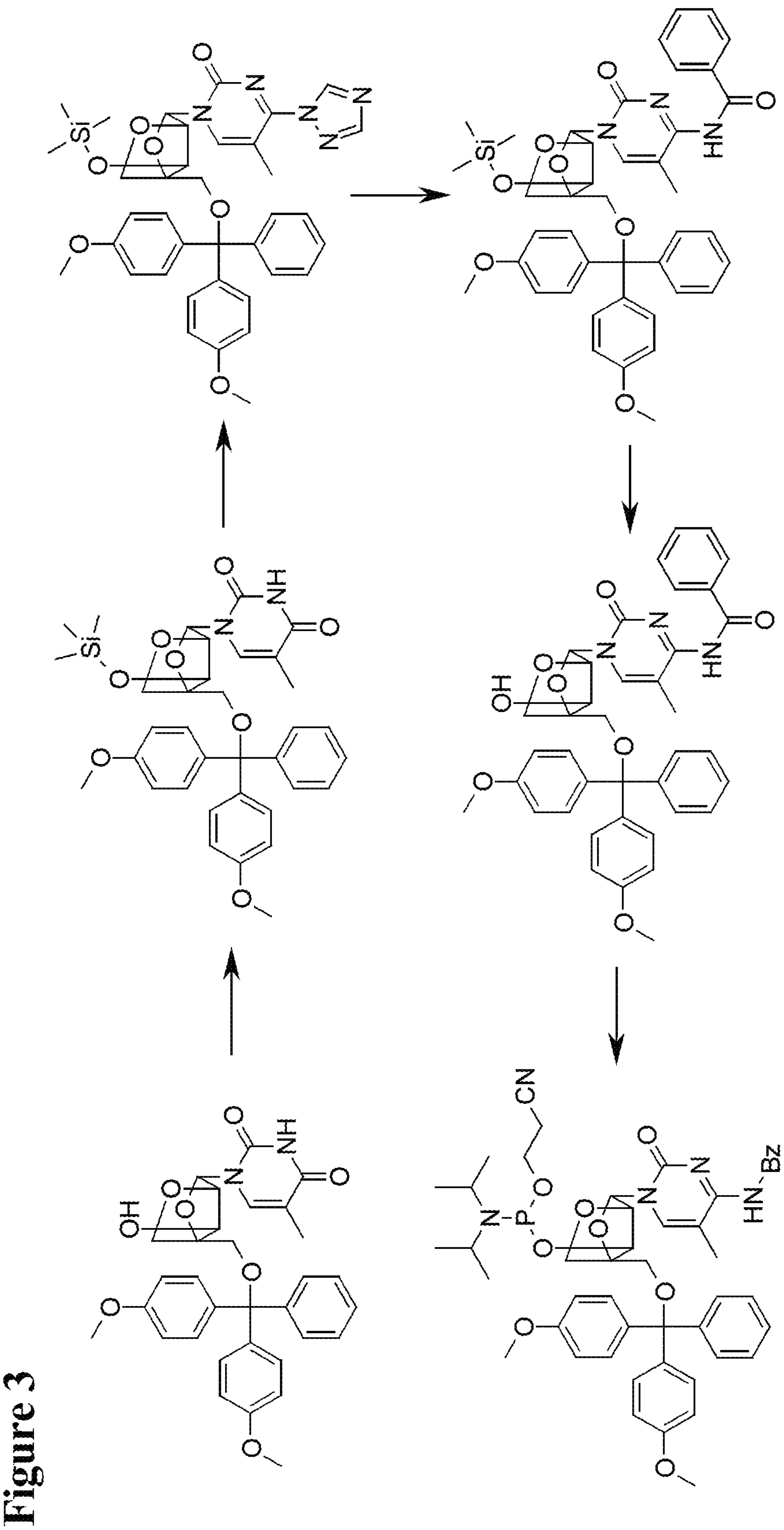
FIG. 3 Synthesis scheme illustrating Example 3.

This example illustrates the multi-step synthesis via several intermediate products as indicated in the following. FIG. 3 illustrates the synthesis scheme.

(i)

5'-O-(4,4'-Dimethoxytrityl)-β-L-LNA-N4-benzoyl-5-methyl-C

5'-O-(4,4'-Dimethoxytrityl)-β-L-LNA-T (13.5 g, 23.6 mmol) was dissolved in anhydrous acetonitrile. At 0° C. triethylamine (9.86 mL, 70.8 mmol) was added, followed by dropwise addition of trimethylsilyl chloride (7.48 mL, 59 mmol). The reaction was stirred for 1 h at 0° C. (reaction mixture A). In parallel, 1,2,4-triazole (24.4 g, 353.3 mmol) was dissolved in anhydrous acetonitrile (150 mL) and thereafter at 0° C. phosphoryl chloride (7.71 mL, 82.5 mmol) was added slowly. After stirring for 15 min at 0° C. triethylamine (59.15 mL, 424.4 mmol) was added. Stirring was continued at 0° C. for 50 min and thereafter reaction mixture A was added. The reaction mixture was stirred for 3 h at 0° C., and then extracted with saturated sodium hydrogen carbonate solution/dichloromethane. The organic phase was dried over sodium sulfate and concentrated to dryness under reduced pressure. The residue was purified by silica gel column chromatography (20% hexane in ethyl acetate to 100% ethyl acetate) to yield the C4-1,2,4-triazolid nucleoside intermediate (15.2 g) as a white solid (LC-MS: 697.4 $[M+H]^+$). Thereafter, benzamide (15.67 g, 129.4 mmol) was suspended in dioxane (100 mL). To this suspension 60% sodium hydride (5.17 g, 129.4 mmol) was added. After 15 min stirring at room temperature the C4-1,2,4-triazolid nucleoside intermediate in dioxane (150 mL) was added. The reaction mixture was stirred for 2 h at room temperature, and thereafter extracted with 5% citric acid/ethyl acetate. The organic layer was washed with saturated sodium hydrogen carbonate solution and brine. Then the organic phase was dried over sodium sulfate and concentrated to dryness to yield 5'-O-(4,4'-dimethoxytrityl)-3'-O-trimethylsilyl-β-L-LNA-N6-benzoyl-5-methyl-C nucleoside $R_f$ (20% hexane in ethyl acetate)=0.87). This intermediate was dissolved in tetrahydrofurane (250 mL), and 1 M tetrabutylammonium fluoride in tetrahydrofurane (23.7 mL, 23.7 mmol) was added. After 15 min stirring at room temperature the solvent was evaporated. The residue was dissolved in dichloromethane and washed with saturated sodium hydrogen carbonate solution. The organic layer was dried over sodium sulfate and concentrated to dryness under reduced pressure. The residue was purified by silica gel column chromatography (40% hexane in ethyl acetate) to yield 5'-O-(4,4'-dimethoxytrityl)-β-L-LNA-N4-benzoyl-5-methyl-C (14 g, 88% from 5'-O-dimethoxytrityl-β-L-LNA-T) as an off-white solid.

$R_f$ (20% hexane in ethyl acetate)=0.64.

$^1$H NMR ($CDCl_3$): δ 8.30 (d, 2H), 7.80 (s, 1H), 7.56-7.23 (m, 12H), 6.86 (dd, 4H), 5.66 (s, 1H), 4.46 (s, 1H), 4.29 (s, 1H), 3.90-3.79 (m, 8H), 3.60-3-47 (dd, 2H), 2.03 (s, 3H).

MS (ESI): 675.7 Da confirmed.

(ii)

5'-O-(4,4'-Dimethoxytrityl)-β-L-LNA-N4-benzoyl-5-methyl-C, 3'-[(2-cyanoethyl)-(N,N-diisopropyl)] phosphoramidite 5'-O-(4,4'-dimethoxytrityl)-β-L-LNA-N4-benzoyl-5-methyl-C (4.6 g, 6.8 mmol) was dissolved in anhydrous dichloromethane (70 mL). Thereafter N,N-diisopropylethylamine (2.37 mL, 13.6 mmol) and 2-cyanoethyl N,N-diisopropylchlorophosphoramidite (3.22 g, 13.6 mmol) were added. The solution was stirred for 1 h at room temperature, and then washed with 5-10% sodium hydrogen carbonate solution. The organic layer was dried over sodium sulfate and concentrated to dryness under reduced pressure. The residue was purified by silica gel column chromatography (40% hexane in ethyl acetate) to yield 5'-O-(4,4'-dimethoxytrityl)-β-L-LNA-N4-benzoyl-5-methyl-C, 3'-[(2-cyanoethyl)-(N,N-diisopropyl)]phosphoramidite (5.0 g, 84%) as a white solid.

$R_f$(ethyl acetate/hexane 3:2)=0.84.

$^{31}$P NMR ($CDCl_3$): δ 149.46, 149.42.

MS (ESI): 875.9 Da confirmed.

EXAMPLE 4

β-L-LNA-A Phosphoramidite Compounds

Figure 4:
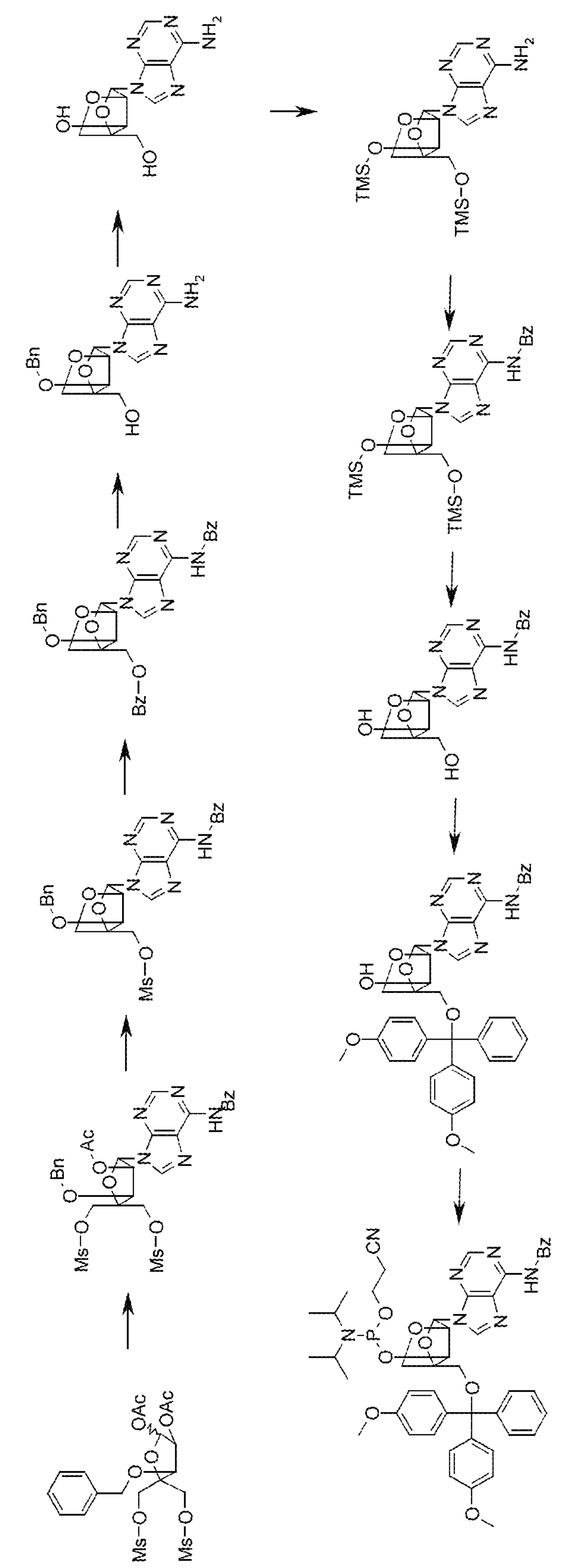
FIG. 4 Synthesis scheme illustrating Example 4.

This example illustrates the multi-step synthesis via several intermediate products as indicated in the following. FIG. 4 illustrates the synthesis scheme. Synthesis was basically performed analogously to Koshkin et al., Journal of Organic Chemistry 2001, 66 (25), 8504-8512.

(i)

9-(2-O-Acetyl-3-O-benzyl-5-O-mesyl-4-C-(mesyloxymethyl)-β-L-ribofuranosyl)N6-benzoyladenine To a suspension of 1,2-O-diacetyl-3-O-benzyl-5-O-mesyl-4-C-(mesyloxymethyl)-L-ribose (25 g, 49 mmol) and N6-benzoyladenine (14.06 g, 58.8 mmol) in anhydrous 1,2-dichloroethane (200 mL) was added N,O-bis(trimethylsilyl)acetamide (32 mL, 128.8 mmol). The mixture was refluxed for 1 h, thereafter trimethylsilyl triflate (17.7 mL, 98 mmol) was added at room temperature, and refluxing was continued for 48 h. Thereafter the reaction mixture was poured into ice-cold saturated sodium hydrogen carbonate solution (200 mL), stirred for 0.5 h, and filtrated. The phases were separated, and the organic phase was washed with saturated sodium hydrogen carbonate solution, dried over sodium sulfate, and concentrated to dryness under reduced pressure. Purification by silica gel column chromatography (1-2% methanol in dichloromethane gave 9-(2-O-acetyl-3-O-benzyl-5-O-mesyl-4-C-(mesyloxymethyl)-13-L-ribofuranosyl) N6-benzoyladenine (27.4 g, 81%) as an off-white solid.

$^1$H NMR ($CDCl_3$): δ 8.76 (s, 1H), 8.12 (s, 1H), 8.02 (m, 2H), 7.61 (m, 1H), 7.51 (m, 2H), 7.40-7.34 (m, 5H), 6.23 (d, 1H), 6.08 (dd, 1H), 5.12 (d, 1H), 4.68 (d, 1H), 4.67 (d, 1H), 4.64 (d, 1H), 4.44 (d, 1H), 4.39 (d, 1H), 4.36 (d, 1H), 3.03 (s, 3H), 2.87 (s, 3H), 2.13 (s, 3H).

MS (ESI): 689.7 Da confirmed.

(ii)

3'-O-Benzyl-5'-O-mesyl-β-L-LNA-N6-benzoyl-A 9-(2-O-Acetyl-3-O-benzyl-5-O-mesyl-4-C-(mesyloxymethyl)-13-L-ribofuranosyl)N6-benzoyladenine (25 g, 36.3 mmol) was dissolved in a mixture of tetrahydrofurane (220 mL) and water (150 mL). Lithium hydroxide monohydrate (7.7 g, 183 mmol) was added, and the reaction mixture was stirred for 3.5 h at room temperature. The solution was neutralized with acetic acid (8.4 mL) to result a precipitate which was filtered off and washed with water to afford 3'-O-benzyl-5'-O-mesyl-β-L-LNA-N6-benzoyl-A (19.6 g, 98%) as a white solid.

$^1$H NMR ($CDCl_3$): δ 8.72 (s, 1H), 8.15 (s, 1H), 8.02 (m, 2H), 7.63-7.59 (m, 1H), 7.54-7.50 (m, 2H), 7.32-7.27 (m, 5H), 6.10 (s, 1H), 4.95 (s, 1H), 4.67 (d, 1H), 4.62 (d, 1H), 4.60 (d, 1H), 4.57 (d, 1H), 4.33 (s, 1H), 4.21 (d, 1H), 4.01 (d, 1H), 3.04 (s, 3H).

MS (ESI): 551.6 Da confirmed.

(iii)

N6,5'-O-Di-benzoyl-3'-O-benzyl-β-L-LNA-A

3'-O-Benzyl-5'-O-mesyl-13-L-LNA-N6-benzoyl-A (18 g, 31.6 mmol) was dissolved in anhydrous N,N-dimethylformamide (700 mL). Thereafter sodium benzoate (8.45 g, 58.5 mmol) was added, and the mixture was stirred at 90° C. for 7 h, cooled to room temperature, filtrated, concentrated under reduced pressure, and coevaporated with acetonitrile. The residue was dissolved in dichloromethane (200 mL), washed with saturated sodium hydrogen carbonate solution and brine, dried over sodium sulfate, and concentrated to dryness under reduced pressure. Crystallization from water/ethanol 1:1 afforded N6,5'-O-di-benzoyl-3'-O-benzyl-13-L-LNA-A (15.5 g, 85%) as a white solid.

$^1$H NMR (DMSO-d6): δ 11.2 (br s, 1H), 8.72 (s, 1H), 8.48 (s, 1H), 8.06 (m, 2H), 7.94 (m, 2H), 7.66 (m, 2H), 7.54 (m, 4H), 7.36-7.26 (m, 5H), 6.11 (s, 1H), 4.97 (s, 1H), 4.82 (s, 2H), 4.77 (s, 1H), 4.75 (d, 1H), 4.69 (d, 1H), 4.19 (d, 1H), 4.07 (d, 1H).

MS (ESI): 577.6 Da confirmed.

(iv)

3'-O-Benzyl-β-L-LNA-A

N6,5'-O-Di-benzoyl-3'-O-benzyl-β-L-LNA-A (15 g, 25.9 mmol) was suspended in a mixture of methanol (150 mL) and concentrated ammonia (200 mL). The solution was stirred for 2 days at room temperature. Thereafter methylamine (40%, 19.4 mL) was added, and the mixture was stirred overnight. The precipitate was filtered off, dried in vacuo, and crystallized from ethanol to afford 3'-O-benzyl-3-L-LNA-A (8.1 g, 85%) as a white solid.

$^1$H NMR (DMSO-d6): δ 8.18 (s, 1H), 8.14 (s, 1H), 7.33-7.30 (m, 5H), 5.97 (s, 1H), 5.17 (t, 1H), 4.73 (s, 1H), 4.63 (s, 2H), 4.35 (s, 1H), 3.95 (d, 1H), 3.84-3.81 (m, 3H).

MS (ESI): 369.4 Da confirmed.

(v)

β-L-LNA-A Nucleoside

To a suspension of 3'-O-benzyl-3-L-LNA-A (7.4 g, 20.0 mmol) in ethanol (100 mL) were added 20% palladium hydroxide on carbon (2 g) and ammonium formiate (6.4 g, 100.8 mmol). The reaction mixture was refluxed for 3 h, and more ammonium formiate (2 g, 31.8 mmol) was added. After 2 h, the hot solution was filtrated through a Celite pad which was washed with boiling ethanol/water (200 mL). The combined filtrates were concentrated under reduced pressure to afford β-L-LNA-A nucleoside (5.5 g, 98%) as white crystals.

$^1$H NMR (DMSO-d6): δ 8.22 (s, 1H), 8.15 (s, 1H), 7.30 (br s, 2H), 5.89 (s, 1H), 5.68 (d, 1H), 5.05 (t, 1H), 4.41 (s, 1H), 4.25 (d, 1H), 3.92 (d, 1H), 3.82 (m, 2H), 3.76 (d, 2H).

MS (ESI): 279.3 Da confirmed.

(vi)

β-L-LNA-N6-benzoyl-A

β-L-LNA-A nucleoside (4.8 g, 17.2 mmol) was coevaporated in anhydrous pyridine (50 mL), thereafter suspended in anhydrous pyridine (100 mL). Then trimethylsilyl chloride (11.6 mL, 91 mmol) was added. The reaction mixture was stirred for 1 h at room temperature. Thereafter benzoyl chloride (2.6 mL, 22.4 mmol) was added. The reaction mixture was stirred for 4 h at room temperature. Thereafter the reaction mixture was cooled to 0° C. Then water (20 mL) and concentrated ammonia (25 mL) were added. The ice bath was removed, and the reaction mixture was stirred for 1 h at room temperature, then concentrated under reduced pressure and extracted with dichloromethane/water. The organic layer was dried over sodium sulfate and concentrated to dryness under reduced pressure to give β-L-LNA-N6-benzoyl-A (6.2 g, 95%) as white solid.

$^1$H NMR (methanol-d4): δ 8.73 (s, 1H), 8.57 (s, 1H), 8.11 (m, 2H), 7.69 (m, 1H), 7.59 (m, 2H), 6.16 (s, 1H), 4.67 (s, 1H), 4.42 (s, 1H), 4.12 (d, 1H), 4.01 (s, 2H), 3.95 (d, 1H).

MS (ESI): 383.4 Da confirmed.

(vii)

5'-O-(4,4'-Dimethoxytrityl)-β-L-LNA-N6-benzoyl-A

β-L-LNA-N6-benzoyl-A nucleoside (5 g, 13.0 mmol) was coevaporated with anhydrous pyridine (50 mL) and redissolved in anhydrous pyridine (150 mL). 4,4'-dimethoxytrityl chloride (5.3 g, 15.5 mmol) and 4-(dimethylamino)pyridine (0.16 g, 1.3 mmol) were added. The solution was stirred overnight at room temperature. After addition of methanol the reaction mixture was concentrated under reduced pressure. Thereafter the residue was dissolved in ethyl acetate (150 mL) and extracted with saturated sodium hydrogen carbonate. The organic layer was washed with brine, dried over sodium sulfate and concentrated under reduced pressure to dryness. Purification by silica gel column chromatography (starting from 20% hexane in ethyl acetate to ethyl acetate) afforded 5'-O-(4,4'-dimethoxytrityl)-β-L-LNA-N6-benzoyl-A (6.7 g, 75%) as an off-white solid.

$^{1}$H NMR (DMSO-d6): δ 11.21 (s, 1H), 8.75 (s, 1H), 8.47 (s, 1H), 8.02 (d, 2H), 7.65-7.18 (m, 12H), 6.87 (dd, 4H), 6.12 (s, 1H), 5.75 (d, 1H), 4.57 (s, 1H), 4.42 (d, 1H), 3.98 (dd, 1H), 3.93 (dd, 1H), 3.70 (s, 6H), 3.54 (dd, 1H), 3.31 (dd, 1H).

MS (ESI): 685.7 Da confirmed (viii)

5'-O-(4,4'-Dimethoxytrityl)-β-L-LNA-N6-benzoyl-A,3'-[(2-cyanoethyl)-(N,N-diisopropyl)]phosphoramidite 5'-O-(4,4'-Dimethoxytrityl)-β-L-LNA-N6-benzoyl-A (6.5 g, 9.4 mmol) was dissolved in anhydrous dichloromethane (100 mL). Thereafter N,N-diisopropylethylamine (4.1 mL, 23.7 mmol) and 2-cyanoethyl N,N-diisopropylchlorophosphoramidite (3.57 g, 15.1 mmol) were added. The solution was stirred for 3 h at room temperature, and then washed with saturated sodium hydrogen carbonate solution. The organic layer was dried over sodium sulfate and concentrated to dryness under reduced pressure. The residue was purified by silica gel column chromatography (20% hexane in ethyl acetate) to yield 5'-O-(4,4'-dimethoxytrityl)-β-L-LNA-N6-benzoyl-A,3'-[(2-cyanoethyl)-(N,N-diisopropyl)] phosphoramidite (7.0 g, 84%).

$^{31}$P NMR ($CDCl_3$): δ 149.58, 149.43.

MS (ESI): 885.9 Da confirmed.

EXAMPLE 5

β-L-LNA-G Phosphoramidite Compounds

Figure 5:
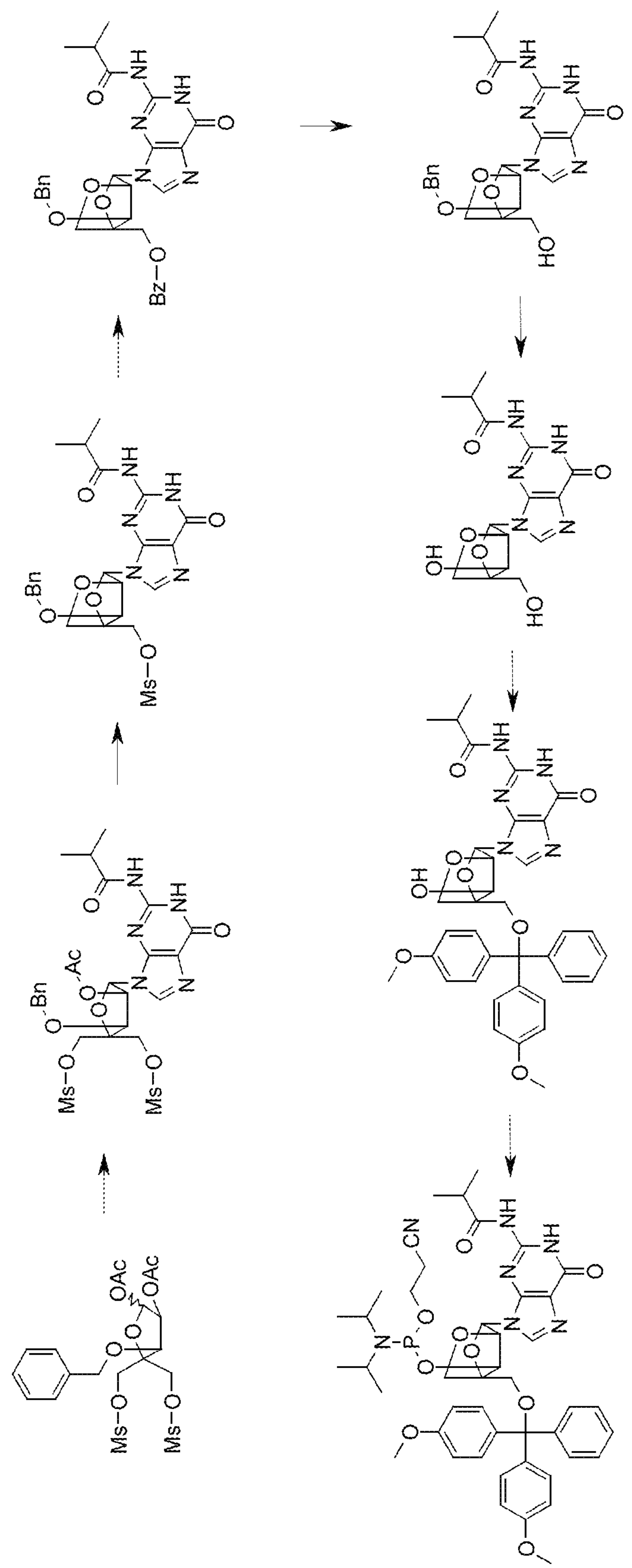
FIG. 5 Synthesis scheme illustrating Example 5.

This example illustrates the multi-step synthesis via several intermediate products as indicated in the following. FIG. 5 illustrates the synthesis scheme. Synthesis was basically performed analogously to Koshkin et al., Journal of Organic Chemistry 2001, 66 (25), 8504-8512

(i)

9-(2-O-Acetyl-3-O-benzyl-5-O-mesyl-4-C-(mesyloxymethyl)-β-L-ribofuranosyl)N2-isobutyrylguanine To a suspension of 1,2-O-diacetyl-3-O-benzyl-5-O-mesyl-4-C-(mesyloxymethyl)-L-ribose (25 g, 49 mmol) and N2-isobutyrylguanine (12.36 g, 55.9 mmol) in anhydrous 1,2-dichloroethane (200 mL) was added N,O-bis(trimethylsilyl)acetamide (40.5 mL, 164.9 mmol). The mixture was refluxed for 1 h, thereafter trimethylsilyl triflate (18.2 mL, 100.4 mmol) was added at room temperature, and refluxing was continued for 3.5 h. Thereafter the reaction was stirred overnight at room temperature. Then the reaction mixture was diluted with dichloromethane (200 mL), washed with saturated sodium hydrogen carbonate solution, dried over sodium sulfate, and concentrated under reduced pressure. The residue was purified by silica gel column chromatography (1-2% methanol in dichloromethane) to afford 9-(2-O-acetyl-3-O-benzyl-5-O-mesyl-4-C-(mesyloxymethyl)-β-L-ribofuranosyl)N2-isobutyrylguanine (27.5 g, 83%) as a white solid.

$^{1}$H NMR ($CDCl_3$): δ 12.20 (br s, 1H), 9.34 (br s, 1H), 7.76 (s, 1H), 7.40-7.30 (m, 5H), 6.03 (d, 1H), 5.76 (dd, 1H), 5.08 (d, 1H), 4.91 (d, 1H), 4.67 (d, 1H), 4.61 (d, 2H), 4.49 (d, 1H), 4.39 (d, 1H), 4.32 (d, 1H), 3.14 (s, 3H), 3.02 (s, 3H), 2.70 (m, 1H), 2.09 (s, 3H) 1.24 (m, 6H).

MS (ESI): 671.7 Da confirmed.

(ii)

3'-O-Benzyl-5'-O-mesyl-β-L-LNA-N2-isobutyryl-G 9-(2-O-Acetyl-3-O-benzyl-5-O-mesyl-4-C-(mesyloxymethyl)-13-L-ribofuranosyl)N2-isobutyrylguanine (25 g, 37.2 mmol) was dissolved in tetrahydrofurane (250 mL). Then 1 M sodium hydroxide (250 mL, 250 mmol) was added, and the reaction mixture was stirred for 1 h at 0° C. Thereafter the solution was neutralized with acetic acid (15 mL) and concentrated under reduced pressure. The concentrated reaction mixture was diluted with water and extracted with dichloromethane. The organic layer was dried over sodium sulfate and concentrated to dryness under reduced pressure to yield 3'-O-benzyl-5'-O-mesyl-13-L-LNA-N2-isobutyryl-G (14.7 g, 74%) as a white solid which was used without purification for next reaction step.

$R_f$(5% methanol in dichloromethane)=0.57

$^{1}$H NMR ($CDCl_3$): δ 12.14 (br s, 1H), 9.51 (br s, 1H), 7.77 (s, 1H), 7.30-7.26 (m, 5H), 5.84 (s, 1H), 4.67 (d, 1H), 4.63 (d, 1H), 4.62 (s, 1H), 4.62 (d, 1H), 4.56 (d, 1H), 4.50 (s, 1H), 4.12 (d, 1H), 3.93 (d, 1H), 3.06 (s, 3H), 2.78 (m, 1H), 1.26 (m, 6H).

MS (ESI): 533.6 Da confirmed.

(iii)

5'-O-Benzoyl-3'-O-benzyl-β-L-LNA-N2-isobutyryl-G

3'-O-Benzyl-β-L-LNA-N2-isobutyryl-G

3'-O-Benzyl-5'-O-mesyl-β-L-LNA-N2-isobutyryl-G (12.5 g, 23.4 mmol) was dissolved in anhydrous N,N-dimethylformamide (250 mL). Thereafter sodium benzoate (6.8 g, 47 mmol) was added, and the mixture was stirred at 90° C. overnight, then cooled to room temperature, filtrated and concentrated under reduced pressure. The residue was dissolved in ethyl acetate (200 mL), washed with saturated sodium hydrogen carbonate solution and brine, dried over sodium sulfate, and concentrated to dryness under reduced pressure to afford 5'-O-benzoyl-3'-O-benzyl-13-L-LNA-N2-isobutyryl-G (MS (ESI): calc. 559.6, found 560.1). The product was used for the next reaction step without further purification. 5'-O-Benzoyl-3'-O-benzyl-13-L-LNA-N2-isobutyryl-G was dissolved in ethanol/pyridine 8:1 (350 mL). To this solution 2 M sodium hydroxide (13.5 mL) was added, and the mixture was stirred for 30 min at room temperature. Thereafter acetic acid (21.5 mL) was added, and the reaction mixture was concentrated under reduced pressure. The residue was crystallized from water/ethanol 1:1 to afford 3'-O-benzyl-β-L-LNA-N2-isobutyryl-G (8.2 g, 77%) as a white solid.

$R_f$ (10% methanol in ethyl acetate)=0.75

$^1$H NMR (DMSO-$d_6$): δ 8.05 (s, 1H), 7.33-7.26 (m, 5H), 5.85 (s, 1H), 5.17 (t, 1H), 4.69 (s, 1H), 4.64 (s, 2H), 4.23 (s, 1H), 3.95 (d, 1H), 3.83 (m, 2H), 3.80 (d, 1H), 2.78 (m, 1H), 1.12 (m, 6H).

MS (ESI): 455.5 Da confirmed.

(vi)

β-L-LNA-N2-isobutyryl-G

3'-O-Benzyl-β-L-LNA-N2-isobutyryl-G (8.2 g, 18.0 mmol) was dissolved in methanol (75 mL). Thereafter 20% palladium hydroxide on carbon (3 g) and formic acid (4.2 mL, 111.3 mmol) were added. The reaction mixture was refluxed for 5 h, cooled to room temperature and filtrated through a Celite pad. The filtrate was concentrated under reduced pressure to give β-L-LNA-N2-isobutyryl-G (6.2 g, 94%) as white solid.

$R_f$(10% methanol in ethyl acetate)=ca. 0.3.

$^1$H NMR (DMSO-$d_6$): δ 7.80 (s, 1H), 5.51 (s, 1H), 5.44 (br s, 1H), 4.77 (br s, 1H), 4.12 (s, 1H), 3.88 (s, 1H), 3.65 (d, 1H), 3.53 (m, 2H), 3.47 (d, 1H), 2.50 (m, 1H), 0.84 (m, 6H).

MS (ESI): 365.3 Da confirmed.

(v)

5'-O-(4,4'-Dimethoxytrityl)-β-L-LNA-N2-isobutyryl-G

β-L-LNA-N2-isobutyryl-G nucleoside (5 g, 13.7 mmol) was coevaporated with anhydrous pyridine (50 mL) and redissolved in anhydrous pyridine (150 mL). 4,4'-dimethoxytrityl chloride (6.0 g, 17.8 mmol) and 4-(dimethylamino)pyridine (0.17 g, 1.4 mmol) were added. The solution was stirred overnight at room temperature. After addition of methanol the reaction mixture was concentrated under reduced pressure. Thereafter the residue was dissolved in ethyl acetate (150 mL) and washed with saturated sodium hydrogen carbonate solution and brine, dried over sodium sulfate and concentrated under reduced pressure to dryness. Purification by silica gel column chromatography (starting from 20% hexane in ethyl acetate to ethyl acetate) afforded 5'-O-(4,4'-dimethoxytrityl)-β-L-LNA-N2-isobutyryl-G (8.0 g, 87%) as an off-white solid.

$R_f$(ethyl acetate)=0.39.

$^1$H NMR (DMSO-$d_6$): δ 12.09 (s, 1H), 11.78 (s, 1H), 8.00 (s, 1H), 7.39 (d, 2H), 7.30-7.24 (m, 7H), 6.88 (dd, 4H), 5.86 (s, 1H), 5.73 (d, 1H), 4.42 (s, 1H), 4.26 (d, 1H), 3.92 (dd, 1H), 3.88 (dd, 1H), 3.72 (s, 6H), 3.53 (d, 1H), 3.30 (d, 1H), 2.76 (m, 1H), 1.10 (d, 6H).

MS (ESI): 667.7 Da confirmed.

(vi)

5'-O-(4,4'-Dimethoxytrityl)-β-L-LNA-N2-isobutyryl-G,3'-[(2-cyanoethyl)-(N,N-diisopropyl)]phosphoramidite 5'-O-(4,4'-dimethoxytrityl)-β-L-LNA-N2-isobutyryl-G (7.5 g, 11.2 mmol) was dissolved in anhydrous dichloromethane (100 mL). Thereafter N,N-diisopropylethylamine (4.8 mL, 28.0 mmol) and 2-cyanoethyl N,N-diisopropylchlorophosphoramidite (4.24 g, 17.9 mmol) were added. The solution was stirred for 3 h at room temperature, and then washed with saturated sodium hydrogen carbonate solution. The organic layer was dried over sodium sulfate and concentrated to dryness under reduced pressure. The residue was purified by silica gel column chromatography (40% hexane in ethyl acetate) to yield 5'-O-(4,4'-dimethoxytrityl)-β-L-LNA-N2-isobutyryl-G,3'-[(2-cyanoethyl)-(N,N-diisopropyl)]phosphoramidite (6.8 g, 70%).

$R_f$(ethyl acetate)=0.66, 0.75.

$^{31}$P NMR (acetonitrile-d3): δ 148.51, 148.12.

MS (ESI): 867.9 Da confirmed.

EXAMPLE 6

Synthesis of 5'-biotinylated 13-L-LNA oligonucleotides

5'-Biotinylated 13-L-LNA oligonucleotides were synthesized in a 2×1 μmole scale synthesis on an ABI 394 DNA synthesizer using standard automated solid phase DNA synthesis procedure and applying phosphoramidite chemistry. Glen UnySupport PS (Glen Research cat no. 26-5040) and β-L-LNA phosphoramidites (from examples 2-5) as well as spacer phosphoramidite 18 (Glen Research cat. no. 10-1918) and 5'-biotin phosphoramidate (Glen Research cat. no. 10-5950) were used as building blocks. All phosphoramidites were applied at a concentration of 0.1 M in DNA grade acetonitrile. Standard DNA cycles with extended coupling time (180 sec), extended oxidation (45 sec) and detritylation time (85 sec) as well as standard synthesis reagents and solvents were used. 5'-Biotinylated oligonucleotides were synthesized DMToff. A standard cleavage program was applied for the cleavage of the LNA oligonucleotides from the support by concentrated ammonia, residual protecting groups were also cleaved by treatment with concentrated ammonia (8 h at 56° C.). Crude 5'-biotinylated β-L-LNA oligonucleotides were evaporated and purified by RP HPLC (column: PRP-1, 7 μm, 250×21.5 mm (Hamilton, part no. 79352)) using a 0.1 M triethylammonium acetate pH 7/acetonitrile gradient. Product fractions were combined and desalted by dialysis (MWCO 1000, SpectraPor 6, part no. 132638) against water. Finally, the LNA oligonucleotides were quantified and lyophilized.

Yields ranged from about 800 to 900 nmoles.

5'-Biotinylated β-L-LNA oligonucleotides were analyzed by RP18 HPLC (Chromolith RP18e, Merck, part no. 1.02129.0001) using a 0.1 M triethylammonium acetate pH 7/acetonitrile gradient. Typical purities were ≥90%. Identity of 5'-biotinylated β-L-LNA oligonucleotides were confirmed by LC-MS analysis.

EXAMPLE 7

Synthesis of 5'-maleimide-modified β-L-LNA oligonucleotides

5'-Maleimide-modified β-L-LNA oligonucleotides were synthesized in a 20 μmole scale synthesis on an Äkta Oligopilot plus 10 DNA synthesizer (GE Healthcare) using standard automated solid phase DNA synthesis procedure and applying phosphoramidite chemistry. Glen UnySupport PS (Glen Research cat no. 26-5040) and β-L-LNA phosphoramidites (from Examples 2-5) as well as spacer phosphoramidite 18 (Glen Research cat. no. 10-1918) and 5'-amino-modifier C6 phosphoramidite (Glen Research cat. no. 10-1906) were used as building blocks. All phosphoramidites were applied at a concentration of 0.15 M in DNA grade acetonitrile. Standard DNA cycles with extended coupling time (240 sec) and extended oxidation (45 sec) as well as standard synthesis reagents and solvents were used for the assembly of 5'-amino-modified β-L-LNA oligonucleotides which were synthesized MMTon. A standard cleavage program was applied for the cleavage of the LNA oligonucleotides from the support by concentrated ammonia, residual protecting groups were also cleaved by treatment with concentrated ammonia (8 h at 56° C.). Crude 5'-modified β-L-LNA oligonucleotides were evaporated and purified by RP HPLC (column: PRP-1, 12-20 μm, 250×30 mm (Hamilton, part no. 79352)) using a 0.1 M triethylammonium acetate pH 7/acetonitrile gradient. Product fractions were combined and desalted by dialysis (MWCO 1000, SpectraPor 6, part no. 132638) against water, thereby also cleaving MMT group of MMTon purified oligonucleotides. Finally, the 5'-amino-modified LNA oligonucleotides were quantified and lyophilized (typical yield: ca. 3.5 μmol). To synthesize 5'-maleimide modified β-L-LNA oligonucleotides 5'-amino-modified β-L-LNA oligonucleotides were dissolved in 0.1 M sodium borate buffer pH 7.5 (2.5 mL). After addition of acetonitrile (0.5 mL) and 6-maleimidohexanoic acid N-hydroxysuccinimide ester (15 mg; Sigma, cat. no. M9794) the reaction mixture was shaken for 0.5 h at room temperature, stopped with 80% acetic acid and desalted applying an Amicon ultra centrifugal filter device (MWCO 3000, Merck, cat no. UFC9003). The retentate was quantified and lyophilized to yield 5'-maleimide-modified β-L-LNA oligonucleotides.

Typical yields: ca. 2 μmoles.

5'-Maleimide-modified β-L-LNA oligonucleotides were analyzed by RP18 HPLC (Chromolith RP18e, Merck part no. 1.02129.0001) using a 0.1 M triethylammonium acetate pH 7/acetonitrile gradient. Typical purities were >90%. Identity of LNA oligonucleotides were confirmed by LC-MS analysis.

EXAMPLE 8

Synthesis of Unmodified β-L-LNA Oligonucleotides

Unmodified β-L-LNA oligonucleotides were synthesized in a 1 μmole scale synthesis on an ABI 394 DNA synthesizer using standard automated solid phase DNA synthesis procedure and applying phosphoramidite chemistry. Glen UnySupport PS (Glen Research cat no. 26-5040) and β-L-LNA phosphoramidites (from Examples 2-5) were used as building blocks. All phosphoramidites were applied at a concentration of 0.1 M in DNA grade acetonitrile. Standard DNA cycles with extended coupling time (180 sec), extended oxidation (45 sec) and detritylation time (85 sec) and standard synthesis reagents and solvents were used for the assembly of the LNA oligonucleotides which were synthesized as 5'-DMTon oligonucleotides. Then, a standard cleavage program was applied for the cleavage of the LNA oligonucleotides from the support by conc. ammonia. Residual protecting groups were cleaved by treatment with conc. ammonia (8 h at 56° C.). Crude LNA oligonucleotides were evaporated and purified by RP HPLC (column: PRP-1, 7 μm, 250×21.5 mm (Hamilton, part no. 79352)) using a 0.1 M triethylammonium acetate pH 7/acetonitrile gradient. In few cases, difficult to purify LNA oligonucleotides were additionally purified by anion exchange HPLC chromatography under denaturing conditions (column: Source 15Q, GE Healthcare). Product fractions were combined and desalted by dialysis (MWCO 1000, SpectraPor 6, part no. 132638) against water, thereby also cleaving DMT group of DMTon purified oligonucleotides. Finally, the LNA oligonucleotides were quantified and lyophilized.

Yields ranged from about 100 to 400 nmoles.

LNA oligonucleotides were analyzed by RP18 HPLC (Chromolith RP18e, Merck part no. 1.02129.0001) using a 0.1 M triethylammonium acetate pH 7/acetonitrile gradient. Typical purities were ≥90%. Identity of LNA oligonucleotides were confirmed by LC-MS analysis.

EXAMPLE 9

Coupling of L-LNA Oligonucleotides to TSH-Specific $F(Ab')_2$-Fragments (Thyrotropin-Specific Capturing Agent)

$F(ab')_2$-Fragments were conjugated with LNA in a two step reaction. Firstly, thiol-groups were introduced into $F(ab')_2$-fragments via conjugation with SATP (N-succinimidyl-S-acetythiopropionate) and deacetylation by hydroxylamine (see Greg T. Hermanson Bioconjugate Techniques, 3rd edition 2013). L-LNA-oligonucleotides of Seq ID NO:9 were then conjugated to free thiols via maleimiide chemistry. L-LNA labeled $F(ab')_2$ fragments were purified via Superdex 200 size-exclusion and mono Q anion exchange chromatography to obtain conjugated $F(ab')_2$ fragments of high purity, with each conjugate comprising a single L-LNA oligomer.

EXAMPLE 10

Use of Complementary L-LNA Oligonucleotides as a Binding Pair in a Roche Cobas® Elecsys® Analytical Electro-Chemiluminescence Immunoassay to Determine TSH (Thyrotropin) in Human Serum and Plasma ECL (ElectroChemiLuminescence) is Roche's technology for immunoassay detection. Based on this technology and combined with specific and sensitive TSH immunoassays, Elecsys yielded reproducible results. The development of ECL immunoassays is based on the use of a ruthenium-complex and tripropylamine (TPA). The chemiluminescence reaction for the detection of the reaction complex is initiated by applying a voltage to the sample solution resulting in a precisely controlled reaction. ECL technology can accommodate many immunoassay principles and formats while providing advantageous performance.

Commercially available Cobas® Elecsys® TSH kits (No. 11731459, Roche Diagnostics GmbH, Mannheim, Germany) were modified. The reagent kit contains three bottles, one bottle containing a suspension of streptavidin-coated beads, one bottle containing the first reagent (R1) and one bottle containing the second reagent (R2). To the bottle containing the streptavidin-coated beads the L-LNA oligonucleotide of Seq ID NO:10 which was 5'-labeled with a biotin-$(HEG)_4$-moiety (HEG=hexaethylene glycol) was added at two different concentrations, either 0.2 nmol or 0.5 nmol L-LNA oligonucleotide per mg beads.

The R1 bottle contained the same components as the commercially available kit, except that the biotin-antiTSH antibody conjugate was replaced by an L-LNA antiTSH conjugate described above in Example 9 (concentration 2.5 μg/ml). The ingredients in the R2 bottle were identical as in the commercially available kit.

Figure 6:
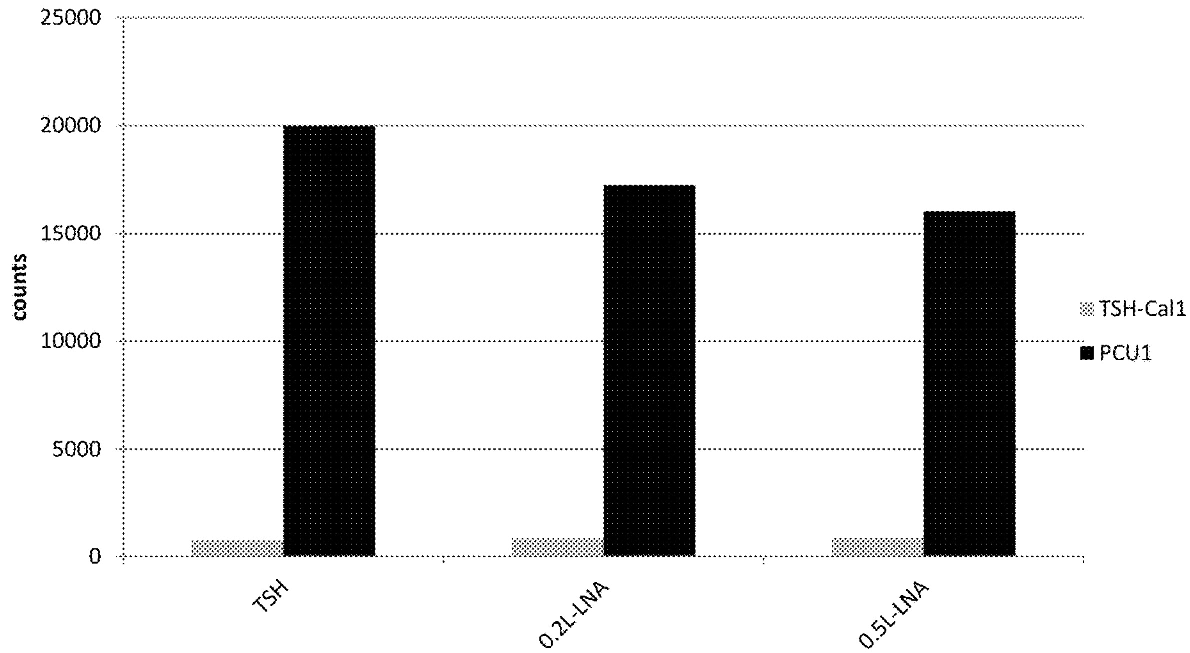
FIG. 6 A and B are illustrations of the results of Example 10.
Figure 6:
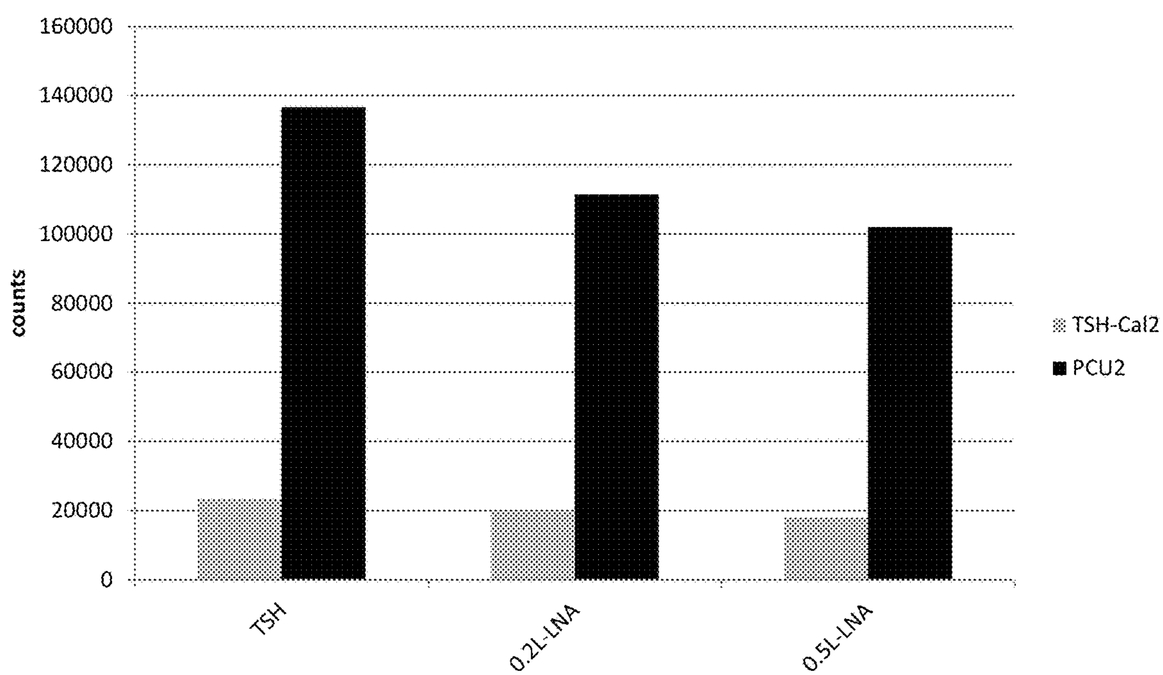

The above mentioned assay reagents were used to measure samples (calibrators and controls), in comparison with the commercially available assay. Measurements were performed on a Cobas® Elecsys® e411 analyzer. Results are depicted in FIGS. 6A and 6B.

Elecsys® TSH test characteristics, commercially available version, not modified

Test principle One-step sandwich assay

Sample material Serum

Li-, Na-, $NH_4^+$-heparin plasma $K_3$-EDTA, Na-citrate, NaF, K-oxalate plasma

Sample volume 50 μL

Detection limit 0.005 IU/mL

Functional sensitivity 0.014 IU/mL

Measuring range 0.005-100 IU/mL

FIG. 6A shows the comparison of signals (counts) measured with the commercially available assay Cobas® Elecsys® TSH kit (designated "TSH" in FIG. 6A) and modified kits containing 0.2 nmol/mg beads (designated "0.2 L-LNA" in FIG. 6A) or 0.5 nmol/mg beads Biotin-L-LNA oligonucleotides (designated "0.5 L-LNA" in FIG. 6A) in the bead reagent bottle. Samples measured were calibrator 1 ("Cal1") and a level 1 control ("PCU1"). Reagent 1 (R1) and Reagent 2 (R2) bottle content as described above.

FIG. 6B shows the comparison of signals (counts) measured with the commercially available assay Cobas® Elecsys® TSH kit (designated "TSH" in FIG. 6B) and modified kits containing 0.2 nmol/mg beads (designated "0.2 L-LNA" in FIG. 6B) or 0.5 nmol/mg beads Biotin-L-LNA oligonucleotides (designated "0.5 L-LNA" in FIG. 6B) in the bead reagent bottle. Samples measured were calibrator 2 ("Cal2") and a level 2 control (PCU2). Reagent 1 (R1) and Reagent 2 (R2) bottle content as described above.

Roche Product Id numbers were Elecsys® TSH 200 tests 11731459; TSH CalSet 4×1.3 mL 04738551; PreciControl Universal (PCU) 2×3 mL each 11731416; PreciControl TSH 4×2 mL 11776479; Diluent MultiAssay 2×16 mL 03609987.

EXAMPLE 11

Coupling of L-LNA Oligonucleotides to TSH-Specific $F(Ab')_2$-Fragments (Thyrotropin-Specific Capturing Agent)

$F(ab')_2$-Fragments were conjugated with LNA in a two step reaction. Firstly, thiol-groups were introduced into F(ab')2-fragments via conjugation with SATP (N-succinimidyl-S-acetythiopropionate) and deacetylation by hydroxylamine (see Greg T. Hermanson Bioconjugate Techniques, 3rd edition 2013). L-LNA-oligonucleotides of Seq ID NO:9 were then conjugated to free thiols via maleimide chemistry. L-LNA labeled $F(ab')_2$ fragments were purified via Superdex 200 size-exclusion and mono Q anion exchange chromatography to obtain conjugated $F(ab')_2$ fragments of high purity, with each conjugate comprising a single L-LNA oligomer.

EXAMPLE 12

Use of Complementary L-LNA Oligonucleotides as a Binding Pair in a Roche Cobas® Elecsys® Analytical Electro-Chemiluminescence Immunoassay to Determine TSH (Thyrotropin) in Human Serum and Plasma The Elecsys® Troponin T Immunoassay is an immunoassay for the in vitro quantitative determination of cardiac troponin T in Heparin, EDTA plasma and serum. The immunoassay is intended to aid in the diagnosis of myocardial infarction.

The electrochemiluminescence immunoassay "ECLIA" is intended for use on the Cobas® system analyzers.

Sample material: Serum,

Li-, Na-Heparin-Plasma, $K_2$- and $K_3$-EDTA

Sample volume 50 μL

10% CV precision: 13 ng/L (pg/mL)

Measuring range 3-10,000 pg/mL

Limit of detection: 5 ng/L (pg/mL)

Limit of blank: 3 ng/L (pg/mL)

Commercially available Cobas® Elecsys® TNThs kits (No. 05092744190, Roche Diagnostics GmbH, Mannheim, Germany) were modified. The reagent kit contains three bottles, one bottle containing a suspension of streptavidin-coated beads, one bottle containing the first reagent (R1) and one bottle containing the second reagent (R2). To the bottle containing the streptavidin-coated beads the L-LNA oligonucleotide of Seq ID NO:10 which was 5'-labeled with a biotin-$(HEG)_4$-moiety (HEG=hexaethylene glycol) was added at two different concentrations, either 0.2 nmol or 0.5 nmol L-LNA oligonucleotide per mg beads.

The R1 bottle contained the same components as the commercially available kit, except that the biotin-antiTNT antibody conjugate was replaced by an L-LNA antiTSH conjugate described above in Example 11 (concentration 2.5 μg/ml). The ingredients in the R2 bottle were identical as in the commercially available kit.

The above mentioned assay reagents were used to measure samples (calibrators and controls), in comparison with the commercially available assay. Measurements were performed on a Cobas® Elecsys® e411 analyzer. Results are depicted in FIGS. 7A and 7B.

Figure 7:
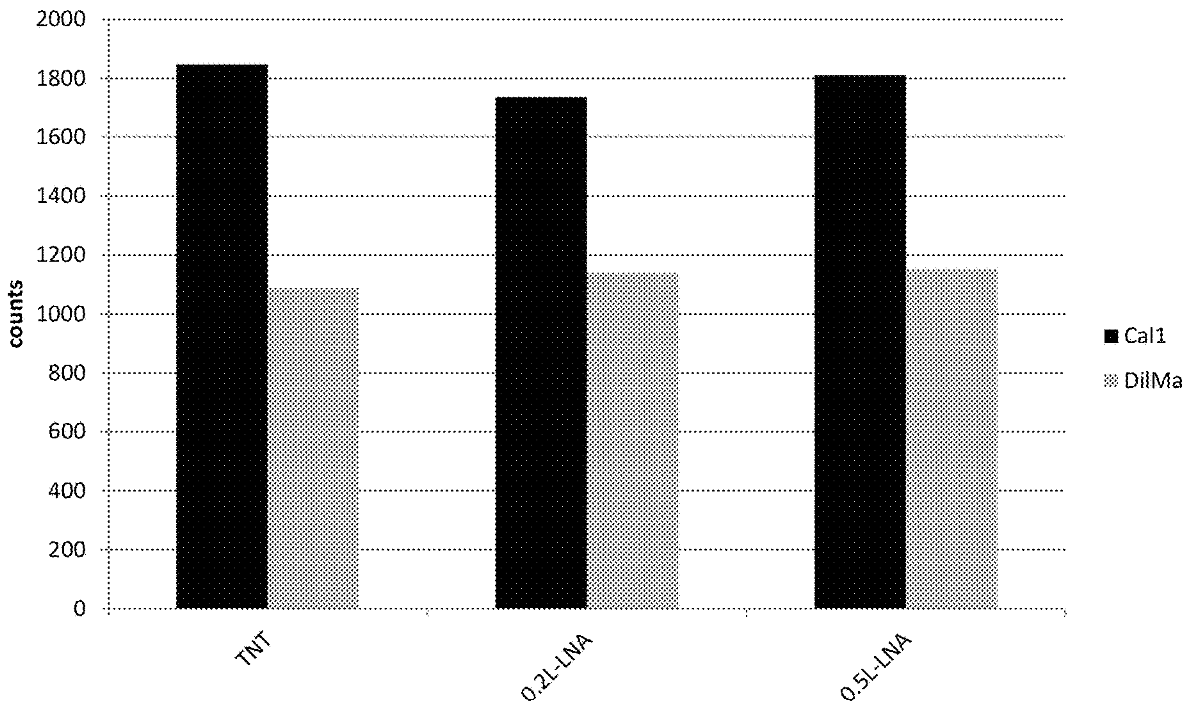
FIG. 7 A and B are illustrations of the results of Example 12.
Figure 7:
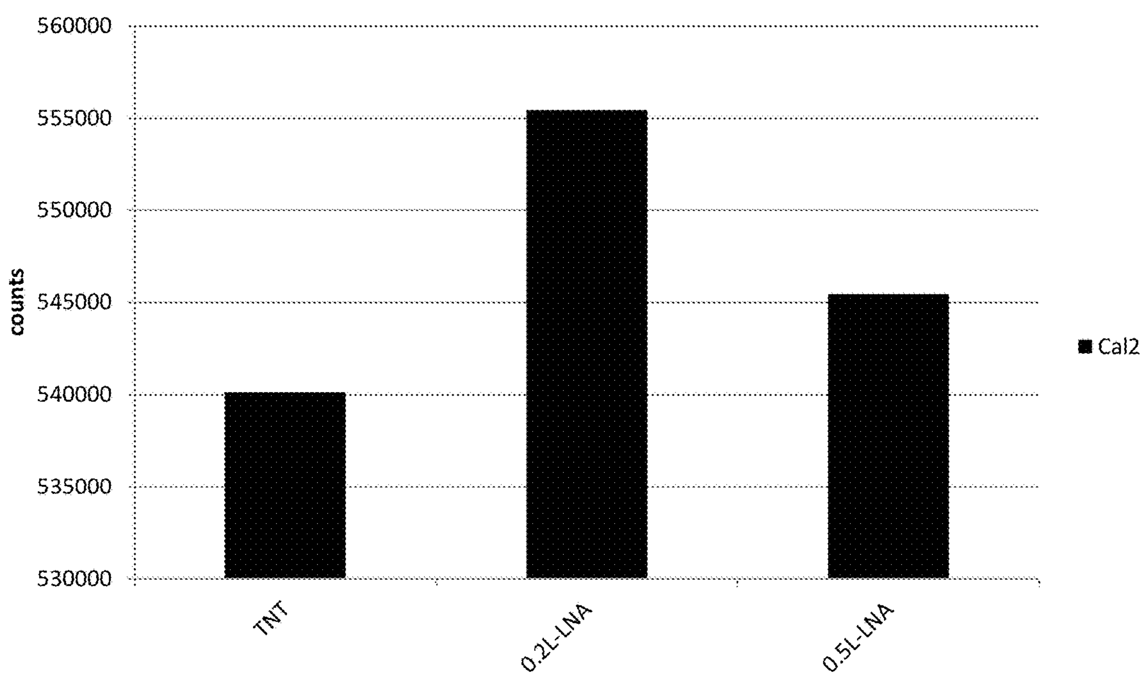

FIG. 7A shows the comparison of signals (counts) measured with the commercially available assay Cobas® Elecsys® TNThs kit (designated "NT" in FIG. 7A) and modified kits containing 0.2 nmol/mg beads (designated "0.2 L-LNA" in FIG. 7A) or 0.5 nmol/mg beads Biotin-L-LNA oligonucleotides (designated "0.5 L-LNA" in FIG. 7A) in the bead reagent bottle. Samples measured were calibrator 1 ("Cal2") and a dilution medium containing no analyte ("DilMa"). Reagent 1 (R1) and Reagent 2 (R2) bottle content as described above.

FIG. 7B shows the comparison of signals (counts) measured with the commercially available assay Cobas® Elecsys® TSHhs kit (designated "TNT" in FIG. 7B) and modified kits containing 0.2 nmol/mg beads (designated "0.2 L-LNA" in FIG. 7B) or 0.5 nmol/mg beads Biotin-L-LNA oligonucleotides (designated "0.5 L-LNA" in FIG. 7B) in the bead reagent bottle. Samples measured were calibrator 2 ("Cal2"). Reagent 1 (R1) and Reagent 2 (R2) bottle content as described above.

Roche Product Id numbers were Elecsys Troponin T high sensitive 200 Tests 05 092 744 190; ElecsysT Troponin T high sensitive (STAT) 100 Tests 05 092 728 190; CalSet Troponin T high sensitive ElecsysT 10 calibrations 05 092 752 190; CalSet Troponin T high sensitive (STAT) ElecsysT 10 calibrations 05 092 736 190; Diluent Universal ElecsysT 2×16 mL/2×36 mL 11 732 277 122/03 183 971 122.

EXAMPLE 13

Figure 8:
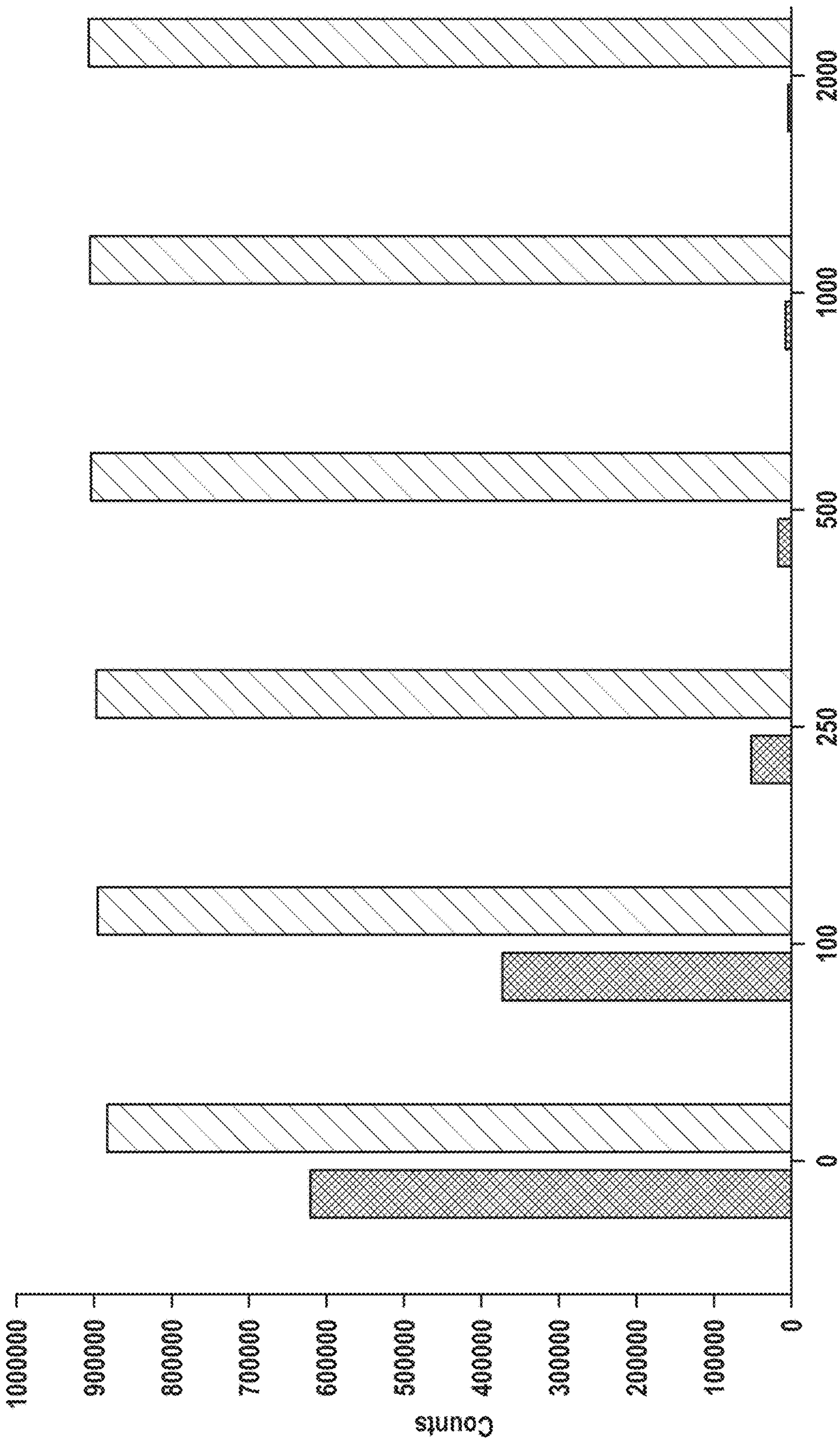
FIG. 8 Diagram illustrating the results of Example 13.

Formation of L-LNA Oligonucleotide Binding Pairs is not Affected by Interference by Free Biotin Original Elecsys® beads in a Troponin T hs Elecssys® assay (Id. 05092744190) were replaced by Elecsys beads coated with biotinylated LNA oligos (0.308 nMol L-LNA/ml beads). Additionally the biotinylated specifier Mab<TNT>-Fab-Bi was replaced in the R1 bottle by a Fab conjugated containing a complementary L-LNA-oligomer at an engineered cysteine at a position Q195 conjugated by maleimide chemistry. This new Troponin T hs Elecsys® assay variant using LNA hybridization to immobilize Troponin T immune-complexes on the streptavidin-coated beads, and a conventional commercial Troponin T hs Elecsys assay (Id. 05092744190) were run in parallel on a cobas E170 device with Cal2 samples from Troponin T hs CalSet (Id. 05092752190) without and supplemented with D-Biotin at concentrations of 100, 250, 500, 1000 and 2000 ng/ml. See FIG. 8, dark bars indicating the results of the unmodified commercial assay, bright bars representing the measurements using the complementary pair of L-LNA oligonucleotides. In contrast to the original assay no significant signal loss could be observed in the new assay variant using LNA hybridization to immobilize Troponin T immune-complexes on streptavidin-coated Elecsys® beads.

Comparable results can be obtained using different binding pairs, e.g.

```
                        (Seq ID NO: 5)
5' tgctcctg 3'

                        (Seq ID NO: 6)
5' caggagca 3',

                        (Seq ID NO: 7)
5' gcctgacg 3'

                        (Seq ID NO: 8)
5' cgtcaggc 3',
```

-continued

```
                        (Seq ID NO: 9)
5' tgctcctgt 3'

                        (Seq ID NO: 10)
5' acaggagca 3',

                        (Seq ID NO: 11)
5' gtgcgtct 3'

                        (Seq ID NO: 12)
5' agacgcac 3',

                        (Seq ID NO: 13)
5' gttggtgt 3'

                        (Seq ID NO: 14)
5' acaccaac 3'

                        (Seq ID NO: 15)
5' gttggtgtgttggtg 3'

                        (Seq ID NO: 16)
5' caccaacacaccaac 3'

                        (Seq ID NO: 17)
5' gttggtgtg 3'

                        (Seq ID NO: 18)
5' cacaccaac 3'

                        (Seq ID NO: 19)
5' ggaagagaa 3'

                        (Seq ID NO: 20)
5' ttctatcc 3'.
```

The invention claimed is:

1. A solid phase coated with (strept) avidin and having attached thereto, by way of <biotin: (strept) avidin> interaction, a biotinylated first member of a binding pair, wherein the attached first member is capable of binding to a second member of the binding pair, but is not capable of binding to biotin or to (strept) avidin, wherein the second member is capable of becoming bound by the first member when the second member is part of a conjugate comprising any of an analyte, an analyte analogon, and an analyte-specific capturing agent;

wherein the binding pair comprises a first and a second oligomer consisting of beta-L-LNA nucleoside monomers, the first oligomer being capable of hybridizing with the second oligomer.

2. The solid phase of claim 1, wherein the solid phase is obtainable by a method comprising the steps of (a) providing a solid phase coated with (strept) avidin;

(b) selecting a binding pair with a first member and a second member;

(c) providing the first member of the binding pair selected in step (b);

(d) biotinylating the first member of step (c);

(e) attaching the biotinylated first member obtained from step (d) to the solid phase of step (a) by contacting the biotinylated first member with the coated solid phase and incubating, thereby attaching the biotinylated first member to the solid phase by way of biotin-(strept) avidin interaction;

wherein in step (b) the binding pair comprises a first and a second oligomer consisting of beta-L-LNA nucleoside monomers, the first oligomer being capable of hybridizing with the second oligomer.

3. The solid phase of claim 1, wherein the solid phase is selected from the group consisting of a microparticle, a microwell plate, a test tube, a cuvette, a membrane, a quartz crystal, a film, a filter paper, a disc and a chip.

4. The solid phase of claim 3, wherein the solid phase is a microparticle with a diameter from 0.05 μm to 200 μm.

5. The solid phase of claim 4, wherein the microparticle is a monodisperse paramagnetic bead.

6. The solid phase of claim 5, wherein the diameter of the bead is about 3 μm.

7. The solid phase of claim 1, wherein the solid phase is in contact with an aqueous liquid phase.

8. The solid phase of claim 7, wherein in the liquid phase contains a conjugate, the conjugate comprising a second member of the binding pair.

9. A method of determining an analyte in a sample, the method comprising conducting an assay using the solid phase of claim 1.

10. A kit for determining an analyte in a sample, the kit comprising (a) in a first container, and either (b) or (c) in a second container, wherein (a) is a solid phase having attached thereto a first member of a binding pair, wherein the solid phase is a solid phase of claim 1, (b) is a first conjugate, the conjugate comprising a second member of the binding pair coupled to an analyte-specific capturing agent, (c) is a second conjugate, the conjugate comprising a second member of the binding pair coupled to an analyte or an analogon of an analyte;

wherein the binding pair comprises a first and a second oligomer consisting of beta-L-LNA nucleoside monomers, the first oligomer being capable of hybridizing with the second oligomer.

11. The kit of claim 10, the kit comprising (a) and (b), the kit further comprising a labeled analyte-specific detecting agent, wherein the detecting agent and (b) are in different containers, and wherein the analyte-specific capturing agent of (b) and the labeled analyte-specific detecting agent are capable of forming a sandwich complex with the analyte.

12. The kit of claim 10, the kit comprising (a) and (c), the kit further comprising a labeled analyte-specific detecting agent, wherein the detecting agent and (c) are in different containers, and wherein the analyte or analyte analogon comprised in the conjugate and the analyte in the sample are capable of being bound by the detecting agent.

13. A complex comprising (a) and either (b) or (c), wherein (a) is a solid phase having attached thereto a first member of a binding pair, wherein the solid phase is a solid phase of claim 1, (b) is a first conjugate, the conjugate comprising a second member of the binding pair coupled to an analyte-specific capturing agent, (c) is a second conjugate, the conjugate comprising a second member of the binding pair coupled to an analyte or an analogon of an analyte, wherein in the complex (a) is bound to (b) or (c), respectively, wherein in the complex a first member of the binding pair is bound to a second member of the binding pair, and wherein the binding pair comprises a first and a second oligomer consisting of beta-L-LNA nucleoside monomers, the first oligomer being capable of hybridizing with the second oligomer.

14. A method to form a complex, the method comprising the step of contacting (a) with either (b) or (c), wherein (a) is a solid phase having attached thereto a first member of a binding pair, wherein the solid phase is a solid phase of claim 1, (b) is a first conjugate, the conjugate comprising a second member of the binding pair coupled to an analyte-specific capturing agent, (c) is a second conjugate, the conjugate comprising a second member of the binding pair coupled to an analyte or an analogon of an analyte, followed by the step of incubating (a) and either (b) or (c), respectively, thereby forming the complex, wherein in the complex (a) is bound to (b) or (c), respectively, wherein a first member of the binding pair is bound to a second member of the binding pair, and wherein the binding pair comprises a first and a second oligomer consisting of beta-L-LNA nucleoside monomers, the first oligomer being capable of hybridizing with the second oligomer.

15. A complex obtainable by a method of claim 14.

16. A method to determine an analyte in a sample, the method comprising the steps of (a) providing the sample with the analyte;

(b) providing a solid phase having attached thereto a first member of a binding pair, wherein the solid phase is a solid phase of claim 1;

(c) providing a conjugate, the conjugate comprising a second member of the binding pair coupled to an analyte-specific capturing agent;

(d) contacting, mixing and incubating the sample of (a) with conjugate of (c), thereby forming a complex, the complex comprising the analyte being captured by the analyte-specific capturing agent comprised in the conjugate;

(e) immobilizing complex formed in step (d) by contacting and incubating complex with the solid phase of step (b), wherein the first member of the binding pair binds to the second member;

(f) optionally washing immobilized complex obtained from step (e);

(g) determining analyte comprised in immobilized complex;

thereby determining the analyte in the sample, wherein the binding pair comprises a first and a second oligomer consisting of beta-L-LNA nucleoside monomers, the first oligomer being capable of hybridizing with the second oligomer.

17. The method of claim 16, wherein steps (d) and (e) are performed subsequently or simultaneously.

18. The method of claim 16, wherein step (c) additionally comprises providing a labeled analyte-specific detecting agent, the analyte is capable of being bound simultaneously by the capturing agent comprised in the conjugate and by the detecting agent, thereby being capable of forming a sandwich complex;

step (d) comprises contacting, mixing and incubating the sample of (a) with the conjugate of (c) and additionally labeled analyte-specific detecting agent, thereby forming a complex, the complex comprising analyte being sandwiched between the capturing agent and the detecting agent, and step (g) is performed by determining label comprised in immobilized complex.

19. The method of claim 18, wherein prior to step (g) unbound labeled analyte-specific detecting agent is removed from immobilized complex.

20. A method to determine an analyte in a sample, the method comprising the steps of (a) providing the sample with the analyte;

(b) providing a solid phase having attached thereto a first member of a binding pair, wherein the solid phase is a solid phase of claim 1;

(c) providing a conjugate, the conjugate comprising a second member of the binding pair coupled to the analyte or an analogon of the analyte;

(d) providing a labeled analyte-specific detecting agent, wherein the analyte or analyte analogon comprised in the conjugate of step (c) and the analyte in the sample are capable of being bound by the detecting agent;

(e) contacting, mixing and incubating the sample of step (a) with conjugate of step (c) and detecting agent of step (d), thereby forming a first complex comprising the analyte and the detecting agent and a second complex comprising the conjugate and the detecting agent;

(f) immobilizing second complex formed in step (e) by contacting and incubating complex with the solid phase of step (b), wherein the first member of the binding pair binds to the second member;

(g) optionally washing the immobilized complex obtained from step (f);

(h) determining label comprised in the immobilized complex obtained from step (f) or step (g);

thereby determining the analyte in the sample, and wherein the binding pair comprises a first and a second oligomer consisting of beta-L-LNA nucleoside monomers, the first oligomer being capable of hybridizing with the second oligomer.

21. The method of claim 20, wherein steps (e) and (f) are performed subsequently or simultaneously.

22. The method of claim 20, wherein prior to step (h) unbound labeled analyte-specific detecting agent is removed from immobilized complex.

23. The method of claim 20, wherein a predetermined amount of each of (c) and/or (d) is provided.

24. A method of preparing a solid phase having attached thereto a member of a binding pair, the method comprising the steps of (a) providing a solid phase coated with (strept) avidin;

(b) selecting a binding pair with a first member and a second member;

(c) providing the first member of the binding pair selected in step (b);

(d) biotinylating the first member of step (c);

(e) attaching the biotinylated first member obtained from step (d) to the solid phase of step (a) by contacting the biotinylated first member with the coated solid phase and incubating, thereby attaching the biotinylated first member to the solid phase by way of biotin-(strept) avidin interaction;

wherein in step (b) the binding pair comprises a first and a second oligomer consisting of beta-L-LNA nucleoside monomers, the first oligomer being capable of hybridizing with the second oligomer;

thereby obtaining the solid phase having attached thereto the first member of the binding pair.

* * * * *